US012594245B2

(12) United States Patent
DeRosa et al.

(10) Patent No.: US 12,594,245 B2
(45) Date of Patent: Apr. 7, 2026

(54) DRY POWDER FORMULATIONS FOR MESSENGER RNA

(71) Applicant: Translate Bio, Inc., Lexington, MA (US)

(72) Inventors: Frank DeRosa, Cambridge, MA (US); Michael Heartlein, Cambridge, MA (US); Shrirang Karve, Cambridge, MA (US); Zarna Patel, Cambridge, MA (US); Ashish Sarode, Cambridge, MA (US)

(73) Assignee: Translate Bio, Inc., Lexington, MA (US)

( * ) Notice: Subject to any disclaimer, the term of this patent is extended or adjusted under 35 U.S.C. 154(b) by 150 days.

(21) Appl. No.: 17/745,428

(22) Filed: May 16, 2022

(65) Prior Publication Data

US 2023/0000781 A1 Jan. 5, 2023

Related U.S. Application Data

(62) Division of application No. 16/520,000, filed on Jul. 23, 2019, now abandoned.

(60) Provisional application No. 62/702,193, filed on Jul. 23, 2018.

(51) Int. Cl.

| | |
|---|---|
| ***A61K 9/50*** | (2006.01) |
| ***A61K 9/00*** | (2006.01) |
| ***A61K 9/48*** | (2006.01) |
| ***A61K 9/51*** | (2006.01) |
| ***A61K 38/17*** | (2006.01) |
| ***A61K 38/45*** | (2006.01) |
| ***A61K 48/00*** | (2006.01) |
| ***A61P 11/00*** | (2006.01) |

(52) U.S. Cl.

CPC .......... *A61K 9/5015* (2013.01); *A61K 9/0075* (2013.01); *A61K 9/0078* (2013.01); *A61K 9/4866* (2013.01); *A61K 9/5031* (2013.01); *A61K 9/5089* (2013.01); *A61K 9/5123* (2013.01); *A61K 9/5153* (2013.01); *A61K 38/1709* (2013.01); *A61K 38/177* (2013.01); *A61K 38/45* (2013.01); *A61K 48/0033* (2013.01); *A61K 48/0075* (2013.01); *A61P 11/00* (2018.01)

(58) Field of Classification Search

None

See application file for complete search history.

(56) References Cited

U.S. PATENT DOCUMENTS

| | | | | |
|---|---|---|---|---|
| 9,181,321 | B2 | 11/2015 | Heartlein et al. | |
| 9,713,626 | B2 | 7/2017 | Heartlein et al. | |
| 10,266,559 | B2 | 4/2019 | Derosa et al. | |
| 10,822,368 | B2 | 11/2020 | Derosa et al. | |
| 2002/0150626 | A1 | 10/2002 | Kohane et al. | |
| 2003/0203865 | A1 | 10/2003 | Harvie et al. | |
| 2004/0115254 | A1 | 6/2004 | Niedzinski et al. | |
| 2008/0202513 | A1 | 8/2008 | Birchall et al. | |
| 2011/0077284 | A1 | 3/2011 | Brito et al. | |
| 2012/0219590 | A1* | 8/2012 | Patel | A61P 31/20 424/233.1 |
| 2013/0243828 | A1* | 9/2013 | Lipp | A61P 11/10 424/400 |
| 2014/0113960 | A1 | 4/2014 | Heartlein | |
| 2015/0140036 | A1* | 5/2015 | Mannick | A61P 35/02 435/5 |
| 2015/0157565 | A1* | 6/2015 | Heartlein | A61K 31/7088 128/200.14 |
| 2016/0106772 | A1 | 4/2016 | Bancel | |
| 2016/0122759 | A1 | 5/2016 | Kasperkovitz et al. | |
| 2016/0243259 | A1 | 8/2016 | Almarsson et al. | |
| 2017/0314041 | A1 | 11/2017 | Derosa et al. | |
| 2018/0085391 | A1 | 3/2018 | Bouchon et al. | |
| 2018/0085474 | A1 | 3/2018 | Almarsson et al. | |
| 2020/0022921 | A1 | 1/2020 | Karve et al. | |
| 2021/0378977 | A1 | 12/2021 | Karve et al. | |
| 2022/0249699 | A1 | 8/2022 | Guild et al. | |

FOREIGN PATENT DOCUMENTS

| | | | |
|---|---|---|---|
| JP | 2000507568 | A | 6/2000 |
| JP | 2001526634 | A | 12/2001 |
| JP | 2004535388 | A | 11/2004 |
| WO | 9736578 | A1 | 10/1997 |
| WO | 9831346 | A1 | 7/1998 |
| WO | WO 2012/170889 | A1 | 12/2012 |
| WO | WO 2013/149140 | A1 | 10/2013 |
| WO | WO 2013/185069 | A1 | 12/2013 |
| WO | WO 2014/153052 | A2 | 9/2014 |
| WO | WO 2016/118725 | A1 | 7/2016 |
| WO | WO 2017/177169 | A1 | 10/2017 |
| WO | 2018011406 | A1 | 1/2018 |

(Continued)

OTHER PUBLICATIONS

Chen et al (The effect of polymer coatings on physicochemical properties of spray-dried liposomes for nasal delivery of BSA. European Journal of Pharmaceutical Sciences 50 (2013) 312-322) (Year: 2013).*

Patra et al (Pharmaceutical significance of Eudragit: A review. Future Journal of Pharmaceutical Sciences 3 (2017) 33-45) (Year: 2017).*

Spray Drying (Training Papers Spray Drying. p. 1-19. (2002)) (Year: 2002).*

Eric WFW Alton et al., "A randomised, double-blind, placebo-controlled trial of repeated nebulisation of non-viral cystic fibrosis transmembrane conductance regulator (CFTR) gene therapy in patients with cystic fibrosis", Efficacy and Mechanism Evaluation, Jul. 2016, vol. 3, No. 5, Southampton (UK): NIHR Journals Library; PMID: 27441329, 240 pages.

(Continued)

*Primary Examiner* — Jake M Vu

(74) *Attorney, Agent, or Firm* — MH2 Technology Law Group, LLP

(57) ABSTRACT

The present invention provides stable, dry powder messenger RNA formulations for therapeutic use, and methods of making and using the same.

28 Claims, 16 Drawing Sheets

Specification includes a Sequence Listing.

(56) References Cited

FOREIGN PATENT DOCUMENTS

| | | | |
|---|---|---|---|
| WO | 2018089688 | A1 | 5/2018 |
| WO | 2019207060 | A1 | 10/2019 |

OTHER PUBLICATIONS

Office Action dated Jun. 1, 2023 for corresponding Japanese Patent Application No. 2021-503720, 15 pages with English translation.
Non-Final Office Action dated Aug. 16, 2023 for related U.S. Appl. No. 17/262,421, 18 pages.
Philippe Couckuyt (Authorized Officer), International Search Report dated Oct. 15, 2019 for related International Application No. PCT/US2019/043074, 7 pages.
Athina Nickitas-Etienne (Authorized Officer), International Preliminary Report on Patentability dated Jan. 26, 2021 for related International Application No. PCT/US2019/043074, 7 pages.
Alton et al., "A randomized, double-blind, placebo-controlled trial of repeated nebulization of non-viral cystic fibrosis transmembrane conductance regulator (CFTR) gene therapy in patients with cystic fibrosis", National Institute for Health Research, 3(5), 2016.
International Search Report relating to International Application No. PCT/US2019/043074 dated Oct. 15, 2019, 7 pages.
Cayman Chemical, Cayman Product Information on OF-02, Item No. 37652, CAS Registry No. 1883431-67-1, 2024, obtained online Jan. 22, 2024, 1 page.
Canadian Office Action dated Oct. 10, 2023 for Canadian Application No. 3,107,055, 3 pages.
US Final Office Action dated Jan. 25, 2024 for U.S. Appl. No. 17/262,421, 28 pages.
Chinese First Office Action dated Jan. 22, 2024 for Chinese Application No. 201980056886.2, 33 pages with English Translation.
Singapore Written Opinion dated Sep. 23, 2022 for Singapore Application No. 112021006025, 6 pages.
Van De Wetering et al., "Structure-Activity Relationships of Water-Soluble Cationic Methacrylate/Methacrylamide Polymers for Nonviral Gene Delivery," Bioconjugate Chem., 1999, vol. 10, pp. 589-597.
US Non-Final Office Action dated Feb. 17, 2022 for U.S. Appl. No. 16/520,000, 15 pages.
Chinese Second Office Action dated Aug. 29, 2024 for Chinese Applicatio No. 201980056886.2, 17 pages, with English Translation.
Korean Office Action dated Aug. 23, 2024 for Korean Application No. 10-2021-7005235, 17 pages, with English Translation.
Chinese Search Report dated Aug. 27, 2024 for Chinese Application No. 201980056886.2, 3 pages.
Jenks, Ulrike W., et al. (US Administative Patent Judges), Decision on Appeal from the US Patent Trial and Appeal Board in Appeal No. 2025-001907 issued Dec. 5, 2025 for U.S. Appl. No. 17/262,421, 15 pages.
Lee, Geoffrey, "Spray-Drying of Proteins," Rational Design of Stable Protein Formulations, 2002, pp. 135-136 (J.F. Carpenter et al. (Eds.), Kluwer Academic/Plenum Publishers, New York).

* cited by examiner

DRY POWDER FORMULATIONS FOR MESSENGER RNA

CROSS REFERENCE TO RELATED APPLICATIONS

This application is a divisional application of U.S. patent application Ser. No. 16/520,000, filed Jul. 23, 2019, which claims priority to U.S. Provisional Patent Application No. 62/702,193 filed Jul. 23, 2018. The foregoing applications are incorporated by reference herein in their entirety.

INCORPORATION BY REFERENCE OF SEQUENCE LISTING

This application contains a Sequence Listing which has been submitted electronically in ASCII format and is hereby incorporated by reference in its entirety. Said ASCII copy, created on May 16, 2022, is named MRT_2008US2_ST25.txt and is 2 kilobytes in size.

BACKGROUND

Messenger RNA therapy (MRT) is becoming an increasingly important approach for the treatment of a variety of diseases. Lipid encapsulated mRNA formulations, such as lipid nanoparticle (LNP) compositions show high degree of cellular uptake and protein expression. However, presently these formulations are typically in liquid forms, and are required to be administered usually in the form of injections, or via nebulizers. These modes of administration are less desired by the patient than some less invasive routes, for example, metered dose inhalers. Lyophilized formulations sometimes do not offer reliable particle uniformity in dry state, or ease of handling and distribution. Lyophilized powder has to be dissolved in an appropriate solvent prior to dispensing to a patient and can undergo degradation within a few hours. Repeated freeze thawing of mRNA preparations is not recommended due to the potential for mRNA and/or LNP instability.

SUMMARY OF THE INVENTION

The present invention provides, among other things, a dry powder (i.e., spray-dried) formulation of mRNA encapsulated with lipid based nanoparticles for more efficient mRNA delivery and more efficacious mRNA therapy. Prior to the present invention, one of the challenges of spray-drying lipid nanoparticle-encapsulated mRNA arose from the fact that both mRNA and the lipid nanoparticle components are structurally labile at the high temperatures and/or pressures needed for adequate spray-drying. For example, an inlet temperature of a spray-dryer ranges between 80° C. to 98° C. Lipids tend to melt and/or aggregate at the high inlet temperature at or near the spray nozzle. This causes hindrance to the flow of the formulation through the nozzle into the drying chamber, disrupts uniform dispersion of the spray and produces undesirable particle characteristics and poor yield. The present invention has unexpectedly solved this problem with the addition of a polymer to the mRNA and lipid nanoparticle mixture before subjecting the mixture to the spray-drying process. As described herein, the inventors observed that adding a polymer to an mRNA and lipid mixture effectively prevents aggregation of lipid nanoparticles and facilitates dry powder formation of fine particles containing mRNA-loaded lipid nanoparticles suitable for inhalation.

More surprisingly, despite the extremely unstable nature of mRNA, dry powder formulations prepared according to the present invention, even under high temperatures and/or high pressures associated with spray-drying, are stable and able to maintain a high degree of mRNA integrity even after long term storage at various temperatures. In addition, a dry powder formulation prepared according to the present invention is also characterized with high LNP encapsulation efficiency of mRNA, resulting in high cellular delivery of mRNA. Therefore, the present invention fulfils a long-standing need in the mRNA therapy field for a stable dry powder form of mRNA therapeutic, which can easily be stored, transferred, and dispensed. Further, the dry powder formulations of mRNA according to the present invention can be administered as dry powder to a patient, e.g. in metered doses or weighed out and reconstituted in single-use amounts, without the need for freezing single-use aliquots of liquid.

In one aspect, the present invention provides a dry powder formulation for delivery of messenger RNA (mRNA) containing a plurality of spray-dried particles comprising mRNA encoding a protein or a peptide, one or more lipids, and one or more polymers.

In another aspect, the present invention provides a dry powder formulation for delivery of messenger RNA (mRNA) containing a plurality of spray-dried particles comprising one or more lipid nanoparticles (LNPs) encapsulating mRNA encoding a peptide or polypeptide, and one or more polymers.

In still another aspect, the present invention provides a dry powder formulation for delivery of messenger RNA (mRNA) containing a plurality of spray-dried particles comprising one or more nanoparticles encapsulating mRNA encoding a peptide or polypeptide, the nanoparticles comprising one or more lipids, and one or more polymers.

In yet another aspect, the present invention provides a dry powder formulation for delivery of cystic fibrosis conductance regulator (CFTR) messenger RNA (mRNA) containing a plurality of spray-dried particles comprising mRNA encoding a CFTR protein, one or more lipids, and one or more polymers. In some embodiments, the one or more lipids form one or more lipid nanoparticles (LNPs) encapsulating the mRNA encoding the CFTR protein. In some embodiments, the one or more lipids and the one or more polymers form one or more nanoparticles encapsulating the mRNA encoding the CFTR protein.

As used in this application, lipid nanoparticles (LNPs) encompass nanoparticles formed with lipids, as well as nanoparticles formed with both lipids and polymers. In some embodiments, nanoparticles formed with both lipids and polymers are referred to as lipid-polymer nanoparticles.

In some embodiments, mRNA (e.g., CFTR mRNA) has an integrity of 80% or greater, 85% or greater, 90% or greater, 95% or greater, 96% or greater, 97% or greater, 98% or greater, or 99% or greater. In some embodiments, mRNA (e.g., CFTR mRNA) has an integrity of 90% or greater. In some embodiments, mRNA (e.g., CFTR mRNA) has an integrity of 95% or greater. In some embodiments, mRNA (e.g., CFTR mRNA) has an integrity of 98% or greater.

In some embodiments, the mRNA maintains an integrity of 90% or greater upon storage at or under room temperature for 6 months or longer. In some embodiments, the mRNA maintains an integrity of 95% or greater upon storage at or under room temperature for 6 months or longer. In some embodiments, the mRNA maintains an integrity of 98% or greater upon storage at or under room temperature for 6 months or longer.

In some embodiments, the mRNA maintains integrity of or greater than 90% after spray-drying and storage at or under room temperature for three months or longer. In some embodiments, the mRNA maintains integrity of or greater than 90% after spray-drying and storage at or under room temperature for six months or longer. In some embodiments, the mRNA maintains integrity of or greater than 90% after spray-drying and storage at or under room temperature for nine months or longer. In some embodiments, the mRNA maintains integrity of or greater than 90% after spray-drying and storage at or under room temperature for twelve months or longer. In some embodiments, the mRNA maintains integrity of or greater than 90% after spray-drying and storage at or under 4° C. for three months or longer. In some embodiments, the mRNA maintains integrity of or greater than 90% after spray-drying and storage at or under 4° C. for six months or longer. In some embodiments, the mRNA maintains integrity of or greater than 90% after spray-drying and storage at or under 4° C. or lower for nine months or longer. In some embodiments, the mRNA maintains integrity of or greater than 90% after spray-drying and storage at or under 4° C. for twelve months or longer. In some embodiments, the mRNA maintains integrity of or greater than 95% after storage at or under room temperature for 3 months or longer, 6 months or longer, 9 months or longer, or 12 months or longer. In some embodiments, the mRNA maintains integrity of or greater than 95% after storage at or under 4° C. for 3 months or longer, 6 months or longer, 9 months or longer, or 12 months or longer.

In some embodiments, at least 5%, 10%, 15%, 20%, 25%, 30%, 35%, 40%, 45%, or 50% of the plurality of spray-dried particles are a fraction of fine particles. In some embodiments, at least 20% of the plurality of spray-dried particles are a fraction of fine particles.

In some embodiments, the fine particles have a volume median diameter of 5 micrometers or less. In some embodiments, the fine particles have a volume median diameter of 4 micrometers or less. In some embodiments, the fine particles have a volume median diameter of 3 micrometers or less. In some embodiments, the fine particles have a volume median diameter of 2 micrometers or less. In some embodiments, the fine particles have a volume median diameter of 1 micrometer or less.

In some embodiments, the plurality of spray-dried particles has an average sphericity of greater than 0.6, greater than 0.7, greater than 0.8, or greater than 0.9. In some embodiments, the plurality of spray-dried particles has a Z-average size of less than 3,000 nm, 2,500 nm, 2,000 nm, 1,500 nm, 1,000 nm, or 500 nm.

In some embodiments, the plurality of spray-dried particles comprise a residual moisture content of less than 20%, less than 18%, less than 16%, less than 14%, less than 12%, less than 10%, less than 9%, less than 8%, less than 7%, less than 6%, less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, or less than 0.1%.

In some embodiments, the dry powder formulation is inhalable. In some embodiments, the dry-powder formulation is inhaled as a dry powder in a metered dose inhaler. In some embodiments, the dry-power formulation is reconstituted with a diluent and administered by nebulization.

In some embodiments, the one or more polymers constitute at least 10%, at least 15%, at least 20%, at least 25%, at least 30%, at least 35%, at least 40%, at least 45%, or at least 50% of the combined weight of the lipids and polymers. In some embodiments, the one or more polymers constitute about 10-90%, 10-80%, 10-70%, 10-60%, 10-50%, 10-40%, 10-30%, 10-20%, 15-20%, 15-25%, 15-30%, 15-35%, 15-40%, 15-45%, 15-50%, 15-55%, 15-60%, 15-65%, 15-70%, 15-75%, 15-80%, or 15-90% of the combined weight of the lipids and polymers. In some embodiments, the one or more polymers constitute no more than 90%, 80%, 70%, 60%, 55%, 50%, 45%, 40%, 35%, 30%, 25%, or 20% of the combined weight of the lipids and polymers.

In some embodiments, the one or more polymers constitute at least 50% of the total weight of dry powder. In some embodiments, the one or more polymers constitute at least 40% of the total weight of dry powder. In some embodiments, the one or more polymers constitute at least 30% of the total weight of dry powder. In some embodiments, the one or more polymers constitute at least 20% of the total weight of dry powder. In some embodiments, the one or more polymers constitute at least 15% of the total weight of dry powder. In some embodiments, the one or more polymers constitute at least 12% of the total weight of dry powder. In some embodiments, the one or more polymers constitute at least 10% of the total weight of dry powder. In some embodiments, the one or more polymers constitute at least 9% of the total weight of dry powder. In some embodiments, the one or more polymers constitute at least 8% of the total weight of dry powder. In some embodiments, the one or more polymers constitute at least 7% of the total weight of dry powder. In some embodiments, the one or more polymers constitute at least 6% of the total weight of dry powder. In some embodiments, the one or more polymers constitute at least 5% of the total weight of dry powder.

In some embodiments, the one or more polymers are selected from the group consisting of chitosan, poly(lactic acid) (PLA), poly(lactic-co-glycolic acid) (PLGA), poly(q-caprolactone (PCL), poly amido amines, polyesters, polycarbonates, poly(hydroxyalkyl L-asparagine), poly(hydroxyalkyl L-glutamine), poly(2-alkyloxazoline) acrylates, modified acrylates and polymethacrylate based polymers, poly-N-(2-hydroxyl-propyl)methacrylamide, poly-2-(methacryloyloxy)ethyl phosphorylcholines, poly(2-(methacryloyloxy)ethyl phosphorylcholine), and poly(dimethylaminoethyl methylacrylate) (pDMAEMA).

In some embodiments, the one or more polymers include a polymethacrylate based polymer. In some embodiments, the one or more polymers include Eudragit EPO.

In some embodiments, the one or more LNPs encapsulating mRNA (also referred to as mRNA-loaded LNPs) have a lipid:mRNA (N/P) ratio ranging from 1-20, 1-15, 1-10, 2-8, 2-6, or 2-4. In some embodiments, the one or more mRNA-loaded lipid nanoparticles have a lipid:mRNA (N/P) ratio ranging from 1 to 20. In some embodiments, the one or more mRNA-loaded lipid nanoparticles have a lipid:mRNA (N/P) ratio ranging from 1 to 18. In some embodiments, the one or more mRNA-loaded lipid nanoparticles have a lipid: mRNA (N/P) ratio ranging from 1 to 16. In some embodiments, the one or more mRNA-loaded lipid nanoparticles have a lipid:mRNA (N/P) ratio ranging from 1 to 14. In some embodiments, the one or more mRNA-loaded lipid nanoparticles have a lipid:mRNA (N/P) ratio ranging from 1 to 12. In some embodiments, the one or more mRNA-loaded lipid nanoparticles have a lipid:mRNA (N/P) ratio ranging from 1 to 10. In some embodiments, the one or more mRNA-loaded lipid nanoparticles have a lipid:mRNA (N/P) ratio ranging from 1 to 8. In some embodiments, the one or more mRNA-loaded lipid nanoparticles have a lipid:mRNA (N/P) ratio ranging from 1 to 6. In some embodiments, the one or more mRNA-loaded lipid nanoparticles have a lipid:mRNA (N/P) ratio ranging from 2 to 20. In some embodiments, the one or more mRNA-loaded lipid nanoparticles have a lipid:mRNA (N/P) ratio ranging from 2 to 16. In some embodiments, the one or more mRNA-loaded lipid nanoparticles have a lipid:mRNA (N/P) ratio ranging from 2 to 12. In some embodiments, the one or more mRNA-loaded lipid nanoparticles have a lipid:mRNA (N/P) ratio ranging from 2 to 8. In some embodiments, the one or more mRNA-loaded lipid nanoparticles have a lipid:mRNA (N/P) ratio ranging from 2 to 6. In some embodiments, the one or more mRNA-loaded lipid nanoparticles have a lipid:mRNA (N/P) ratio ranging from 2 to 4. In some embodiments, the one or more mRNA-loaded lipid nanoparticles have a lipid:mRNA (N/P) ratio ranging from 4 to 20. In some embodiments, the one or more mRNA-loaded lipid nanoparticles have a lipid:mRNA (N/P) ratio ranging from 4 to 16. In some embodiments, the one or more mRNA-loaded lipid nanoparticles have a lipid:mRNA (N/P) ratio ranging from 4 to 14. In some embodiments, the one or more mRNA-loaded lipid nanoparticles have a lipid:mRNA (N/P) ratio ranging from 4 to 12. In some embodiments, the one or more mRNA-loaded lipid nanoparticles have a lipid:mRNA (N/P) ratio ranging from 4 to 10. In some embodiments, the one or more mRNA-loaded LNPs have a lipid:mRNA (N/P) ratio of 2 or 4. In some embodiments, the one or more mRNA-loaded LNPs have a lipid:mRNA (N/P) ratio of 2. In some embodiments, the one or more mRNA-loaded LNPs have a lipid:mRNA (N/P) ratio of 4.

In some embodiments, the one or more mRNA-loaded lipid nanoparticles have an encapsulation efficiency of 70% or greater. In some embodiments, the one or more mRNA-loaded lipid nanoparticles have an encapsulation efficiency of 75% or greater. In some embodiments, the one or more mRNA-loaded lipid nanoparticles have an encapsulation efficiency of 80% or greater. In some embodiments, the one or more mRNA-loaded lipid nanoparticles have an encapsulation efficiency of 85% or greater. In some embodiments, the one or more mRNA-loaded lipid nanoparticles have an encapsulation efficiency of 90% or greater. In some embodiments, the one or more mRNA-loaded lipid nanoparticles have an encapsulation efficiency of 92% or greater. In some embodiments, the one or more mRNA-loaded lipid nanoparticles have an encapsulation efficiency of 94% or greater. In some embodiments, the one or more mRNA-loaded lipid nanoparticles have an encapsulation efficiency of 95% or greater. In some embodiments, the one or more mRNA-loaded lipid nanoparticles have an encapsulation efficiency of 96% or greater. In some embodiments, the one or more mRNA-loaded lipid nanoparticles have an encapsulation efficiency of 97% or greater. In some embodiments, the one or more mRNA-loaded lipid nanoparticles have an encapsulation efficiency of 98% or greater.

In some embodiments, the one or more lipids comprise a cationic lipid. In some embodiments, the cationic lipid is selected from the group consisting of C12-200, DOTAP (1,2-dioleyl-3-trimethytammonium propane), DODAP (1,2-dioleyl-3-dimethylammonium propane), DOTMA (1,2-di-O-octadecenyl-3-trimethylammonium propane), DLinDMA, DLin-KC2-DMA, HGT4003, cKK-E12, ICE, and combinations thereof.

In some embodiments, the one or more mRNA-loaded lipid nanoparticles comprise one or more cationic lipids. In some embodiments, the one or more cationic lipids comprises an ionizable cationic lipid. In some embodiments, the one or more cationic lipids comprises the cationic lipid C12-200. In some embodiments, the one or more cationic lipids comprises the cationic lipid DOTAP (1,2-dioleyl-3-trimethytammonium propane). In some embodiments, the one or more cationic lipids comprises the cationic lipid DODAP (1,2-dioleyl-3-dimethylammonium propane). In some embodiments, the one or more cationic lipids comprises the cationic lipid DOTMA (1,2-di-O-octadecenyl-3-trimethylammonium propane). In some embodiments, the one or more cationic lipids comprises the cationic lipid DLinDMA. In some embodiments, the one or more cationic lipids comprises the cationic lipid DLin-KC2-DMA. In some embodiments, the one or more cationic lipids comprises the cationic lipid HGT-5000. In some embodiments, the one or more cationic lipids comprises the cationic lipid HGT-5001. In some embodiments, the one or more cationic lipids comprises the cationic lipid HGT-5002. In some embodiments, the one or more cationic lipids comprises the cationic lipid cKK-E12. In some embodiments, the one or more cationic lipids comprises the cationic lipid OF-02. In some embodiments, the one or more cationic lipids comprises the cationic lipid Target 23. In some embodiments, the one or more cationic lipids comprises the cationic lipid Compound 1. In some embodiments, the one or more cationic lipids comprises the cationic lipid Compound 2. In some embodiments, the one or more cationic lipids comprises the cationic lipid Compound 3. In some embodiments, the one or more cationic lipids comprises the cationic lipid HGT4001. In some embodiments, the one or more cationic lipids comprises the cationic lipid HGT4002. In some embodiments, the one or more cationic lipids comprises the cationic lipid HGT4003. In some embodiments, the one or more cationic lipids comprises the cationic lipid HGT4004. In some embodiments, the one or more cationic lipids comprises the cationic lipid HGT4005. In some embodiments, the one or more cationic lipids comprises the cationic lipid 18:1 Carbon tail-ribose lipid. In some embodiments, the one or more cationic lipids comprises the cationic lipid ICE.

In some embodiments, the cationic lipid constitutes about 25-50% of the total lipids in LNPs by molar.

In some embodiments, the one or more lipids comprise a PEG-modified lipid. In some embodiments, the one or more mRNA-loaded lipid nanoparticles comprise one or more PEG-modified lipids. In some embodiments, the one or more PEG-modified lipids comprise a poly(ethylene) glycol chain of up to 5 kDa in length covalently attached to a lipid comprising one or more alkyl chains of C6-C20 in length. In some embodiments, the one or more PEG-modified lipids constitute up to 20%, 15%, 12%, 10%, 9%, 8%, 7%, 6%, 5%, 4%, 3%, 2% or 1% of the total lipids in LNPs by molar. In some embodiments, the PEG-modified lipid constitutes about 1-15% of the total lipids in LNPs by molar. In some embodiments, the PEG-modified lipid constitutes at least 1%, 2%, 3%, 4%, 5%, 6%, 8%, 10%, or 12% of the total lipids in LNPs by molar.

In some embodiments, suitable LNPs according to the present invention are two-lipid component LNPs.

In some embodiments, the one or more lipids do not include a neutral lipid or a cholesterol-based lipid.

In some embodiments, the one or more lipids further comprise a neutral lipid and/or a cholesterol-based lipid. In some embodiments, the one or more lipids further comprise a neutral lipid.

In some embodiments, suitable LNPs according to the present invention are three-lipid component LNPs.

In some embodiments, a dry powder formulation according to the present invention further contains at least one sugar. In some embodiments, the sugar is selected from the group consisting of monosaccharides, disaccharides, polysaccharides, glucose, fructose, galactose, mannose, sorbose, lactose, sucrose, cellobiose, trehalose, raffinose, starch, dextran, maltodextrin, cyclodextrins, inulin, xylitol, sorbitol, lactitol, mannitol, and combination thereof. In some embodiments, the sugar is mannitol. In some embodiments, the sugar constitutes less than 30%, 25%, 20%, 15%, 10%, or 5% of total weight.

In some embodiments, a dry powder formulation according to the present invention further comprises a pharmaceutically acceptable excipient selected from the group consisting of esters, urethanes, phosphoesters, phosphazenes, amino acids, collagen, chitosan, polysaccharides, albumin, surfactants, buffers, salts, and combinations thereof.

In some embodiments, a suitable surfactant is selected from the group consisting of CHAPS (3-[(3-Cholamidopropyl)dimethylammonio]-1-propanesulfonate), phospholipids, phosphatidylserine, phosphatidylethanolamine, phosphatidylcholine, sphingomyelins, Octaethylene glycol monododecyl ether, Pentaethylene glycol monododecyl ether, Triton X-100, Cocamide monoethanolamine, Cocamide diethanolamine, Glycerol monostearate, Glycerol monolaurate, Sorbitan moonolaureate, Sorbitan monostearate, Tween 20, Tween 40, Tween 60, Tween 80, Alkyl polyglucosides, and a poloxamer (e.g., poloxamer 407). In some embodiments, a suitable surfactant is poloxamer.

In some embodiments, a dry powder formulation according to the present invention further contains a pharmaceutically acceptable excipient. In some embodiments, a pharmaceutically acceptable excipient is selected from the group consisting of esters, urethanes, phosphoesters, phosphazenes, amino acids, collagen, chitosan, polysaccharides, albumin, surfactants, buffers, salts, and combination thereof.

In some embodiments, a dry powder formulation according to the present invention contains a surfactant. In some embodiments, the surfactant is selected from the group consisting of CHAPS (3-[(3-Cholamidopropyl)dimethylammonio]-1-propanesulfonate), phospholipids, phosphatidylserine, phosphatidylethanolamine, phosphatidylcholine, sphingomyelins, Octaethylene glycol monododecyl ether, Pentaethylene glycol monododecyl ether, Triton X-100, Cocamide monoethanolamine, Cocamide diethanolamine, Glycerol monostearate, Glycerol monolaurate, Sorbitan moonolaureate, Sorbitan monostearate, Tween 20, Tween 40, Tween 60, Tween 80, Alkyl polyglucosides, and copolymers. In some embodiments, the surfactant is a poloxamer. In some embodiments, the surfactant is poloxamer a triblock copolymer consisting of a central hydrophobic block of polypropylene glycol flanked by two hydrophilic blocks of polyethylene glycol (PEG). In some embodiments, the surfactant is poloxamer 407.

In some embodiments, the mRNA constitutes up to 10% of the total weight of dry powder. In some embodiments, the mRNA constitutes up to 9% of the total weight of dry powder. In some embodiments, the mRNA constitutes up to 8% of the total weight of dry powder. In some embodiments, the mRNA constitutes up to 7% of the total weight of dry powder. In some embodiments, the mRNA constitutes up to 6% of the total weight of dry powder. In some embodiments, the mRNA constitutes up to 5% of the total weight of dry powder. In some embodiments, the mRNA constitutes up to 4% of the total weight of dry powder. In some embodiments, the mRNA constitutes up to 3% of the total weight of dry powder. In some embodiments, the mRNA constitutes up to 2% of the total weight of dry powder. In some embodiments, the mRNA constitutes 1-10% of the total weight of dry powder. In some embodiments, the mRNA constitutes 1-6% of the total weight of dry powder. In some embodiments, the mRNA constitutes 1-5% of the total weight of dry powder. In some embodiments, the mRNA constitutes 1-4% of the total weight of dry powder. In some embodiments, the mRNA constitutes 1-3% of the total weight of dry powder. In some embodiments, the mRNA constitutes 2-10% of the total weight of dry powder. In some embodiments, the mRNA constitutes 2-9% of the total weight of dry powder. In some embodiments, the mRNA constitutes 2-8% of the total weight of dry powder. In some embodiments, the mRNA constitutes 2-7% of the total weight of dry powder. In some embodiments, the mRNA constitutes 2-6% of the total weight of dry powder. In some embodiments, the mRNA constitutes 2-5% of the total weight of dry powder. In some embodiments, the mRNA is unmodified. In some embodiments, the mRNA contains one or more modified nucleotides.

In some embodiments, the mRNA encodes a peptide. In some embodiments, the mRNA encodes a therapeutic protein. In some embodiments, the therapeutic protein is CFTR.

In some embodiments, the CFTR mRNA constitutes about 1-20%, 1-15%, 1-10%, 1-8%, 1-6%, 1-5%, 5-15%, or 5-10% of the total weight of the spray-dried particles. In some embodiments, the CFTR mRNA constitutes about 1%, 2%, 3%, 4%, 5%, 7.5%, 10%, 12.5%, or 15% of the total weight of the spray-dried particles.

In another aspect, the present invention provides a method of delivering cystic fibrosis conductance regulator (CFTR) messenger RNA (mRNA) for in vivo expression comprising a step of administering to a subject in need thereof a dry powder formulation described herein. In some embodiments, a dry powder formulation described herein is administered by pulmonary delivery. In some embodiments, a dry powder formulation is administered by inhalation.

In a further aspect, the present invention provides a method of delivering cystic fibrosis conductance regulator (CFTR) messenger RNA (mRNA) for in vivo expression comprising steps of: reconstituting a dry powder formulation of described herein into a liquid solution; and administering to a subject in need thereof the reconstituted liquid solution. In some embodiments, the reconstituted liquid solution is administered by nebulization. In some embodiments, the subject is suffering from cystic fibrosis.

In another aspect, the present invention provides a method for manufacturing a dry powder formulation including providing a mixture comprising an mRNA, one or more lipids and a polymer; and spray-drying the mixture to form a plurality of particles.

In some embodiments, the one or more lipids are first mixed with the mRNA to form mRNA-loaded lipid nanoparticles before adding the polymer.

In some embodiments, a method according to the invention further includes adding to the mixture one or more excipients prior to spray drying.

In some embodiments, the plurality of spray dried particles is characterized by one or more of the following: a) less than 10% moisture content; b) a fraction of fine particles with a volume median diameter less than 5 micrometers; c) Z-average size range of 10-3000 nm; d) N/P ratio range from 1 to 20; e) mRNA encapsulation efficiency greater than 80%; and f) mRNA integrity greater than 95%.

In yet another aspect, the present invention provides a method of delivering mRNA in vivo comprising administering to a subject in need thereof a dry powder formulation described herein. In some embodiments, the dry powder formulation is administered via oral, nasal, tracheal, pulmonary or rectal routes. In some embodiments, the dry powder formulation is administered by inhalation. In some embodiments, the dry powder formulation is administered by intranasal spray. In some embodiments, the formulation is administered by a metered-dose inhaler. In some embodiments, the formulation is administered by a nebulizer.

In still another aspect, the present invention provides a method of delivering cystic fibrosis conductance regulator (CFTR) messenger RNA (mRNA) for in vivo expression comprising a step of administering to a subject in need thereof a dry powder formulation described herein.

In still another aspect, the present invention provides a method of treating a disease or disorder in a patient by administering to the patient an effective dose of mRNA in a dry powder formulation described herein. In some embodiments, the disease or disorder is selected from cystic fibrosis; asthma; COPD; emphysema; primary ciliary dyskinesia (CILD1) with or without situs inversus, or Kartagener syndrome; pulmonary fibrosis; Birt-Hogg-Dube syndrome; hereditary hemorrhagic telangiectasia; alpha-1 antitrypsin deficiency; Cytochrome b positive granulomatous diseases (CGD, X-lined); Cytochrome b positive granulomatous diseases, autosomal recessive; surfactant deficiency diseases, Pulmonary Surfactant Metabolism Dysfunction 1, Pulmonary Surfactant Metabolism Dysfunction 2, Pulmonary Surfactant Metabolism Dysfunction 3; Respiratory distress syndrome of prematurity; tuberculous tuberculosis, lung viral diseases, including influenza, Respiratory Syncytial Virus (RSV).

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

BRIEF DESCRIPTION OF THE DRAWINGS

The drawings are for illustration purposes only, not for limitation.

FIG. 16A1-A6 depicts exemplary capillary electrophoresis chromatographs illustrating integrity of CFTR mRNA after spray-drying. FIG. 16A1-A3 depicts control CFTR mRNA which was neither spray dried nor encapsulated, while FIG. 16A4-A6 depicts the CFTR mRNA extracted from the spray-dried formulation.

DEFINITIONS

Figure 1:
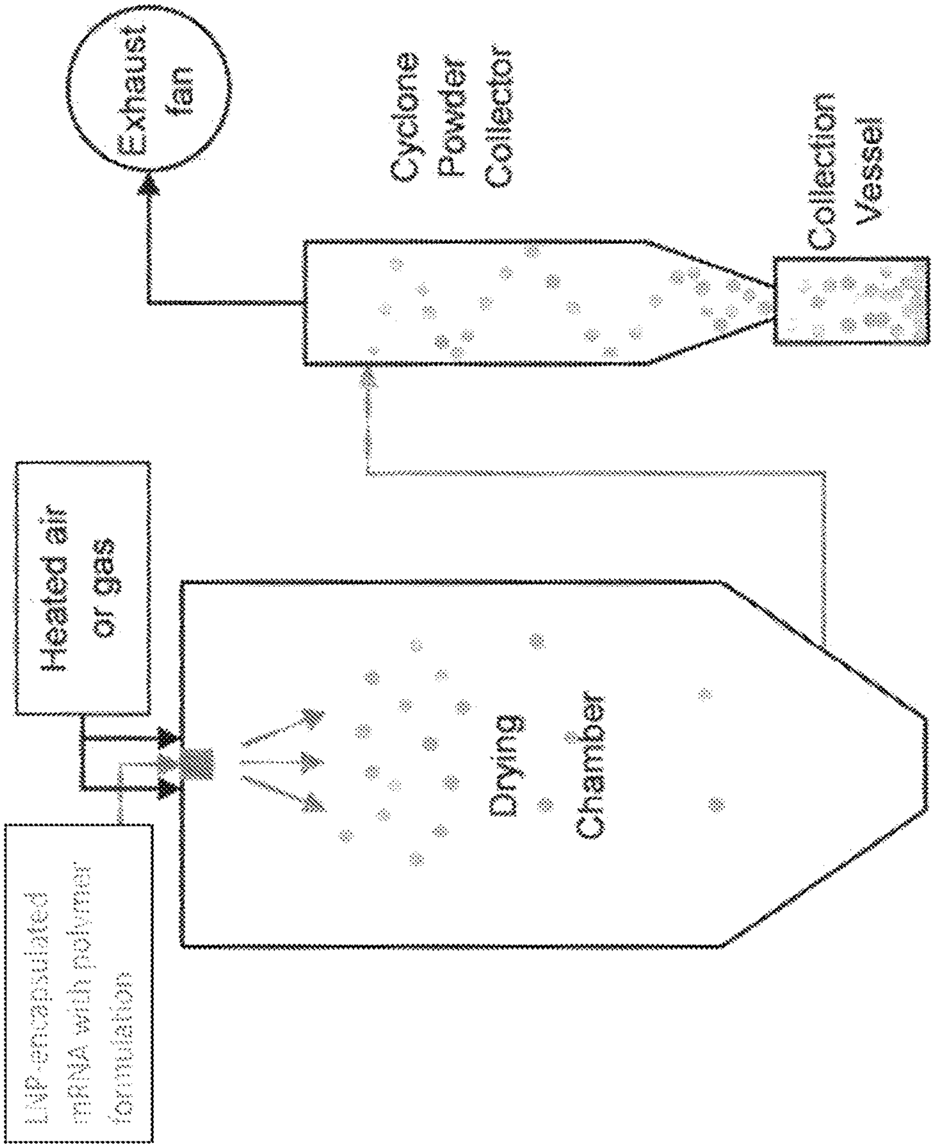
FIG. 1 shows an exemplary graphical illustration of the spray-drying technique of mRNA formulations.

In order for the present invention to be more readily understood, certain terms are first defined below. Additional definitions for the following terms and other terms are set forth throughout the specification.

Animal: As used herein, the term “animal” refers to any member of the animal kingdom. In some embodiments, “animal” refers to humans, at any stage of development. In some embodiments, “animal” refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term “approximately” or “about,” as applied to one or more values of interest, refers to a value that is similar to a stated reference value. In certain embodiments, the term “approximately” or “about” refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Delivery: As used herein, the term “delivery” encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery").

Encapsulation: As used herein, the term "encapsulation," or grammatical equivalent, refers to the process of confining an individual mRNA molecule within a nanoparticle.

Expression: As used herein, "expression" of a nucleic acid sequence refers to translation of an mRNA into a polypeptide, assemble multiple polypeptides into an intact protein (e.g., enzyme) and/or post-translational modification of a polypeptide or fully assembled protein (e.g., enzyme). In this application, the terms "expression" and "production," and grammatical equivalent, are used inter-changeably.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Local distribution or delivery: As used herein, the terms "local distribution," "local delivery," or grammatical equivalent, refer to tissue specific delivery or distribution. Typically, local distribution or delivery requires a protein (e.g., enzyme) encoded by mRNAs be translated and expressed intracellularly or with limited secretion that avoids entering the patient's circulation system.

Messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

N/P Ratio: As used herein, the term "N/P ratio" refers to a molar ratio of positively charged molecular units in the cationic lipids in a lipid nanoparticle relative to negatively charged molecular units in the mRNA encapsulated within that lipid nanoparticle. As such, N/P ratio is typically calculated as the ratio of moles of amine groups in cationic lipids in a lipid nanoparticle relative to moles of phosphate groups in mRNA encapsulated within that lipid nanoparticle.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: As used herein, the term "pharmaceutically acceptable" refers to substances that, within the scope of sound medical judgment, are suitable for use in contact with the tissues of human beings and animals without excessive toxicity, irritation, allergic response, or other problem or complication, commensurate with a reasonable benefit/risk ratio.

Subcutaneous administration: As used herein, the term "subcutaneous administration" or "subcutaneous injection" refers to a bolus injection into the subcutis, which is the tissue layer between the skin and the muscle.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides stable dry powder formulations containing mRNA loaded lipid nanoparticles (mRNA-LNP) for therapeutic use. In particular, the present invention provides a dry powder formulation for delivery of mRNA comprising a plurality of spray-dried particles, each spray-dried particle comprising one or more mRNA loaded lipid nanoparticles and a polymer, and methods of making and using the same.

Various aspects of the invention are described in detail in the following sections. The use of sections is not meant to limit the invention. Each section can apply to any aspect of the invention. In this application, the use of "or" means "and/or" unless stated otherwise.

Spray-Drying Process

Various spray-drying processes may be used to practice the present invention. The process involves, in general, removal of moisture from a composition by passing a liquid form of the composition through an apparatus; a simplified diagrammatic depiction is provided as FIG. 1. In brief, a liquid formulation comprising the composition of interest is passed through a narrow inlet spray 'atomizer' nozzle into a first chamber, which is the drying chamber. Usually the liquid formulation is passed in a steady stream. The liquid formulation is sprayed as tiny droplets into the drying chamber. A stream of heated air or gas is also led into the drying chamber to form an air current. Passage of the formulation through this heated current disperses the incoming droplets, dries them into the solid particulate form. This product is led into a second chamber by flow through a connector or pipe. The second chamber is the cyclone powder collector. Here, the air circulation generates a cyclone, and the powder particles are collected via a vortex stream into a collection vessel attached to the outlet end. The cyclone chamber is attached to an exhaust fan, which helps cool the components. The inlet and outlet temperatures are operator adjustable. The respective inlet and outlet temperatures, the chamber temperatures, the liquid feed flow rate (aspirator %), pressure, nature of the heated air current and most importantly, the composition of the liquid feed are suitably adjusted for optimal drying of any particulate matter.

In some embodiments, the inlet temperature is adjustable within a range of 40° C. to 200° C. In some embodiments, the outlet temperature ranges between 20-70° C. The relative pressure of the pump and the aspirator is also operator adjustable. In some embodiments, for spray-drying mRNA-lipid nanoparticle, the inlet temperature is adjusted between 70° C. and 200° C. In some embodiments, the inlet temperature is adjusted between 80° C. and 200° C. In some embodiments, the inlet temperature is adjusted between 90° C. and 200° C. In some embodiments, the inlet temperature is adjusted between 95° C. and 180° C. In some embodiments, the inlet temperature is adjusted between 95° C. and 160° C. In some embodiments, the inlet temperature is adjusted between 90° C. and 150° C. In some embodiments, the inlet temperature is adjusted between 90° C. and 120° C. In some embodiments the inlet temperature is adjusted between 90° C. and 100° C. In some embodiments, the inlet temperature is 70° C., 75° C., 80° C., 85° C., 90° C., 95° C., or 100° C.

The aspirator percentage into the drying chamber is typically adjusted between 50% and 100%. In some embodiments, the aspirator percentage into the drying chamber is adjusted between 50% and 100%. In some embodiments, the aspirator percentage into the drying chamber is adjusted between 60% and 100%. In some embodiments, the aspirator percentage into the drying chamber is adjusted between 70% and 100%. In some embodiments, the aspirator percentage into the drying chamber is adjusted between 80% and 100%. In certain embodiments the aspirator percentage is adjusted between 80% and 90%. In some embodiments, the aspirator percentage is or less than 100%, or, is or less than 95%, or, is or less than 90%, or is or less than 85%, or is or less than 80%.

In some embodiments, the liquid flow through the inlet into the drying chamber is adjusted by a pump, set at a range between 10%-50%. In some embodiments, the pump is set at a range between 20% and 40%. In some embodiments, the pump is set at a range between 10% and 30%. In some embodiments, the pump is set at a range between 20% and 30%. In some embodiments, the pump is set at a range between 30% and 50%. In some embodiments, the pump is set at 25%.

In some embodiments, the outlet temperature ranges between 20° C. to 70° C. In some embodiments, the outlet temperature is between 30° C. to 60° C. In some embodiments, the outlet temperature is between 20° C. to 50° C. In some embodiments, the outlet temperature is between 30° C. to 50° C. In some embodiments, the outlet temperature is between 40° C. to 50° C. In some embodiments, the outlet temperature is between 45° C. and 50° C.

Spray drying of mRNA-LNP can be carried out using any suitable spray-drying device. As is known to a person of ordinary skill in the art, a variety of spray-drying instruments are commercially available and can be used to practice the present invention. Exemplary commercially available devices suitable for the present invention include, but are not limited to the following: Mini Spray Dryer B-290; Nano Spray Dryer B-90 (manufactured by Buchi); Anhydro MicraSpray Dryer GMP; Anhydro MicraSpray Dryer Aseptic series (manufactured by SPX FLOW); MDL-50 and MDL-015 (manufactured by Fujisaki Electric); Versatile Mini Sprayer Dryer GAS410 (manufactured by Yamato Scientific America); LSD-1500 Mini spray dryer, MSD-8 Multi-functional laboratory spray dryer; PSD-12 Precision pharmacy spray dryer; (manufactured by Changzhou Xiandao Drying Equipment Co. Ltd); TALL FORM DRYER™; Multi-Stage Dryer; COMPACT DRYER™; FILTERMAT Spray Dryer; VERSATILE-SD™; Fluidized Spray Dryer; MOBILE MINOR™; SDMICRO™; PRODUCTION MINOR™ (manufactured by GEA Process Engineering) and many others. Convenient scale up from laboratory scale to industrial manufacturing scale is also available from several of these manufacturers.

Spray-Drying mRNA-Loaded Nanoparticles

According to the present invention, spray drying mRNA-loaded nanoparticles involves adding a polymer to an mRNA and lipids mixture. In some embodiments, lipids and mRNA are mixed first to pre-form mRNA-loaded lipid nanoparticles before adding the polymer. In some embodiments, the lipids, mRNA and polymer are mixed at the same time before spray drying. In some embodiments, a method according to the invention further includes adding to the mixture one or more excipients prior to spray drying.

mRNA-Loaded Lipid Nanoparticles

Any desired lipids may be mixed at any ratios suitable for encapsulating mRNAs. In some embodiments, a suitable lipid mixture contains cationic lipids, non-cationic lipids, and/or PEGylated lipids. In some embodiments, a suitable lipid mixture also contains cholesterol-based lipids. In some embodiments, an mRNA-LNP is first formed by mixing the mRNA and lipids before mixing with a polymer or other excipients and subjecting the mixtures to spray drying.

In some embodiments, mRNA-LNPs are formed by mixing an mRNA solution with a lipid solution, wherein the mRNA solution and/or the lipid solution are heated to a pre-determined temperature greater than ambient temperature prior to mixing (see U.S. Pat. No. 9,668,980, entitled "Encapsulation of messenger RNA", the disclosure of which is hereby incorporated in its entirety).

In some embodiments, mRNA-LNPs are formed by combining pre-formed lipid nanoparticles with mRNA (see U.S. Patent Application Publication No. 2018/0153822, the disclosure of which is hereby incorporated by reference).

In some embodiments, encapsulation efficiency of mRNA by the lipid nanoparticle before spray-draying is 70% or greater. In some embodiments, encapsulation efficiency of mRNA by the lipid nanoparticle before spray-drajing is 75% or greater. In some embodiments, encapsulation efficiency of mRNA by the lipid nanoparticle before spray-draying is 80% or greater. In some embodiments, encapsulation efficiency of mRNA by the lipid nanoparticle before spray-draying is 85% or greater. In some embodiments, encapsulation efficiency of mRNA by the lipid nanoparticle before spray-draying is 86% or greater. In some embodiments, encapsulation efficiency of mRNA by the lipid nanoparticle before spray-draying is 87% or greater. In some embodiments, encapsulation efficiency of mRNA by the lipid nanoparticle before spray-draying is 88% or greater. In some embodiments, encapsulation efficiency of mRNA by the lipid nanoparticle before spray-draying is 89% or greater. In some embodiments, encapsulation efficiency of mRNA by the lipid nanoparticle before spray-draying is 90% or greater. In some embodiments, encapsulation efficiency of mRNA by the lipid nanoparticle before spray-draying is 91% or greater. In some embodiments, encapsulation efficiency of mRNA by the lipid nanoparticle before spray-draying is 92% or greater. In some embodiments, encapsulation efficiency of mRNA by the lipid nanoparticle before spray-draying is 93% or greater. In some embodiments, encapsulation efficiency of mRNA by the lipid nanoparticle before spray-draying is 94% or greater. In some embodiments, encapsulation efficiency of mRNA by the lipid nanoparticle before spray-draying is 95% or greater. In some embodiments, encapsulation efficiency of mRNA by the lipid nanoparticle before spray-draying is 96% or greater. In some embodiments, encapsulation efficiency of mRNA by the lipid nanoparticle before spray-draying is 97% or greater. In some embodiments, encapsulation efficiency of mRNA by the lipid nanoparticle before spray-draying is 98% or greater. In some embodiments, encapsulation efficiency of mRNA by the lipid nanoparticle before spray-draying is 99% or greater.

In some embodiments, encapsulation efficiency of mRNA by the LNP, after spray-draying a formulation of a polymer and the LNP-encapsulated mRNA, is 70% or greater. In some embodiments, encapsulation efficiency of mRNA by the LNP, after spray-draying a formulation of a polymer and the LNP-encapsulated mRNA, is 75% or greater. In some embodiments, encapsulation efficiency of mRNA by the LNP, after spray-draying a formulation of a polymer and the LNP-encapsulated mRNA, is 80% or greater. In some embodiments, encapsulation efficiency of mRNA by the LNP, after spray-draying a formulation of a polymer and the LNP-encapsulated mRNA, is 85% or greater. In some embodiments, encapsulation efficiency of mRNA by the LNP, after spray-draying a formulation of a polymer and the LNP-encapsulated mRNA, is 86% or greater. In some embodiments, encapsulation efficiency of mRNA by the LNP, after spray-draying a formulation of a polymer and the LNP-encapsulated mRNA, is 87% or greater. In some embodiments, encapsulation efficiency of mRNA by the LNP, after spray-draying a formulation of a polymer and the LNP-encapsulated mRNA, is 88% or greater. In some embodiments, encapsulation efficiency of mRNA by the LNP, after spray-draying a formulation of a polymer and the LNP-encapsulated mRNA, is 89% or greater. In some embodiments, encapsulation efficiency of mRNA by the LNP, after spray-draying a formulation of a polymer and the LNP-encapsulated mRNA, is 90% or greater. In some embodiments, encapsulation efficiency of mRNA by the LNP, after spray-draying a formulation of a polymer and the LNP-encapsulated mRNA, is 91% or greater. In some embodiments, encapsulation efficiency of mRNA by the LNP, after spray-draying a formulation of a polymer and the LNP-encapsulated mRNA, is 92% or greater. In some embodiments, encapsulation efficiency of mRNA by the LNP, after spray-draying a formulation of a polymer and the LNP-encapsulated mRNA, is 93% or greater. In some embodiments, encapsulation efficiency of mRNA by the LNP, after spray-draying a formulation of a polymer and the LNP-encapsulated mRNA, is 94% or greater. In some embodiments, encapsulation efficiency of mRNA by the LNP, after spray-draying a formulation of a polymer and the LNP-encapsulated mRNA, is 95% or greater. In some embodiments, encapsulation efficiency of mRNA by the LNP, after spray-draying a formulation of a polymer and the LNP-encapsulated mRNA, is 96% or greater. In some embodiments, encapsulation efficiency of mRNA by the LNP, after spray-draying a formulation of a polymer and the LNP-encapsulated mRNA, is 97% or greater. In some embodiments, encapsulation efficiency of mRNA by the LNP, after spray-draying a formulation of a polymer and the LNP-encapsulated mRNA, is 98% or greater. In some embodiments, encapsulation efficiency of mRNA by the LNP, after spray-draying a formulation of a polymer and the LNP-encapsulated mRNA, is 99% or greater.

In some embodiments, encapsulation efficiency of mRNA by the LNP, both before and after spray-draying a formulation of a polymer and the LNP-encapsulated mRNA, is 70% or greater. In some embodiments, encapsulation efficiency of mRNA by the LNP, both before and after spray-draying a formulation of a polymer and the LNP-encapsulated mRNA, is 75% or greater. In some embodiments, encapsulation efficiency of mRNA by the LNP, both before and after spray-draying a formulation of a polymer and the LNP-encapsulated mRNA, is 80% or greater. In some embodiments, encapsulation efficiency of mRNA by the LNP, both before and after spray-draying a formulation of a polymer and the LNP-encapsulated mRNA, is 85% or greater. In some embodiments, encapsulation efficiency of mRNA by the LNP, both before and after spray-draying a formulation of a polymer and the LNP-encapsulated mRNA, is 86% or greater. In some embodiments, encapsulation efficiency of mRNA by the LNP, both before and after spray-draying a formulation of a polymer and the LNP-encapsulated mRNA, is 87% or greater. In some embodiments, encapsulation efficiency of mRNA by the LNP, both before and after spray-draying a formulation of a polymer and the LNP-encapsulated mRNA, is 88% or greater. In some embodiments, encapsulation efficiency of mRNA by the LNP, both before and after spray-draying a formulation of a polymer and the LNP-encapsulated mRNA, is 89% or greater. In some embodiments, encapsulation efficiency of mRNA by the LNP, both before and after spray-draying a formulation of a polymer and the LNP-encapsulated mRNA, is 90% or greater. In some embodiments, encapsulation efficiency of mRNA by the LNP, both before and after spray-draying a formulation of a polymer and the LNP-encapsulated mRNA, is 91% or greater. In some embodiments, encapsulation efficiency of mRNA by the LNP, both before and after spray-draying a formulation of a polymer and the LNP-encapsulated mRNA, is 92% or greater. In some embodiments, encapsulation efficiency of mRNA by the LNP, both before and after spray-draying a formulation of a polymer and the LNP-encapsulated mRNA, is 93% or greater. In some embodiments, encapsulation efficiency of mRNA by the LNP, both before and after spray-draying a formulation of a polymer and the LNP-encapsulated mRNA, is 94% or greater. In some embodiments, encapsulation efficiency of mRNA by the LNP, both before and after spray-draying a formulation of a polymer and the LNP-encapsulated mRNA, is 95% or greater. In some embodiments, encapsulation efficiency of mRNA by the LNP, both before and after spray-draying a formulation of a polymer and the LNP-encapsulated mRNA, is 96% or greater. In some embodiments, encapsulation efficiency of mRNA by the LNP, both before and after spray-draying a formulation of a polymer and the LNP-encapsulated mRNA, is 97% or greater. In some embodiments, encapsulation efficiency of mRNA by the LNP, both before and after spray-draying a formulation of a polymer and the LNP-encapsulated mRNA, is 98% or greater. In some embodiments, encapsulation efficiency of mRNA by the LNP, both before and after spray-draying a formulation of a polymer and the LNP-encapsulated mRNA, is 99% or greater.

In some embodiments, the mass of a formulation of a polymer and an LNP-encapsulated mRNA recovered from a spray-drying step is 10% or greater of the mass of the formulation prior to the spray-drying step. In some embodiments, the mass of a formulation of a polymer and an LNP-encapsulated mRNA recovered from a spray-drying step is 15% or greater of the mass of the formulation prior to the spray-drying step. In some embodiments, the mass of a formulation of a polymer and an LNP-encapsulated mRNA recovered from a spray-drying step is 20% or greater of the mass of the formulation prior to the spray-drying step. In some embodiments, the mass of a formulation of a polymer and an LNP-encapsulated mRNA recovered from a spray-drying step is 25% or greater of the mass of the formulation prior to the spray-drying step. In some embodiments, the mass of a formulation of a polymer and an LNP-encapsulated mRNA recovered from a spray-drying step is 30% or greater of the mass of the formulation prior to the spray-drying step. In some embodiments, the mass of a formulation of a polymer and an LNP-encapsulated mRNA recovered from a spray-drying step is 35% or greater of the mass of the formulation prior to the spray-drying step. In some embodiments, the mass of a formulation of a polymer and an LNP-encapsulated mRNA recovered from a spray-drying step is 40% or greater of the mass of the formulation prior to the spray-drying step. In some embodiments, the mass of a formulation of a polymer and an LNP-encapsulated mRNA recovered from a spray-drying step is 41% or greater of the mass of the formulation prior to the spray-drying step. In some embodiments, the mass of a formulation of a polymer and an LNP-encapsulated mRNA recovered from a spray-drying step is 42% or greater of the mass of the formulation prior to the spray-drying step. In some embodiments, the mass of a formulation of a polymer and an LNP-encapsulated mRNA recovered from a spray-drying step is 43% or greater of the mass of the formulation prior to the spray-drying step. In some embodiments, the mass of a formulation of a polymer and an LNP-encapsulated mRNA recovered from a spray-drying step is 44% or greater of the mass of the formulation prior to the spray-drying step. In some embodiments, the mass of a formulation of a polymer and an LNP-encapsulated mRNA recovered from a spray-drying step is 45% or greater of the mass of the formulation prior to the spray-drying step. In some embodiments, the mass of a formulation of a polymer and an LNP-encapsulated mRNA recovered from a spray-drying step is 46% or greater of the mass of the formulation prior to the spray-drying step. In some embodiments, the mass of a formulation of a polymer and an LNP-encapsulated mRNA recovered from a spray-drying step is 47% or greater of the mass of the formulation prior to the spray-drying step. In some embodiments, the mass of a formulation of a polymer and an LNP-encapsulated mRNA recovered from a spray-drying step is 48% or greater of the mass of the formulation prior to the spray-drying step. In some embodiments, the mass of a formulation of a polymer and an LNP-encapsulated mRNA recovered from a spray-drying step is 49% or greater of the mass of the formulation prior to the spray-drying step. In some embodiments, the mass of a formulation of a polymer and an LNP-encapsulated mRNA recovered from a spray-drying step is 50% or greater of the mass of the formulation prior to the spray-drying step.

In some embodiments, mRNA and lipids are combined with pump systems which maintain the lipid/mRNA (N/P) ratio constant throughout the process and which also afford facile scale-up. In some embodiments, the N/P ratio ranges between 1 to 20. In some embodiments, the N/P ratio is greater than 2, or greater than 3, or greater than 4, or greater than 5, or greater than 6, or greater than 7, or greater than 8, or greater than 9, or greater than 10, or greater than 11, or greater than 12, or greater than 13, or greater than 14, or greater than 15. In some embodiments the N/P ratio is 17, or 18, or 19, or 20.

Suitable mRNA loaded lipid nanoparticles may be made in various sizes. In some embodiments, the size of an mRNA loaded lipid nanoparticles pre-spray drying is determined by the length of the largest diameter of the lipid nanoparticle. In some embodiments, an mRNA loaded lipid nanoparticle has a size pre-spray drying no greater than about 250 nm (e.g., no greater than about 225 nm, 200 nm, 175 nm, 150 nm, 125 nm, 100 nm, 75 nm, or 50 nm). In some embodiments, a suitable liposome has a size ranging from about 10-250 nm (e.g., ranging from about 10-225 nm, 10-200 nm, 10-175 nm, 10-150 nm, 10-125 nm, 10-100 nm, 10-75 nm, or 10-50 nm). In some embodiments, an mRNA loaded lipid nanoparticle has a size pre-spray drying ranging from about 100-250 nm (e.g., ranging from about 100-225 nm, 100-200 nm, 100-175 nm, 100-150 nm). In some embodiments, an mRNA loaded lipid nanoparticle has a size pre-spray drying ranging from about 10-100 nm (e.g., ranging from about 10-90 nm, 10-80 nm, 10-70 nm, 10-60 nm, or 10-50 nm). In a particular embodiment, an mRNA loaded lipid nanoparticle has a size pre-spray drying less than about 100 nm.

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev.

Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Suitable mRNA-loaded lipid nanoparticles contain one or more of cationic lipids, PEGylated lipids, non-cationic lipids, and cholesterol-based lipids.

Cationic Lipids

As used herein, the term "cationic lipids" refers to any of a number of lipid and lipidoid species that have a net positive charge at a selected pH, such as at physiological pH. Several cationic lipids have been described in the literature, many of which are commercially available.

Suitable cationic lipids for use in the compositions and methods of the invention include the cationic lipids as described in International Patent Publication WO 2010/144740, which is incorporated herein by reference. In certain embodiments, the compositions and methods of the present invention include a cationic lipid, (6Z,9Z,28Z,31Z)-heptatriaconta-6,9,28,31-tetraen-19-yl 4-(dimethylamino) butanoate, having a compound structure of:

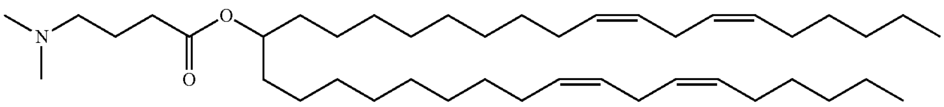 [SMILES: CCCCC/C=C\C/C=C\CCCCCCCCC(CCCCCCCC/C=C\C/C=C\CCCCC)OC(=O)CCCN(C)C]

and pharmaceutically acceptable salts thereof.

Other suitable cationic lipids for use in the compositions and methods of the present invention include ionizable cationic lipids as described in International Patent Publication WO 2013/149140, which is incorporated herein by reference. In some embodiments, the compositions and methods of the present invention include a cationic lipid of one of the following formulas:

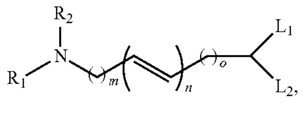

-continued

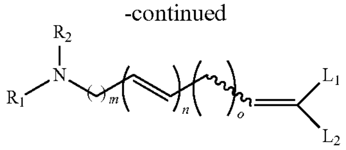

or a pharmaceutically acceptable salt thereof, wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one). In certain embodiments, the compositions and methods of the present invention include the cationic lipid (15Z, 18Z)—N,N-dimethyl-6-(9Z,12Z)-octadeca-9,12-dien-1-yl) tetracosa-15,18-dien-1-amine ("HGT5000"), having a compound structure of:

(HGT-5000)

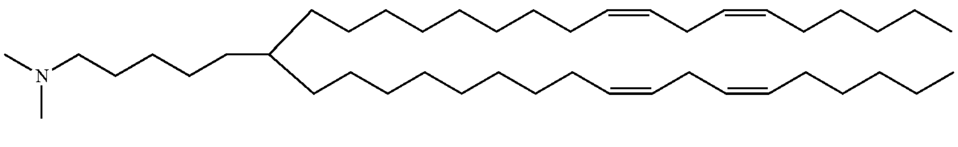

and pharmaceutically acceptable salts thereof. In certain embodiments, the compositions and methods of the present invention include the cationic lipid (15Z, 18Z)—N,N-dimethyl-6-((9Z,12Z)-octadeca-9,12-dien-1-yl) tetracosa-4,15,18-trien-1-amine ("HGT5001"), having a compound structure of:

(HGT-5001)

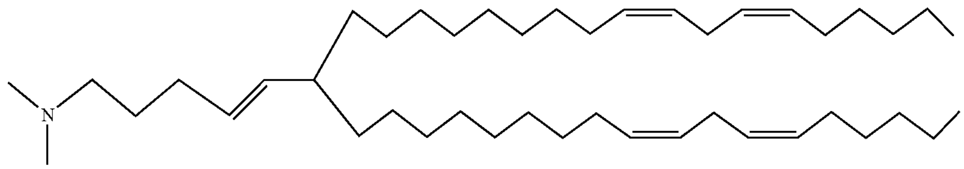

and pharmaceutically acceptable salts thereof. In certain embodiments, the compositions and methods of the present invention include the cationic lipid and (15Z,18Z)—N,N-dimethyl-6-((9Z,12Z)-octadeca-9,12-dien-1-yl) tetracosa-5,15,18-trien-1-amine ("HGT5002"), having a compound structure of:

(HGT-5002)

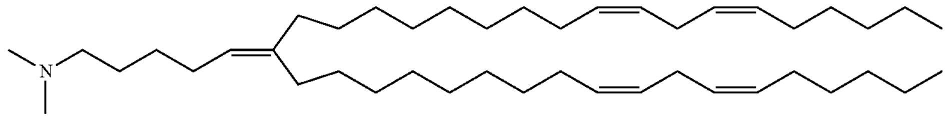

and pharmaceutically acceptable salts thereof.

Other suitable cationic lipids for use in the compositions and methods of the invention include cationic lipids described as aminoalcohol lipidoids in International Patent Publication WO 2010/053572, which is incorporated herein by reference. In certain embodiments, the compositions and methods of the present invention include a cationic lipid having a compound structure of:

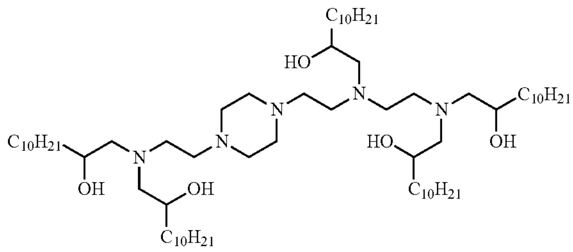

and pharmaceutically acceptable salts thereof.

Other suitable cationic lipids for use in the compositions and methods of the invention include the cationic lipids as described in International Patent Publication WO 2016/118725, which is incorporated herein by reference. In certain embodiments, the compositions and methods of the present invention include a cationic lipid having a compound structure of:

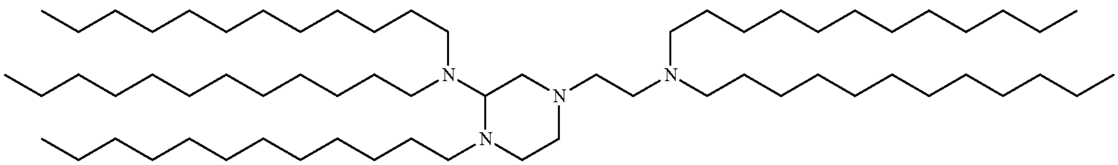 [SMILES: CCCCCCCCCCCCN(CCCCCCCCCCCC)CCN1CCN(CCCCCCCCCCCC)C(N(CCCCCCCCCCCC)CCCCCCCCCCCC)C1]

and pharmaceutically acceptable salts thereof.

Other suitable cationic lipids for use in the compositions and methods of the invention include the cationic lipids as described in International Patent Publication WO 2016/118724, which is incorporated herein by reference. In certain embodiments, the compositions and methods of the present invention include a cationic lipid having a compound structure of:

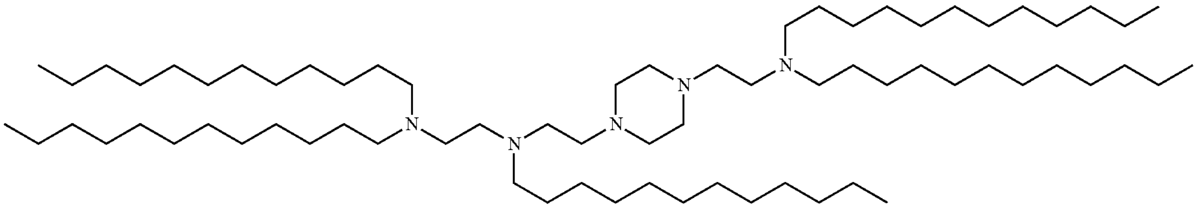 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1]

and pharmaceutically acceptable salts thereof.

Other suitable cationic lipids for use in the compositions and methods of the invention include a cationic lipid having the formula of 14,25-ditridecyl 15,18,21,24-tetraaza-octatriacontane, and pharmaceutically acceptable salts thereof.

Other suitable cationic lipids for use in the compositions and methods of the invention include the cationic lipids as described in International Patent Publications WO 2013/063468 and WO 2016/205691, each of which are incorporated herein by reference. In some embodiments, the compositions and methods of the present invention include a cationic lipid of the following formula:

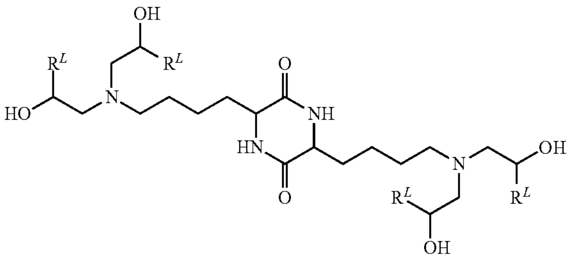

or pharmaceutically acceptable salts thereof, wherein each instance of $R^L$ is independently optionally substituted $C_6$-$C_{40}$ alkenyl. In certain embodiments, the compositions and methods of the present invention include a cationic lipid having a compound structure of:

(cKK-E12)

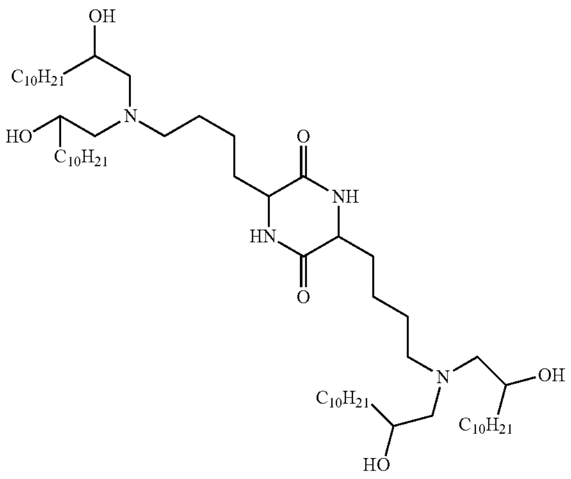

and pharmaceutically acceptable salts thereof. In certain embodiments, the compositions and methods of the present invention include a cationic lipid having a compound structure of:

(OF-02)

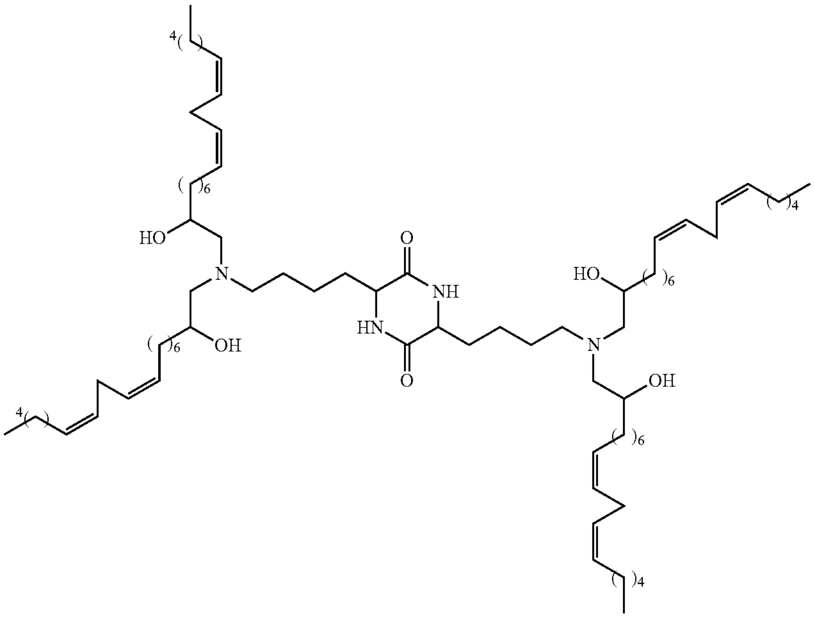

and pharmaceutically acceptable salts thereof. In certain embodiments, the compositions and methods of the present invention include a cationic lipid having a compound structure of:

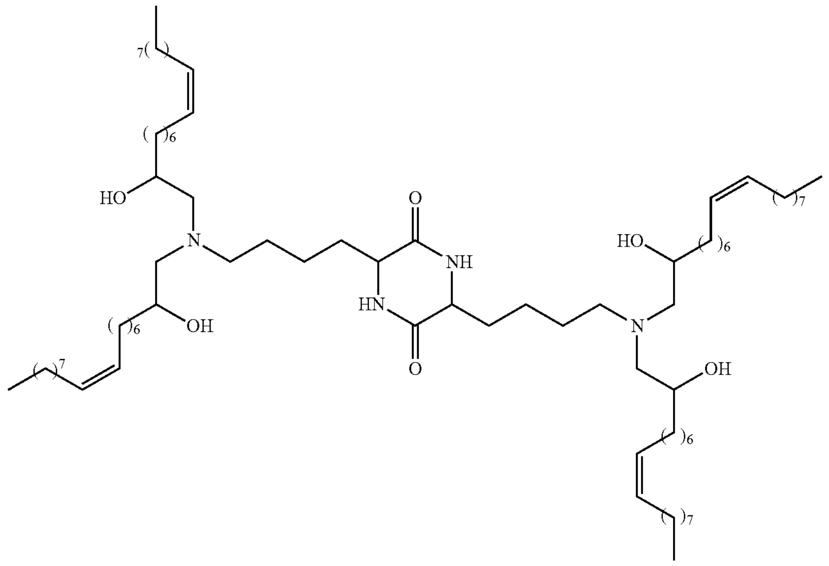

and pharmaceutically acceptable salts thereof. In certain embodiments, the compositions and methods of the present invention include a cationic lipid having a compound structure of:

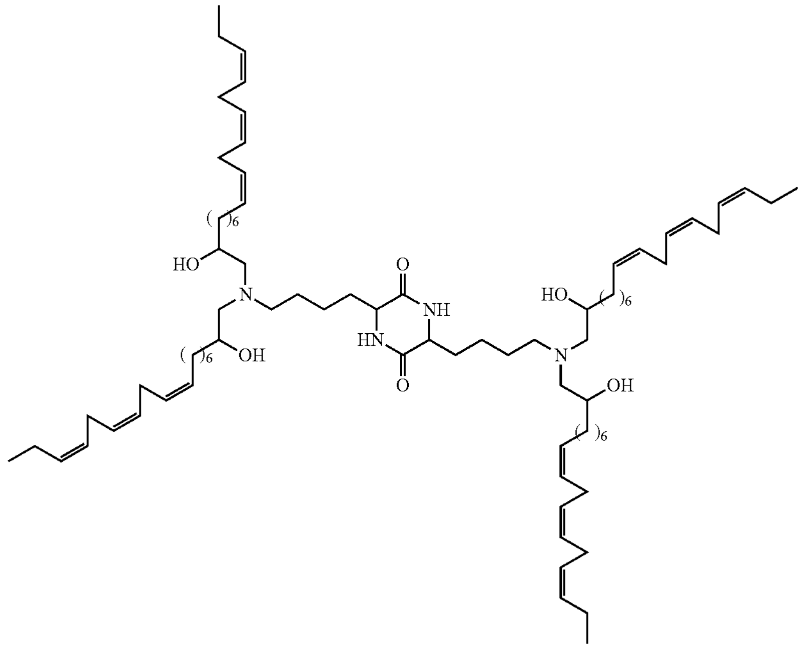

and pharmaceutically acceptable salts thereof.

Other suitable cationic lipids for use in the compositions and methods of the invention include the cationic lipids as described in International Patent Publication WO 2015/184256, which is incorporated herein by reference. In some embodiments, the compositions and methods of the present invention include a cationic lipid of the following formula:

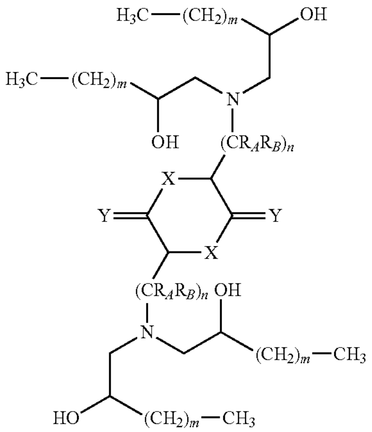

or a pharmaceutically acceptable salt thereof, wherein each X independently is O or S; each Y independently is O or S; each m independently is 0 to 20; each n independently is 1 to 6; each $R_A$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen; and each $R_B$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen. In certain embodiments, the compositions and methods of the present invention include a cationic lipid, "Target 23", having a compound structure of:

(Target 23)

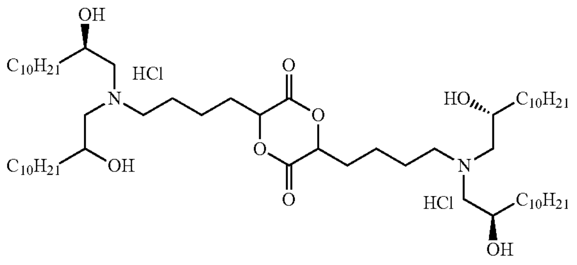

and pharmaceutically acceptable salts thereof.

Other suitable cationic lipids for use in the compositions and methods of the invention include the cationic lipids as described in International Patent Publication WO 2016/004202, which is incorporated herein by reference. In some embodiments, the compositions and methods of the present invention include a cationic lipid having the compound structure:

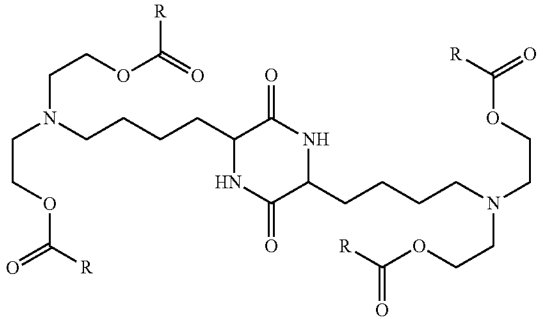

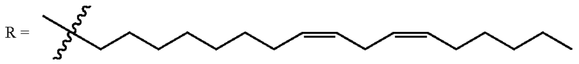

or a pharmaceutically acceptable salt thereof. In some embodiments, the compositions and methods of the present invention include a cationic lipid having the compound structure:

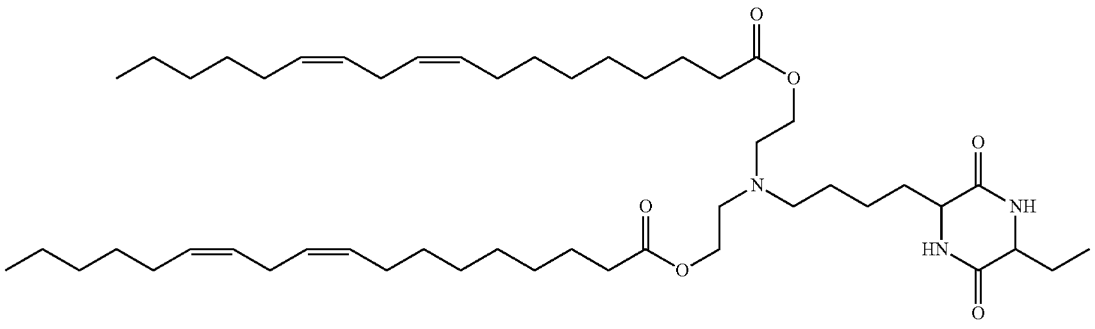 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC]

or a pharmaceutically acceptable salt thereof. In some embodiments, the compositions and methods of the present invention include a cationic lipid having the compound structure:

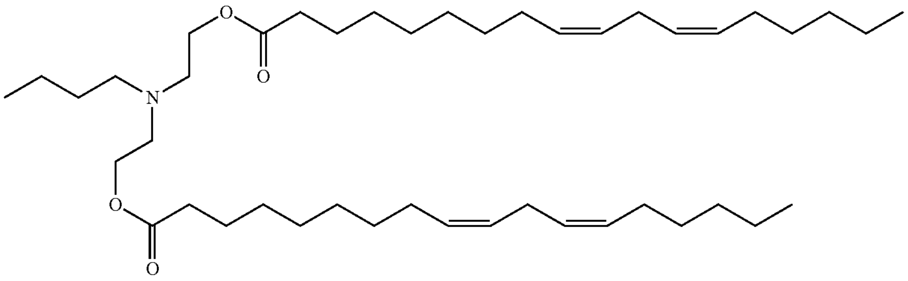 [SMILES: CCCCC/C=C\C/C=C\CCCCCCCC(=O)OCCN(CCCC)CCOC(=O)CCCCCCC/C=C\C/C=C\CCCCC]

or a pharmaceutically acceptable salt thereof.

Other suitable cationic lipids for use in the compositions and methods of the present invention include cationic lipids as described in U.S. Provisional Patent Application Ser. No. 62/758,179, which is incorporated herein by reference. In some embodiments, the compositions and methods of the present invention include a cationic lipid of the following formula:

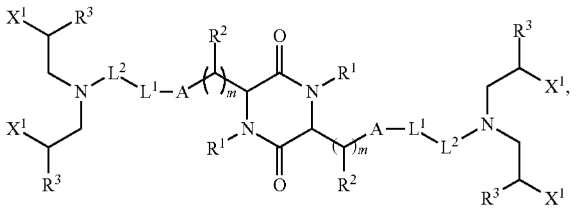

or a pharmaceutically acceptable salt thereof, wherein each $R^1$ and $R^2$ is independently H or $C_1$-$C_6$ aliphatic; each m is independently an integer having a value of 1 to 4; each A is independently a covalent bond or arylene; each $L^1$ is independently an ester, thioester, disulfide, or anhydride group; each $L^2$ is independently $C_2$-$C_{10}$ aliphatic; each $X^1$ is independently H or OH; and each $R^3$ is independently $C_6$-$C_{20}$ aliphatic. In some embodiments, the compositions and methods of the present invention include a cationic lipid of the following formula:

(Compound 1)

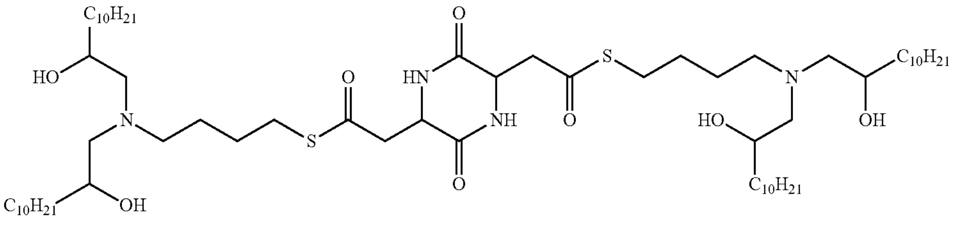

or a pharmaceutically acceptable salt thereof. In some embodiments, the compositions and methods of the present invention include a cationic lipid of the following formula:

(Compound 2)

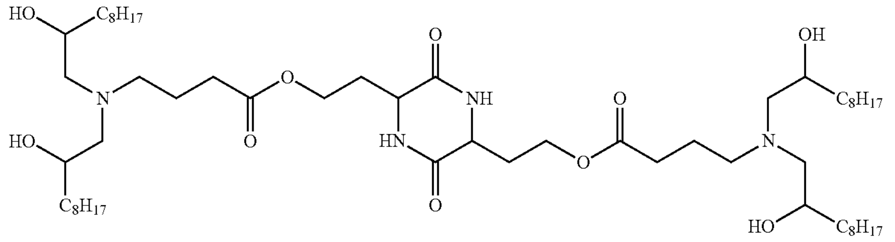

or a pharmaceutically acceptable salt thereof. In some embodiments, the compositions and methods of the present invention include a cationic lipid of the following formula:

(Compound 3)

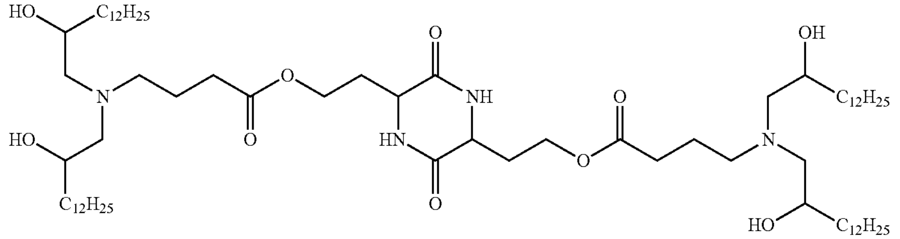

or a pharmaceutically acceptable salt thereof.

Other suitable cationic lipids for use in the compositions and methods of the present invention include the cationic lipids as described in J. McClellan, M. C. King, Cell 2010, 141, 210-217 and in Whitehead et al., Nature Communications (2014) 5:4277, which is incorporated herein by reference. In certain embodiments, the cationic lipids of the compositions and methods of the present invention include a cationic lipid having a compound structure of:

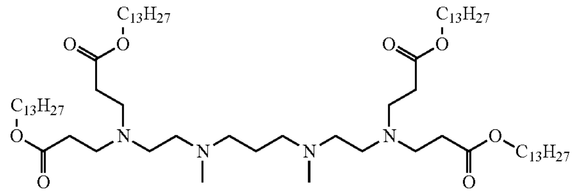

and pharmaceutically acceptable salts thereof.

Other suitable cationic lipids for use in the compositions and methods of the invention include the cationic lipids as described in International Patent Publication WO 2015/199952, which is incorporated herein by reference. In some embodiments, the compositions and methods of the present invention include a cationic lipid having the compound structure:

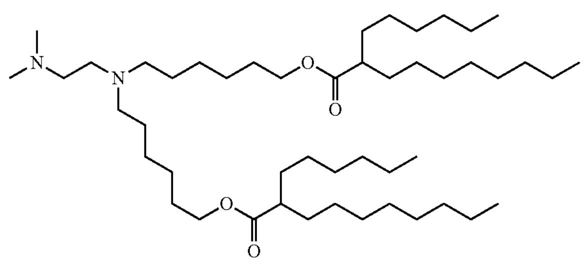 [SMILES: CCCCCCCCC(CCCCCC)C(=O)OCCCCCCN(CCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

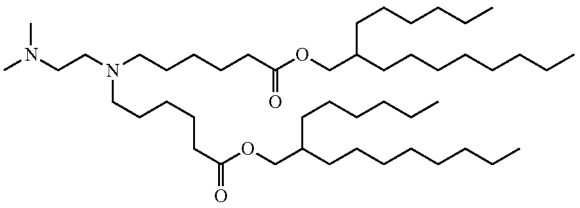

and pharmaceutically acceptable salts thereof. In some embodiments, the compositions and methods of the present invention include a cationic lipid having the compound structure:

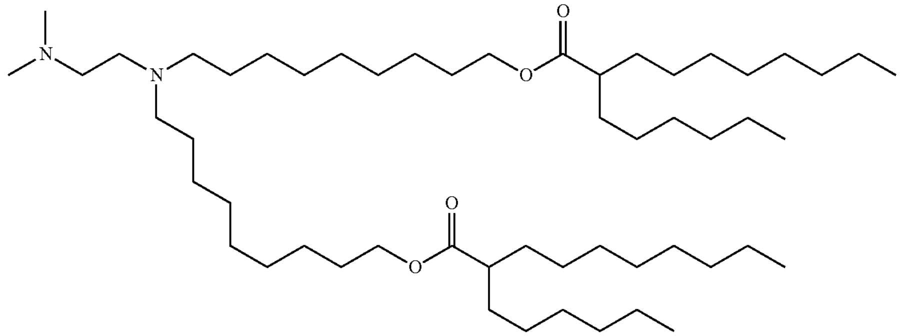 [SMILES: CCCCCCCCC(CCCCCC)C(=O)OCCCCCCCCCN(CCCCCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

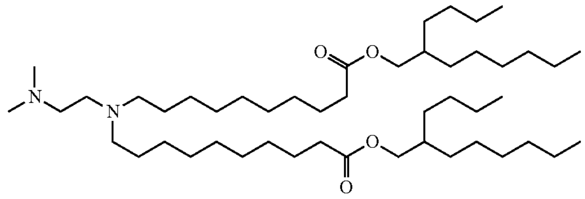 [SMILES: CCCCCCC(CCCC)COC(=O)CCCCCCCCCN(CCCCCCCCCC(=O)OCC(CCCC)CCCCCC)CCN(C)C]

and pharmaceutically acceptable salts thereof. In some embodiments, the compositions and methods of the present invention include a cationic lipid having the compound structure:

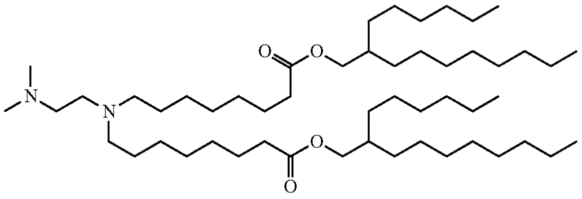 [SMILES: CCCCCCCCC(CCCCCC)COC(=O)CCCCCCCN(CCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

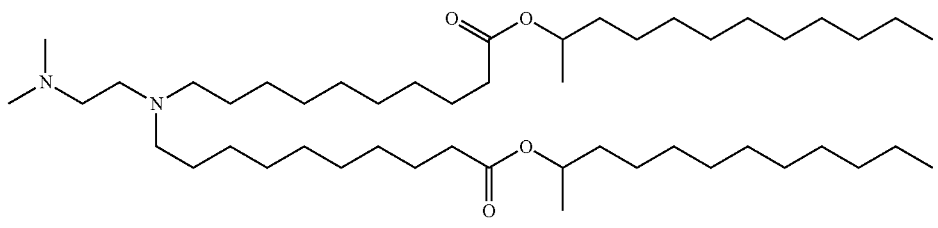 [SMILES: CCCCCCCCCCC(C)OC(=O)CCCCCCCCCN(CCCCCCCCCC(=O)OC(C)CCCCCCCCCC)CCN(C)C]

and pharmaceutically acceptable salts thereof. In some embodiments, the compositions and methods of the present invention include a cationic lipid having the compound structure:

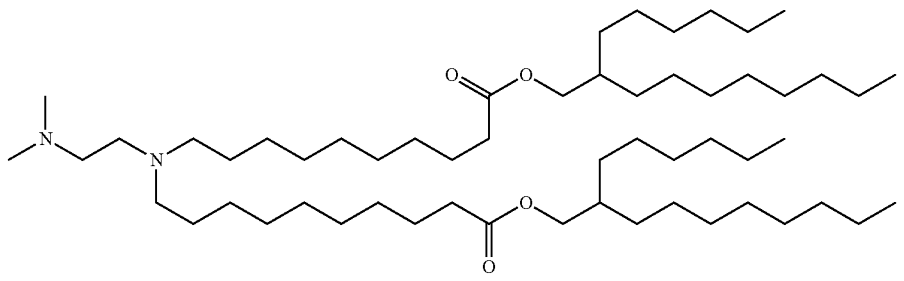 [SMILES: CCCCCCCCC(CCCCCC)COC(=O)CCCCCCCCCN(CCCCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

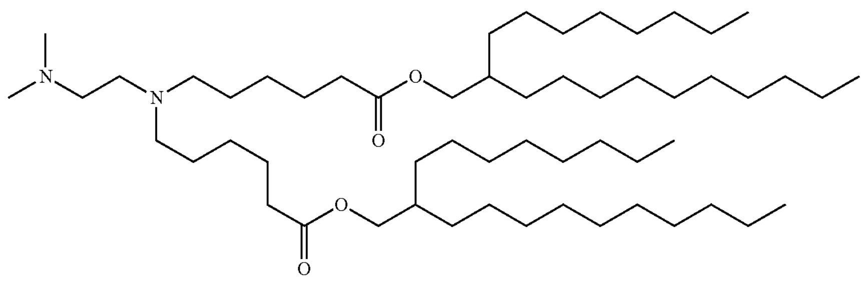 [SMILES: CCCCCCCCCCC(CCCCCCCC)COC(=O)CCCCCN(CCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

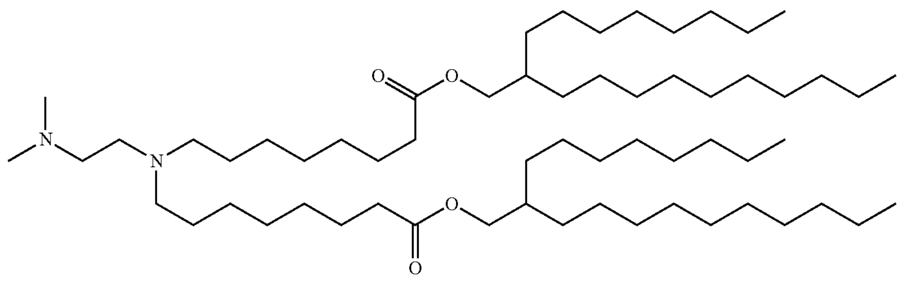 [SMILES: CCCCCCCCCCC(CCCCCCCC)COC(=O)CCCCCCCN(CCCCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

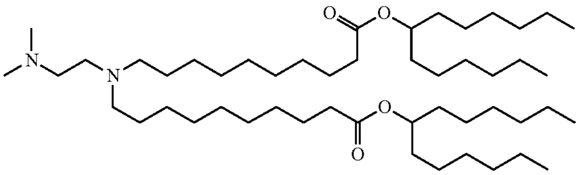 [SMILES: CCCCCCC(CCCCCC)OC(=O)CCCCCCCCCN(CCCCCCCCCC(=O)OC(CCCCCC)CCCCCC)CCN(C)C]

and pharmaceutically acceptable salts thereof. In some embodiments, the compositions and methods of the present invention include a cationic lipid having the compound structure:

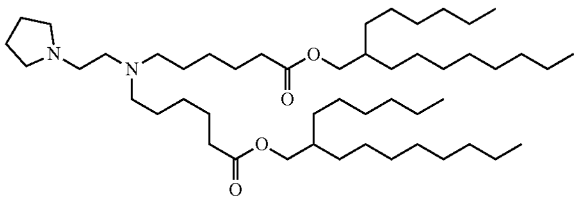 [SMILES: CCCCCCCCC(CCCCCC)COC(=O)CCCCCN(CCCCCC(=O)OCC(CCCCCC)CCCCCCCC)CCN1CCCC1]

and pharmaceutically acceptable salts thereof. In some embodiments, the compositions and methods of the present invention include a cationic lipid having the compound structure:

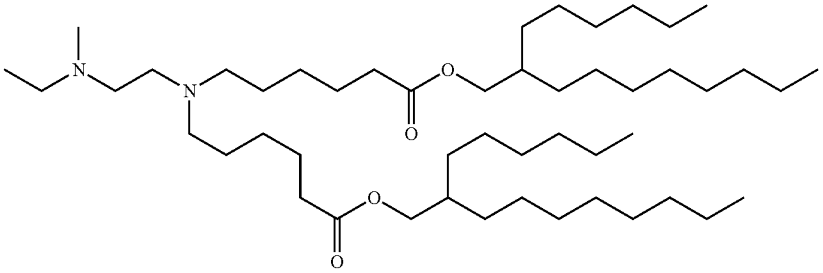 [SMILES: CCCCCCCCC(CCCCCC)COC(=O)CCCCCN(CCCCCC(=O)OCC(CCCCCC)CCCCCCCC)CCN(C)CC]

and pharmaceutically acceptable salts thereof. In some embodiments, the compositions and methods of the present invention include a cationic lipid having the compound structure:

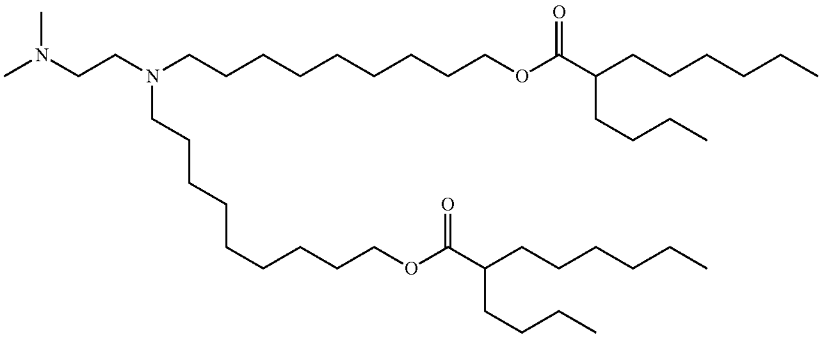 [SMILES: CCCCCCC(CCCC)C(=O)OCCCCCCCCCN(CCCCCCCCCOC(=O)C(CCCC)CCCCCC)CCN(C)C]

and pharmaceutically acceptable salts thereof.

Other suitable cationic lipids for use in the compositions and methods of the invention include the cationic lipids as described in International Patent Publication WO 2017/004143, which is incorporated herein by reference. In some embodiments, the compositions and methods of the present invention include a cationic lipid having the compound structure:

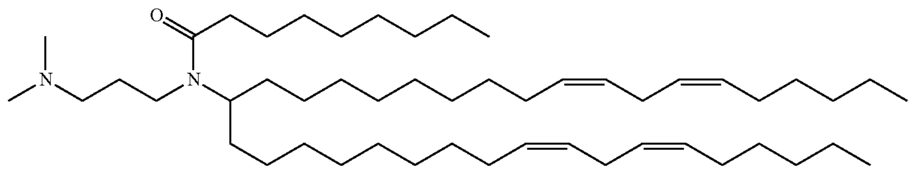 [SMILES: CCCCC/C=C\C/C=C\CCCCCCCCC(CCCCCCCC/C=C\C/C=C\CCCCC)N(CCCN(C)C)C(=O)CCCCCCCC]

and pharmaceutically acceptable salts thereof. In some embodiments, the compositions and methods of the present invention include a cationic lipid having the compound structure:

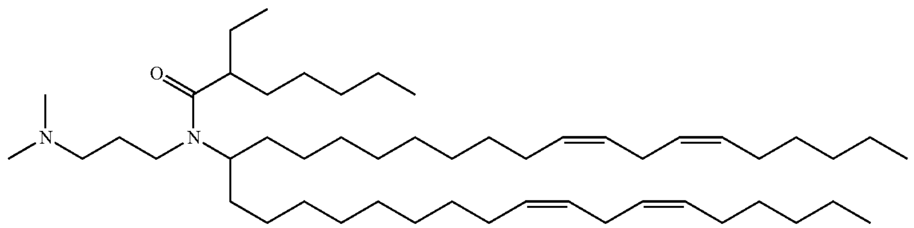 [SMILES: CCCCC/C=C\C/C=C\CCCCCCCCC(CCCCCCCC/C=C\C/C=C\CCCCC)N(CCCN(C)C)C(=O)C(CC)CCCCC]

and pharmaceutically acceptable salts thereof. In some embodiments, the compositions and methods of the present invention include a cationic lipid having the compound structure:

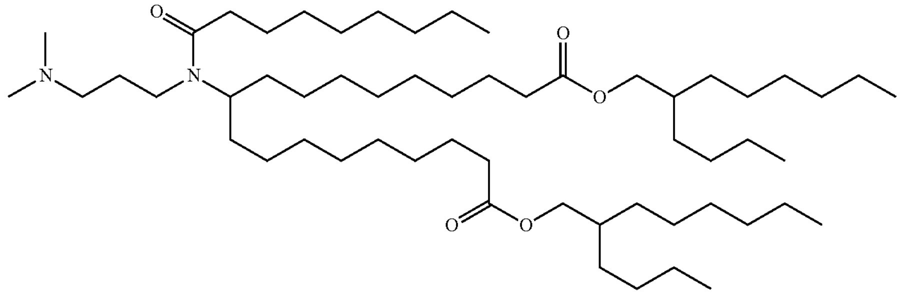 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

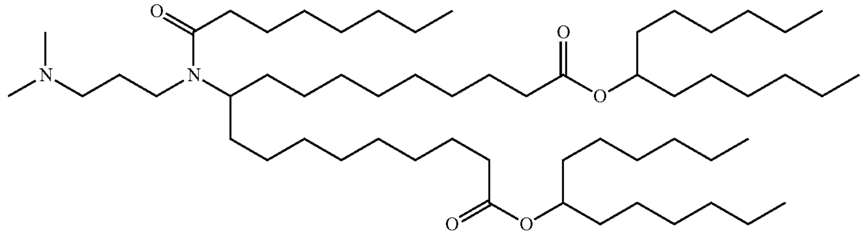 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

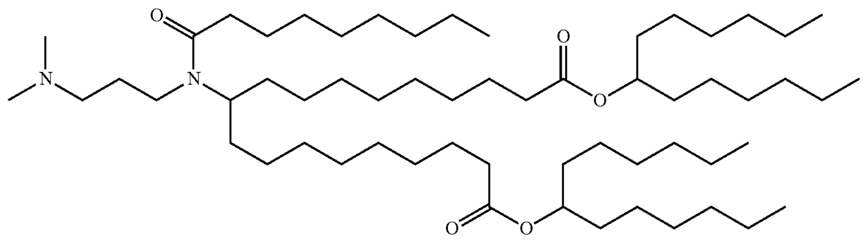 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

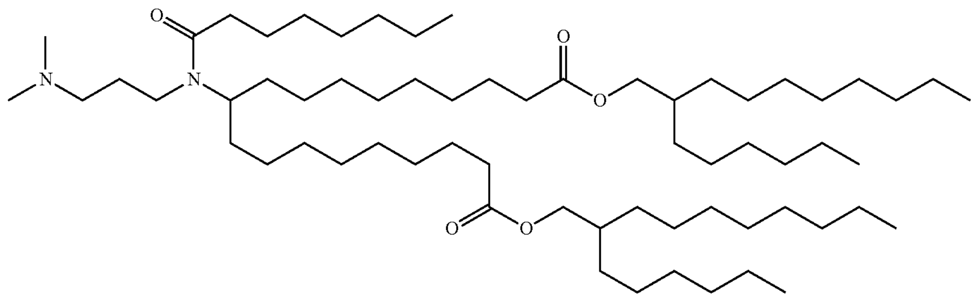 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

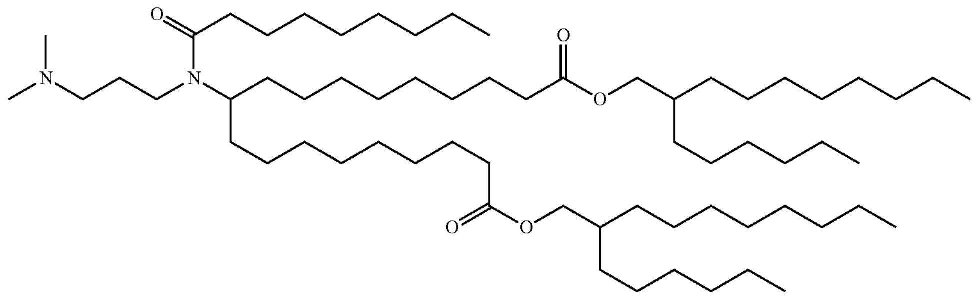 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC]

and pharmaceutically acceptable salts thereof. In some embodiments, the compositions and methods of the present invention include a cationic lipid having the compound structure:

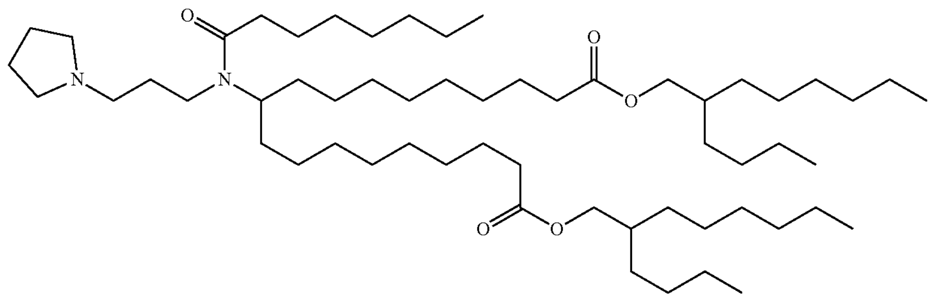 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

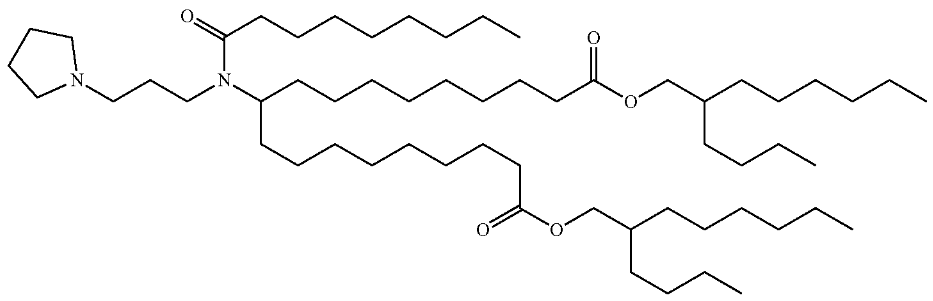 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

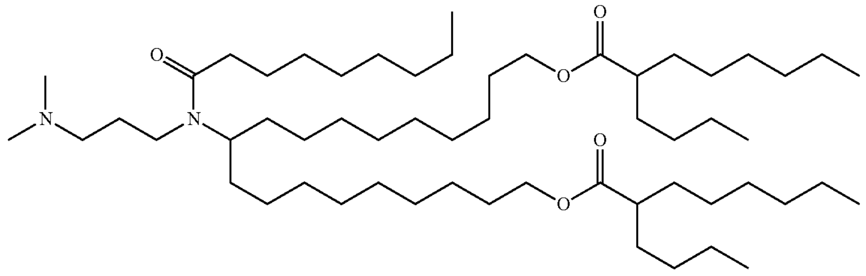 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC]

and pharmaceutically acceptable salts thereof. In some embodiments, the compositions and methods of the present invention include a cationic lipid having the compound structure:

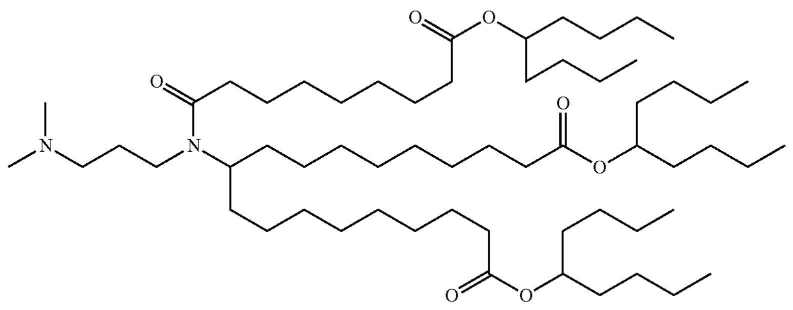 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC]

and pharmaceutically acceptable salts thereof. In some embodiments, the compositions and methods of the present invention include a cationic lipid having the compound structure:

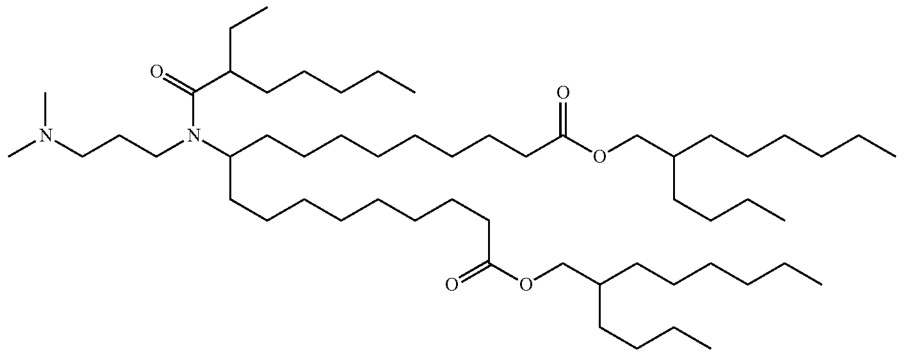 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC]

and pharmaceutically acceptable salts thereof. In some embodiments, the compositions and methods of the present invention include a cationic lipid having the compound structure:

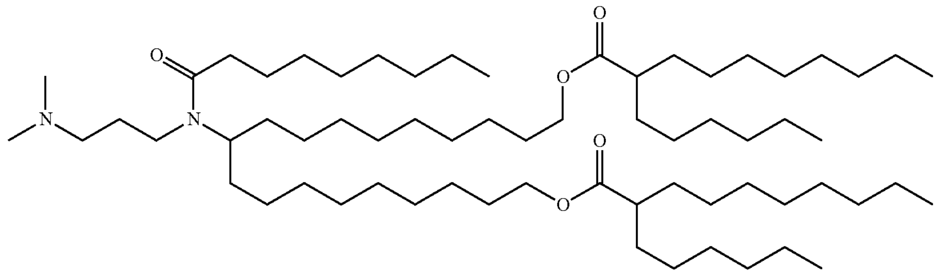 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC]

and pharmaceutically acceptable salts thereof. In some embodiments, the compositions and methods of the present invention include a cationic lipid having the compound structure:

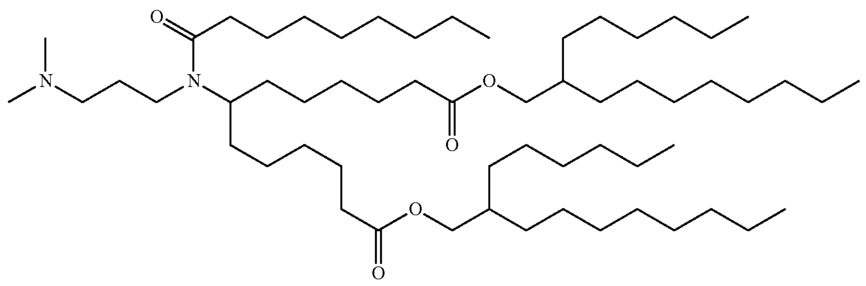 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC]

and pharmaceutically acceptable salts thereof. In some embodiments, the compositions and methods of the present invention include a cationic lipid having the compound structure:

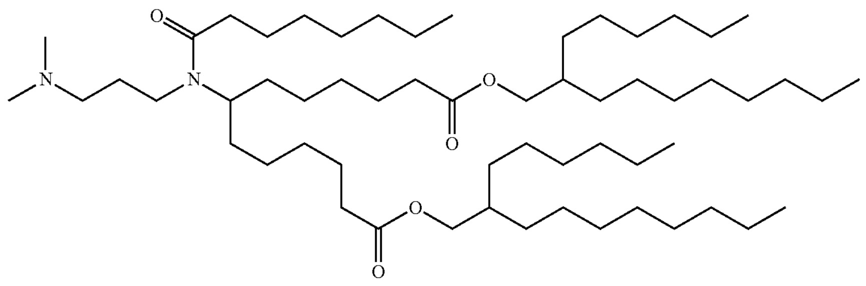 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

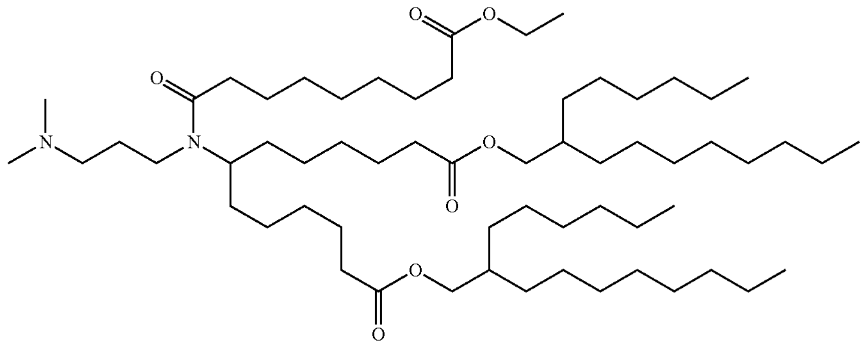 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC]

and pharmaceutically acceptable salts thereof. In some embodiments, the compositions and methods of the present invention include a cationic lipid having the compound structure:

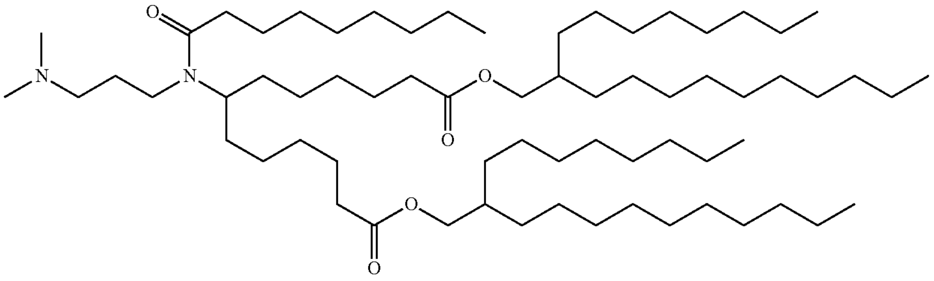 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC]

and pharmaceutically acceptable salts thereof.

Other suitable cationic lipids for use in the compositions and methods of the invention include the cationic lipids as described in International Patent Publication WO 2017/075531, which is incorporated herein by reference. In some embodiments, the compositions and methods of the present invention include a cationic lipid of the following formula:

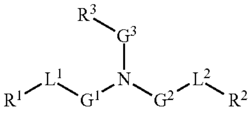

or a pharmaceutically acceptable salt thereof, wherein one of $L^1$ or $L^2$ is —O(C═O)—, —(C═O)O—, —C(═O)—, —O—, —S(O)$_x$, —S—S—, —C(═O)S—, —SC(═O)—, —NR$^a$C(═O)—, —C(═O)NR$^a$—, NR$^a$C(═O)NR$^a$—, —OC(═O)NR$^a$—, or —NR$^a$C(═O)O—; and the other of $L^1$ or $L^2$ is —O(C═O)—, —(C═O)O—, —C(═O)—, —O—, —S(O)$_x$, —S—S—, —C(═O)S—, SC(═O)—, —NR$^a$C(═O)—, —C(═O)NR$^a$—, NR$^a$C(═O)NR$^a$—, —OC(═O)NR$^a$— or —NR$^a$C(═O)O— or a direct bond; $G^1$ and $G^2$ are each independently unsubstituted $C_1$-$C_{12}$ alkylene or $C_1$-$C_{12}$ alkenylene; $G^3$ is $C_1$-$C_{24}$ alkylene, $C_1$-$C_{24}$ alkenylene, $C_3$-$C_8$ cycloalkylene, $C_3$-$C_8$ cycloalkenylene; $R^a$ is H or $C_1$-$C_{12}$ alkyl; $R^1$ and $R^2$ are each independently $C_6$-$C_{24}$ alkyl or $C_6$-$C_{24}$ alkenyl; $R^3$ is H, $OR^5$, CN, —C(═O)OR$^4$, —OC(═O)R$^4$ or —NR$^5$C(═O)R$^4$; $R^4$ is $C_1$-$C_{12}$ alkyl; $R^5$ is H or $C_1$-$C_6$ alkyl; and x is 0, 1 or 2.

Other suitable cationic lipids for use in the compositions and methods of the invention include the cationic lipids as described in International Patent Publication WO 2017/117528, which is incorporated herein by reference. In some embodiments, the compositions and methods of the present invention include a cationic lipid having the compound structure:

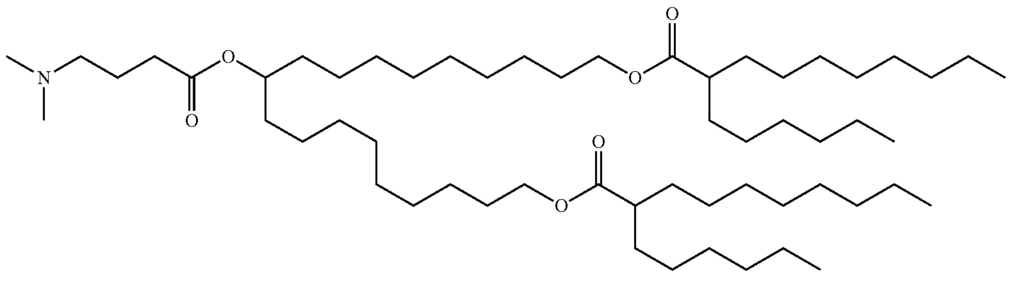 [SMILES: CCCCCCCCC(CCCCCC)C(=O)OCCCCCCCCCC(CCCCCCCCCOC(=O)C(CCCCCC)CCCCCCCC)OC(=O)CCCN(C)C]

and pharmaceutically acceptable salts thereof. In some embodiments, the compositions and methods of the present invention include a cationic lipid having the compound structure:

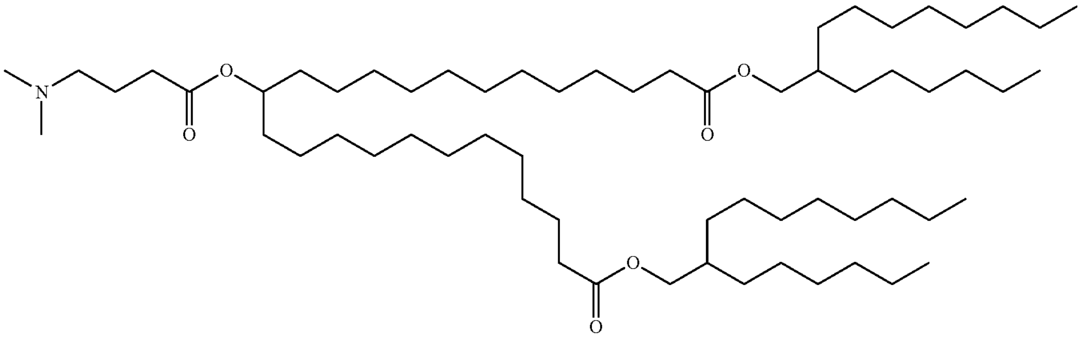 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C]

and pharmaceutically acceptable salts thereof. In some embodiments, the compositions and methods of the present invention include a cationic lipid having the compound structure:

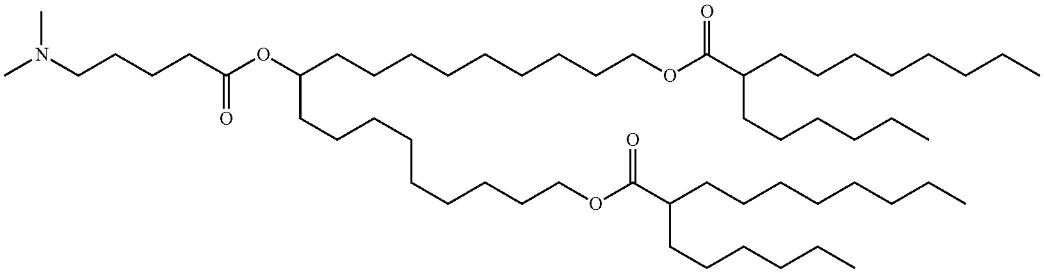 [SMILES: CCCCCCCCC(CCCCCC)C(=O)OCCCCCCCCCC(CCCCCCCCCOC(=O)C(CCCCCC)CCCCCCCC)OC(=O)CCCCN(C)C]

and pharmaceutically acceptable salts thereof.

Other suitable cationic lipids for use in the compositions and methods of the invention include the cationic lipids as described in International Patent Publication WO 2017/049245, which is incorporated herein by reference. In some embodiments, the cationic lipids of the compositions and methods of the present invention include a compound of one of the following formulas:

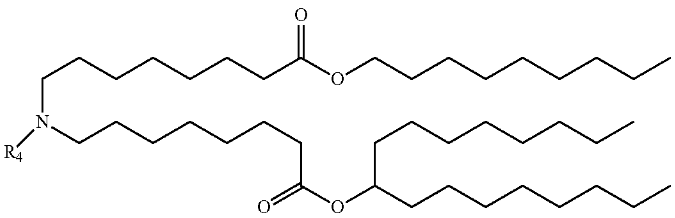

,

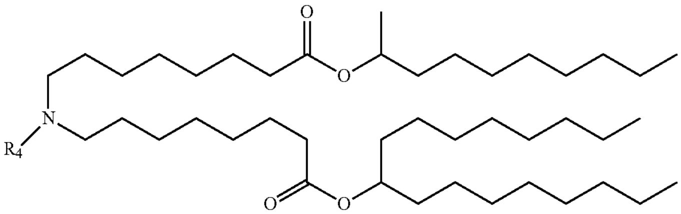

,

-continued

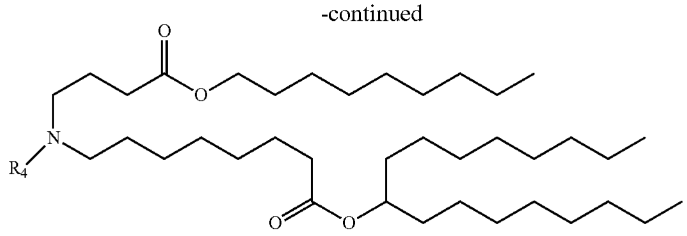

, and

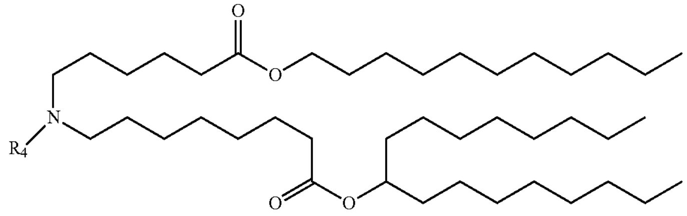

, and pharmaceutically acceptable salts thereof. For any one of these four formulas, $R_4$ is independently selected from —$(CH_2)_nQ$ and —$(CH_2)_nCHQR$; Q is selected from the group consisting of —OR, —OH, —$O(CH_2)_nN(R)_2$, —OC(O)R, —$CX_3$, —CN, —N(R)C(O)R, —N(H)C(O)R, —$N(R)S(O)_2R$, —$N(H)S(O)_2R$, —$N(R)C(O)N(R)_2$, —$N(H)C(O)N(R)_2$, —N(H)C(O)N(H)(R), —$N(R)C(S)N(R)_2$, —$N(H)C(S)N(R)_2$, —N(H)C(S)N(H)(R), and a heterocycle; and n is 1, 2, or 3. In certain embodiments, the compositions and methods of the present invention include a cationic lipid having a compound structure of:

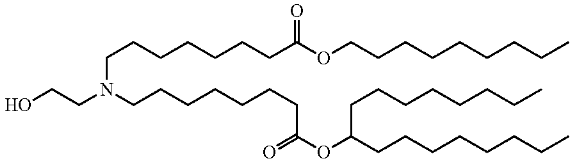 [SMILES: CCCCCCCCCOC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

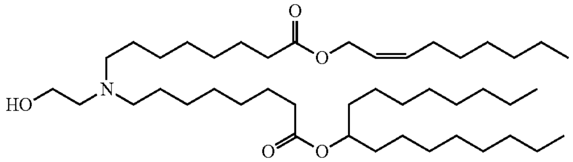 [SMILES: CCCCCC/C=C\COC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

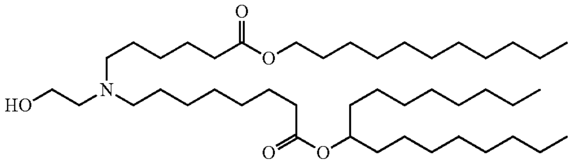 [SMILES: CCCCCCCCCCCOC(=O)CCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

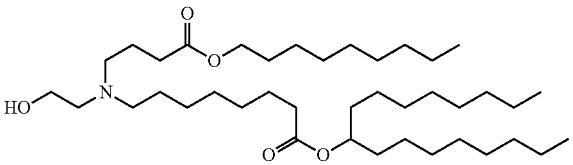 [SMILES: CCCCCCCCCOC(=O)CCCN(CCO)CCCCCCCC(=O)OC(CCCCCCCC)CCCCCCCC]

and pharmaceutically acceptable salts thereof.

Other suitable cationic lipids for use in the compositions and methods of the invention include the cationic lipids as described in International Patent Publication WO 2017/173054 and WO 2015/095340, each of which is incorporated herein by reference. In certain embodiments, the compositions and methods of the present invention include a cationic lipid having a compound structure of:

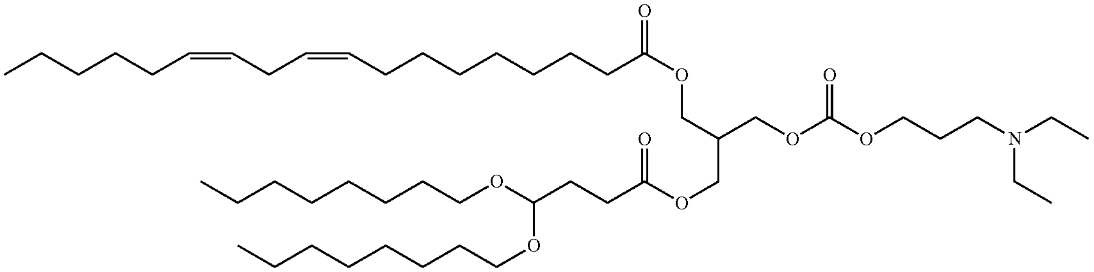 [SMILES: CCCCC/C=C\C/C=C\CCCCCCCC(=O)OCC(COC(=O)CCC(OCCCCCCCC)OCCCCCCCC)COC(=O)OCCCN(CC)CC]

and pharmaceutically acceptable salts thereof. In certain embodiments, the compositions and methods of the present invention include a cationic lipid having a compound structure of:

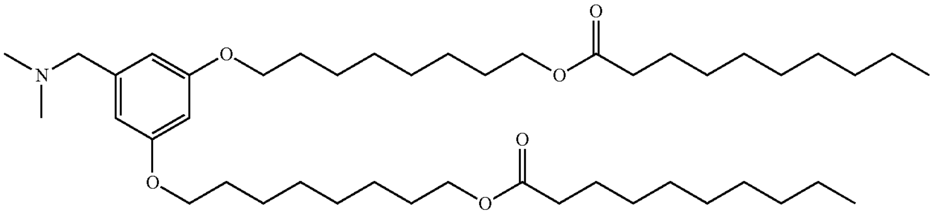 [SMILES: CCCCCCCCCC(=O)OCCCCCCCCOc1cc(CN(C)C)cc(OCCCCCCCCOC(=O)CCCCCCCCC)c1]

and pharmaceutically acceptable salts thereof. In certain embodiments, the compositions and methods of the present invention include a cationic lipid having a compound structure of:

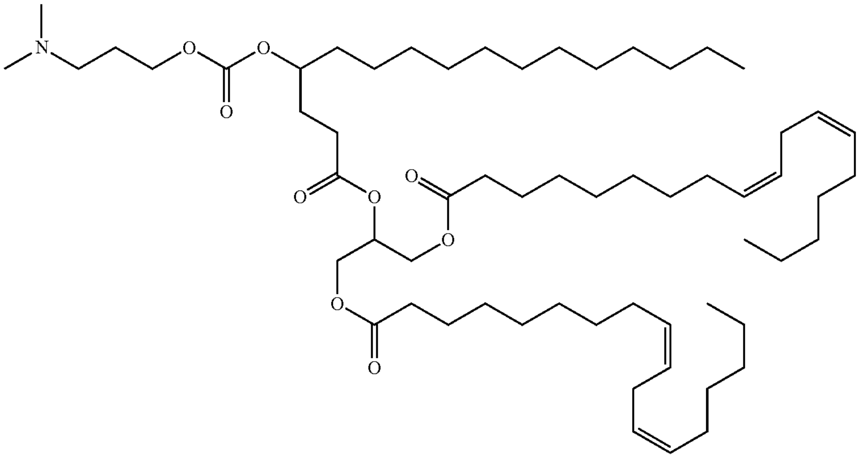 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

and pharmaceutically acceptable salts thereof. In certain embodiments, the compositions and methods of the present invention include a cationic lipid having a compound structure of:

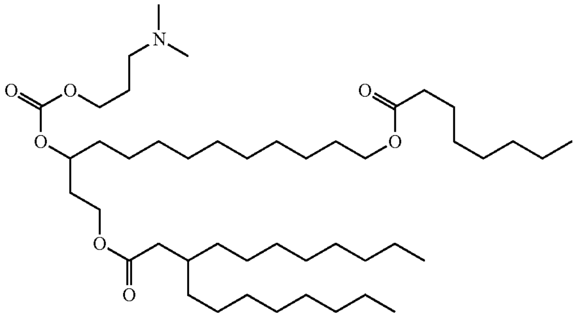 [SMILES: CCCCCCCCC(CCCCCCCC)CC(=O)OCCC(CCCCCCCCCCOC(=O)CCCCCCC)OC(=O)OCCCN(C)C]

and pharmaceutically acceptable salts thereof.

Other suitable cationic lipids for use in the compositions and methods of the invention include cholesterol-based cationic lipids. In certain embodiments, the compositions and methods of the present invention include imidazole cholesterol ester or "ICE", having a compound structure of:

(ICE)

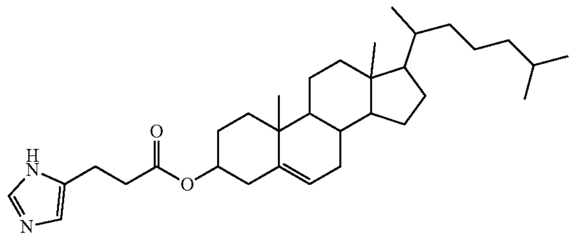

and pharmaceutically acceptable salts thereof.

Other suitable cationic lipids for use in the compositions and methods of the present invention include cleavable cationic lipids as described in International Patent Publication WO 2012/170889, which is incorporated herein by reference. In some embodiments, the compositions and methods of the present invention include a cationic lipid of the following formula:

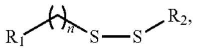

wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of one of the following two formulas:

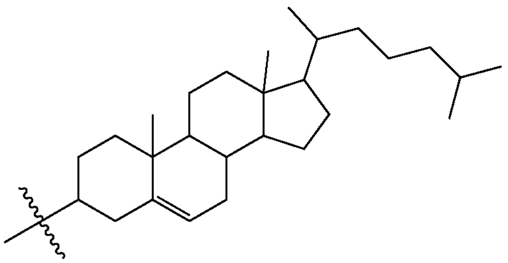

and

-continued

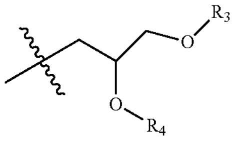

and wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, the compositions and methods of the present invention include a cationic lipid, "HGT4001", having a compound structure of:

(HGT4001)

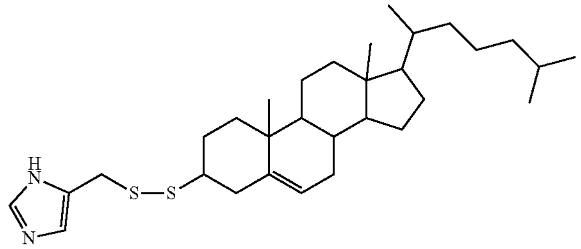

and pharmaceutically acceptable salts thereof. In certain embodiments, the compositions and methods of the present invention include a cationic lipid, "HGT4002", having a compound structure of:

(HGT4002)

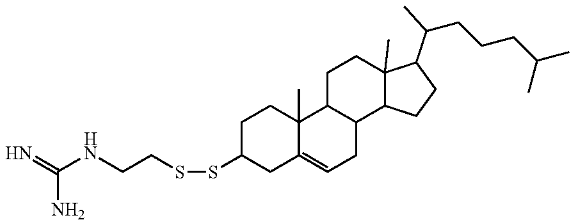

and pharmaceutically acceptable salts thereof. In certain embodiments, the compositions and methods of the present invention include a cationic lipid, "HGT4003", having a compound structure of:

(HGT4003)

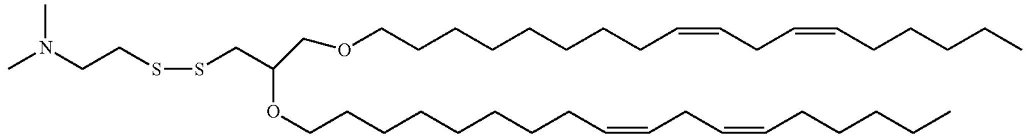

and pharmaceutically acceptable salts thereof. In certain embodiments, the compositions and methods of the present invention include a cationic lipid, "HGT4004", having a compound structure of:

(HGT4004)

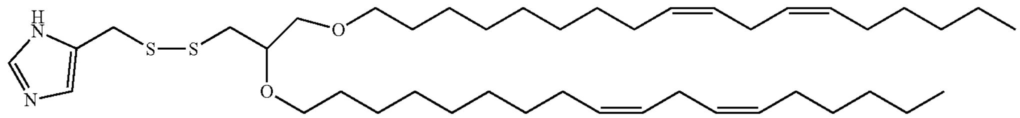

and pharmaceutically acceptable salts thereof. In certain embodiments, the compositions and methods of the present invention include a cationic lipid "HGT4005", having a compound structure of:

(HGT4005)

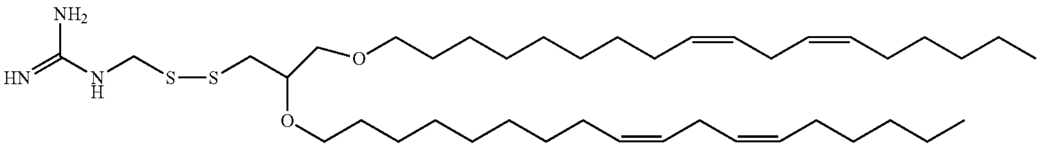

and pharmaceutically acceptable salts thereof.

Other suitable cationic lipids for use in the compositions and methods of the present invention include cleavable cationic lipids as described in U.S. Provisional Application No. 62/672,194, filed May 16, 2018, and incorporated herein by reference. In certain embodiments, the compositions and methods of the present invention include a cationic lipid that is any of general formulas or any of structures (1a)-(21a) and (1b)-(21b) and (22)-(237) described in U.S. Provisional Application No. 62/672,194. In certain embodiments, the compositions and methods of the present invention include a cationic lipid that has a structure according to Formula (I'),

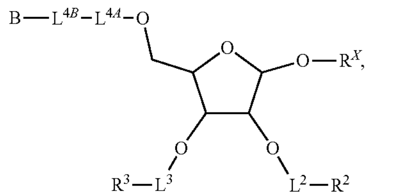

(I')

wherein:

RX is independently —H, -L1-R1, or -L5A-L5B-B';

each of L1, L2, and L3 is independently a covalent bond, —C(O)—, —C(O)O—, —C(O)S—, or —C(O)NRL-;

each L4A and L5A is independently —C(O)—, —C(O)O—, or —C(O)NRL-;

each L4B and L5B is independently C1-C20 alkylene; C2-C20 alkenylene; or C2-C20 alkynylene;

each B and B' is NR4R5 or a 5- to 10-membered nitrogen-containing heteroaryl;

each R1, R2, and R3 is independently C6-C30 alkyl, C6-C30 alkenyl, or C6-C30 alkynyl;

each R4 and R5 is independently hydrogen, C1-C10 alkyl; C2-C10 alkenyl; or C2-C10 alkynyl; and each RL is independently hydrogen, C1-C20 alkyl, C2-C20 alkenyl, or C2-C20 alkynyl.

In certain embodiments, the compositions and methods of the present invention include a cationic lipid that is Compound (139) of 62/672,194, having a compound structure of:

("18:1 Carbon tail-ribose lipid")

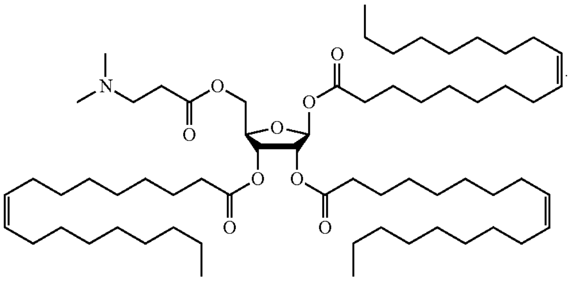

In some embodiments, the compositions and methods of the present invention include the cationic lipid, N-[1-(2,3-dioleyloxy)propyl]-N,N,N-trimethylammonium chloride ("DOTMA"). (Feigner et al. (Proc. Nat'l Acad. Sci. 84, 7413 (1987); U.S. Pat. No. 4,897,355, which is incorporated herein by reference). Other cationic lipids suitable for the compositions and methods of the present invention include, for example, 5-carboxyspermylglycinedioctadecylamide ("DOGS"); 2,3-dioleyloxy-N-[2(spermine-carboxamido) ethyl]-N,N-dimethyl-1-propanaminium ("DOSPA") (Behr et al. Proc. Nat.'l Acad. Sci. 86, 6982 (1989), U.S. Pat. Nos. 5,171,678; 5,334,761); 1,2-Dioleoyl-3-Dimethylammonium-Propane ("DODAP"); 1,2-Dioleoyl-3-Trimethylammonium-Propane ("DOTAP").

Additional exemplary cationic lipids suitable for the compositions and methods of the present invention also include: 1,2-distearyloxy-N,N-dimethyl-3-aminopropane ("DSDMA"); 1,2-dioleyloxy-N,N-dimethyl-3-aminopropane ("DODMA"); 1,2-dilinoleyloxy-N,N-dimethyl-3-aminopropane ("DLinDMA"); 1,2-dilinolenyloxy-N,N-dimethyl-3-aminopropane ("DLenDMA"); N-dioleyl-N,N-dimethylammonium chloride ("DODAC"); N,N-distearyl-N,N-dimethylarnrnonium bromide ("DDAB"); N-(1,2-dimyristyloxyprop-3-yl)-N,N-dimethyl-N-hydroxyethyl ammonium bromide ("DMRIE"); 3-dimethylamino-2-(cholest-5-en-3-beta-oxybutan-4-oxy)-1-(cis,cis-9,12-octadecadienoxy)propane ("CLinDMA"); 2-[5'-(cholest-5-en-3-beta-oxy)-3'-oxapentoxy)-3-dimethy 1-1-(cis,cis-9', 1-2'-octadecadienoxy)propane ("CpLinDMA"); N,N-dimethyl-3,4-dioleyloxybenzylamine ("DMOBA"); 1,2-N,N'-dioleylcarbamyl-3-dimethylaminopropane ("DOcarbDAP"); 2,3-Dilinoleoyloxy-N,N-dimethylpropylamine ("DLinDAP"); 1,2-N,N'-Dilinoleylcarbamyl-3-dimethylaminopropane ("DLincarbDAP"); 1,2-Dilinoleoylcarbamyl-3-dimethylaminopropane ("DLinCDAP"); 2,2-dilinoleyl-4-dimethylaminomethyl-[1,3]-dioxolane ("DLin-K-DMA"); 2-((8-[(3P)-cholest-5-en-3-yloxy]octyl)oxy)-N, N-dimethyl-3-[(9Z, 12Z)-octadeca-9, 12-dien-1-yloxy]propane-1-amine ("Octyl-CLinDMA"); (2R)-2-((8-[(3beta)-cholest-5-en-3-yloxy]octyl)oxy)-N, N-dimethyl-3-[(9Z, 12Z)-octadeca-9, 12-dien-1-yloxy]propan-1-amine ("Octyl-CLinDMA (2R)"); (2S)-2-((8-[(3P)-cholest-5-en-3-yloxy] octyl)oxy)-N, fsl-dimethyh3-[(9Z, 12Z)-octadeca-9, 12-dien-1-yloxy]propan-1-amine ("Octyl-CLinDMA (2S)"); 2,2-dilinoleyl-4-dimethylaminoethyl-[1,3]-dioxolane ("DLin-K-XTC2-DMA"); and 2-(2,2-di((9Z,12Z)-octadeca-9,12-dien-1-yl)-1,3-dioxolan-4-yl)-N,N-dimethylethanamine ("DLin-KC2-DMA") (see, WO 2010/042877, which is incorporated herein by reference; Semple et al., Nature Biotech. 28: 172-176 (2010)). (Heyes, J., et al., J Controlled Release 107: 276-287 (2005); Morrissey, D V., et al., Nat. Biotechnol. 23(8): 1003-1007 (2005); International Patent Publication WO 2005/121348). In some embodiments, one or more of the cationic lipids comprise at least one of an imidazole, dialkylamino, or guanidinium moiety.

In some embodiments, one or more cationic lipids suitable for the compositions and methods of the present invention include 2,2-Dilinoleyl-4-dimethylaminoethyl-[1,3]-dioxolane ("XTC"); (3aR,5s,6aS)-N,N-dimethyl-2,2-di((9Z, 12Z)-octadeca-9,12-dienyl)tetrahydro-3aH-cyclopenta[d] [1,3]dioxol-5-amine ("ALNY-100") and/or 4,7,13-tris(3-oxo-3-(undecylamino)propyl)-N1,N16-diundecyl-4,7,10, 13-tetraazahexadecane-1,16-diamide ("NC98-5").

In some embodiments, the compositions of the present invention include one or more cationic lipids that constitute at least about 5%, 10%, 20%, 30%, 35%, 40%, 45%, 50%, 55%, 60%, 65%, or 70%, measured by weight, of the total lipid content in the composition, e.g., a lipid nanoparticle. In some embodiments, the compositions of the present invention include one or more cationic lipids that constitute at least about 5%, 10%, 20%, 30%, 35%, 40%, 45%, 50%, 55%, 60%, 65%, 70%, or 80% measured as a mol %, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured by weight, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured as mol %, of the total lipid content in the composition, e.g., a lipid nanoparticle.

In some embodiments, sterol-based cationic lipids may be use instead or in addition to cationic lipids described herein. Suitable sterol-based cationic lipids are dialkylamino-, imidazole-, and guanidinium-containing sterol-based cationic lipids. For example, certain embodiments are directed to a composition comprising one or more sterol-based cationic lipids comprising an imidazole, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta [a]phenanthren-3-yl 3-(1H-imidazol-4-yl)propanoate, as represented by structure (I) below. In certain embodiments, a lipid nanoparticle for delivery of RNA (e.g., mRNA) encoding a functional protein may comprise one or more imidazole-based cationic lipids, for example, the imidazole cholesterol ester or "ICE" lipid (3S, 10R, 13R, 17R)-10, 13-dimethyl-17-((R)-6-methylheptan-2-yl)-2, 3, 4, 7, 8, 9, 10, 11, 12, 13, 14, 15, 16, 17-tetradecahydro-1H-cyclopenta [a]phenanthren-3-yl 3-(1H-imidazol-4-yl)propanoate, as represented by the following structure:

(ICE)

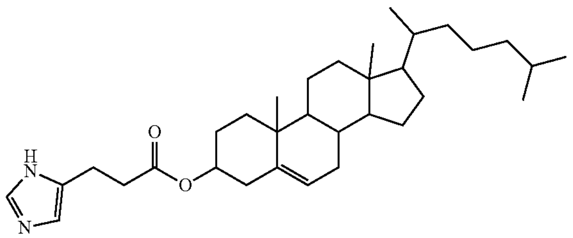

In some embodiments, the percentage of cationic lipid in a liposome may be greater than 10%, greater than 20%, greater than 30%, greater than 40%, greater than 50%, greater than 60%, or greater than 70%. In some embodiments, cationic lipid(s) constitute(s) about 30-50% (e.g., about 30-45%, about 30-40%, about 35-50%, about 35-45%, or about 35-40%) of the liposome by weight. In some embodiments, the cationic lipid (e.g., ICE lipid) constitutes about 30%, about 35%, about 40%, about 45%, about 50%, about 60%, about 70% or about 80% of the liposome by molar ratio.

PEGylated Lipids

In some embodiments, a suitable lipid solution includes one or more PEGylated lipids. For example, the use of polyethylene glycol (PEG)-modified phospholipids and derivatized lipids such as derivatized ceramides (PEG-CER), including N-Octanoyl-Sphingosine-1-[Succinyl (Methoxy Polyethylene Glycol)-2000] (C8 PEG-2000 ceramide) is also contemplated by the present invention. Contemplated PEG-modified lipids include, but are not limited to, a polyethylene glycol chain of up to 5 kDa in length covalently attached to a lipid with alkyl chain(s) of $C_6$-$C_{20}$ length. In some embodiments, a PEG-modified or PEGylated lipid is PEGylated cholesterol or PEG-2K. In some embodiments, particularly useful exchangeable lipids are PEG-ceramides having shorter acyl chains (e.g., $C_{14}$ or $C_{18}$).

PEG-modified phospholipid and derivatized lipids may constitute at least 1%, at least 2%, at least 3%, at least 4%, at least 5%, at least 6%, at least 7%, at least 8%, at least 9%, at least 10%, at least 15% or at least 20% of the total lipids in the liposome.

Non-Cationic/Helper Lipids

As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), or a mixture thereof.

In some embodiments, non-cationic lipids may constitute at least about 5%, 10%, 15%, 20%, 25%, 30%, 35%, 40%, 45%, 50%, 55%, 60%, 65% or 70% of the total lipids in a suitable lipid solution by weight or by molar. In some embodiments, non-cationic lipid(s) constitute(s) about 20-50% (e.g., about 20-45%, about 20-40%, about 25-50%, about 25-45%, or about 25-40%) of the total lipids in a suitable lipid solution by weight or by molar percent.

Cholesterol-Based Lipids

In some embodiments, a suitable lipid solution includes one or more cholesterol-based lipids. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, cholesterol-based lipid(s) constitute(s) at least about 1%, 5%, 10%, 20%, 30%, 40%, 50%, 60%, or 70% of the total lipids in a suitable lipid solution by weight or by molar. In some embodiments, cholesterol-based lipid(s) constitute(s) about 20-50% (e.g., about 20-45%, about 20-40%, about 25-50%, about 25-45%, or about 25-40%) of the total lipids in a suitable lipid solution by weight or by molar.

Exemplary combinations of cationic lipids, non-cationic lipids, cholesterol-based lipids, and PEG-modified lipids are described in the Examples section. For example, a suitable lipid solution may contain cKK-E12, DOPE, cholesterol, and DMG-PEG2K; C12-200, DOPE, cholesterol, and DMG-PEG2K; HGT5000, DOPE, cholesterol, and DMG-PEG2K; HGT5001, DOPE, cholesterol, and DMG-PEG2K; cKK-E12, DPPC, cholesterol, and DMG-PEG2K; C12-200, DPPC, cholesterol, and DMG-PEG2K; HGT5000, DPPC, cholesterol, and DMG-PEG2K; or HGT5001, DPPC, cholesterol, and DMG-PEG2K. The selection of cationic lipids, non-cationic lipids and/or PEG-modified lipids which comprise the lipid mixture as well as the relative molar ratio of such lipids to each other, is based upon the characteristics of the selected lipid(s) and the nature of the and the characteristics of the mRNA to be encapsulated. Additional considerations include, for example, the saturation of the alkyl chain, as well as the size, charge, pH, pKa, fusogenicity and toxicity of the selected lipid(s). Thus, the molar ratios may be adjusted accordingly.

Typically, mRNA-loaded lipid nanoparticles make up from 0.1% to 30% of the total solid content of the spray-drying mixture. In some embodiments, the total solid content of the mRNA-loaded nanoparticle compositions to be spray-dried is between 0.5-20%. In some embodiments, the total solid content of the mRNA-loaded nanoparticle compositions to be spray-dried is between 2-20%. In some embodiments, the total solid content of the mRNA-loaded nanoparticle compositions to be spray-dried is between 2-15%. In some embodiments, the total solid content of the mRNA-loaded nanoparticle compositions to be spray-dried is between 2-10%.

Polymer

Various polymers may be used in a spray-drying mRNA-LNP according to the present invention. Typically, suitable polymers have low toxicity and are well tolerated over a wide range of concentrations. In some embodiments, suitable polymers are positively charged. Exemplary polymers include, but are not limited to, chitosan, polyesters, polyurethanes, polycarbonates, poly(lactic acid) (PLA), poly(lactic-co-glycolic acid) (PLGA), poly(q-caprolactone (PCL), poly amido amines, poly(hydroxyalkyl L-asparagine), poly(hydroxyalkyl L-glutamine), poly(2-alkyloxazoline) acrylates, modified acrylates and methacrylate based polymers, poly-N-(2-hydroxyl-propyl)methacrylamide, poly-2-(methacryloyloxy)ethyl phosphorylcholines, poly(2-(methacryloyloxy)ethyl phosphorylcholine), and poly(dimethylaminoethyl methylacrylate) (pDMAEMA).

In some embodiments, a suitable polymer is a polymethacrylate derivative, comprising repeat units of a monomer of the following structure,

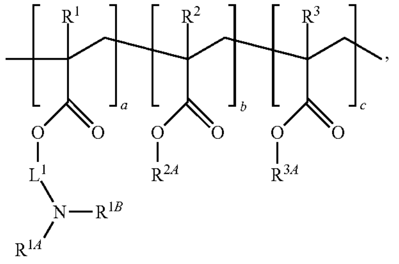

wherein, $R^1$ is independently $C_1$-$C_6$ alkyl, $L^1$ is independently $C_2$-$C_6$ alkylene, each of $R^{1A}$ and $R^{1B}$ is independently $C_1$-$C_6$ alkyl, and a is an integer of 1-500; $R^2$ is independently $C_1$-$C_6$ alkyl, $R^{2A}$ is independently $C_1$-$C_6$ alkyl, and b is an integer of 1-500; and $R^3$ is independently $C_1$-$C_6$ alkyl, $R^{3A}$ is independently $C_1$-$C_6$ alkyl, and c is an integer of 1-500.

In some embodiments, the repeat units may be represented by the following,

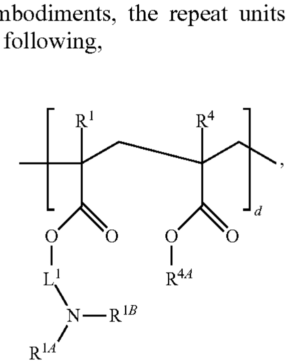

wherein each $R^4$ is independently $R^2$ or $R^3$; each $R^{4A}$ is independently $R^{2A}$ or $R^{3A}$; and d is an integer of 1-500. In the above structures, $L^1$ may be $—CH_2CH_2$, and each $R^{1A}$ and $R^{1B}$ is methyl; and/or each $R^1$, $R^2$, and $R^3$ is methyl; and/or $R^{2A}$ is butyl and $R^{3A}$ is methyl.

In some embodiments, an exemplary member of the polymer is represented by the formula:

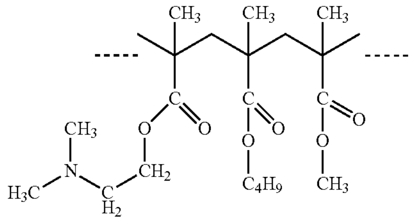

An exemplary member of the group is known by the trade name Eudragit. In some embodiments of the present invention, the polymer that is included in the spray-dried mRNA-LNP formulation is a Eudragit polymer. Eudragit forms a class of amorphous polymers or copolymers are derived from esters of acrylic and methacrylic acid, whose properties are determined by the functional groups. The individual Eudragit grades differ in their proportion of neutral, alkaline or acid groups and thus in terms of physicochemical properties. Some available forms are anionic, some are cationic, some are neutral. In some embodiments, polymers of this type used with mRNA-LNP complex for spray-drying have positively charged tertiary amine group with methacrylic back bone. They may form complex with mRNA and encapsulate it. They have a higher Tg and excellent thermoplastic properties which assist in spray drying. These polymers are insoluble at higher pH and in surfactants therefore may assist protecting mRNA from degradation. Eudragit polymers have been approved by the Food and Drug Authority of the United States of America (FDA) for oral use and have been used in commercial oral products for decades. These polymers have low toxicity and are well tolerated over a range of concentrations.

In some embodiments, the polymer used comprises the class of Eudragit that is insoluble at pH 5 and above. In some embodiments, this property of the polymer is used for oral delivery of the active mRNA ingredient such that the mRNA is not released in the saliva. One advantage of these polymers is that they powerfully mask the taste and odor of the active ingredients and other excipients because the functional polymer is insoluble in the mouth.

Therefore, in some embodiments, these methacrylic acid derivative polymers described above are used for preparing a formulation for stable spray-dried mRNA-LNP dry powder. In some embodiments, these methacrylic acid derivative polymers are used for sustained release of the mRNA. In some embodiments, the methacrylic acid derivative polymers insoluble at pH≥5 are used for delivery of the suitable mRNA to the gastrointestinal tract (GI). In some embodiments, the methacrylic acid derivative polymers are used for delivery of a suitable mRNA to the colon.

In some embodiments, the polymer constitutes less than 90%, 80%, 70%, 60%, 50%, 40%, 30%, 20%, 15%, 12%, 10%, 9%, 8%, 7%, 6% or 5% of the total weight of dry powder. In some embodiments, the polymer constitutes from 1% to 60% of the total weight of dry powder. In some embodiments, the polymer constitutes about 1-90%, 10-90%, 20-90%, 10-50%, 1-20%, 2-15%, 3-12%, 1-10%, 2-9%, 3-8%, 1-7%, 2-6% or 3-5% of the total weight of dry powder.

Other Excipients

In some embodiments, sugars and other excipients are added to the mRNA-loaded nanoparticles and polymer mixture before spray drying.

Sugars

Various sugars may be added to the mixture prior to spray drying. It is contemplated that sugars provide stabilization during dehydration. Exemplary sugars suitable for the formulation are monosaccharides, disaccharides and polysaccharides, selected from a group consisting of glucose, fructose, galactose, mannose, sorbose, lactose, sucrose, cellobiose, trehalose, raffinose, starch, dextran, maltodextrin, cyclodextrins, inulin, xylitol, sorbitol, lactitol, and mannitol.

In some embodiments, a suitable sugar is lactose and/or mannitol. In some embodiments, a suitable sugar is mannitol. In some embodiments, the mannitol is added at a concentration of about 1-10%. In some embodiments, the mannitol is added at a concentration of about 2-10%. In some embodiments, the mannitol is added at a concentration of about 3-10%. In some embodiments, the mannitol is added at a concentration of about 4-10%. In some embodiments, the mannitol is added at a concentration of about 5-10%.

In some embodiments, a suitable sugar is trehalose. In some embodiments, both mannitol and trehalose are added.

Surfactants

In some embodiments, surfactants are used as an excipient. Surfactants increase the surface tension of a composition. In some embodiments, the surfactants used in spray-drying mRNA lipid compositions are selected from a group consisting of CHAPS (3-[(3-Cholamidopropyl)dimethylammonio]-1-propanesulfonate), phospholipids, phosphatidylserine, phosphatidylethanolamine, phosphatidylcholine, sphingomyelins, octaethylene glycol monododecyl ether, pentaethylene glycol monododecyl ether, Triton X-100, Cocamide monoethanolamine, Cocamide diethanolamine, Glycerol monostearate, Glycerol monolaurate, Sorbitan moonolaureate, Sorbitan monostearate, Tween 20, Tween 40, Tween 60, Tween 80, Alkyl polyglucosides, and poloxamers. In some embodiments, the surfactant used is poloxamer.

Various other excipients may be included in the spray-drying formulations. These include but are not limited to various Polyesters, Polyurethanes, Poly (ester amide), Poly (ortho esters), Polyanhydrides, Poly (anhydride-co-imide), Polyphosphoesters, Polyphosphazenes, Amino acids, Collagen, Chitosan, Cyclodextrins, Polysaccharides, Maltodextrin, Albumin, various sugars, surfactants, buffers and salts.

Dry Powders

Dry powders prepared according to the present invention contain a plurality of spray-dried particles. Residual moisture content, aerosol performance and physio-chemical stability are important parameters for spray-dried pharmaceutical products. It is determined by the sample weight loss after heating and drying, using the equation:

$$\text{Moisture content } \%=[(SW_b-SW_a)/SW_b]\times100\%,$$

wherein, $SW_b$ is the sample weight before heating and $SW_a$ is the sample weight after heating. Perkin Elmer TGA 7 (Perkin Elmer) is an example of commercially used instrument with associated software for the measurement of residual moisture in a nanoparticle.

In general, an admissible range of particle size distribution is maintained for uniformity of dosing of an active pharmaceutical ingredient of the formulation. For pulmonary delivery in particular, the particles of the dry powder formulation affect distribution and deposition of an aerosol within the respiratory system. In many cases, particle deposition to the large conducting airways is preferred for effective absorption and distribution of the therapeutic component. Aerosol of very fine particles, for instance, particles having less than 1 micrometer diameter may be deposited peripherally for effective absorption by specific cells of the lung, such as smooth muscles for an active pharmaceutical ingredient functioning as bronchodilator.

Primary particle size distributions of spray-dried particles are measured by dynamic light scattering, which is expressed in terms of Z-average. The Z-average is the mean, also known as the cumulant size, calculated from the intensity-weighted distribution of particle diameter and is given by the formula, $D_z=\Sigma S_i/\Sigma(S_i/D_i)$, where, $S_i$ is the scattered intensity from the particle 'i', and $D_i$ is the particle's diameter. In addition to these parameters, a fine and a course fraction of the particles is defined.

Polydispersity index (PDI), on the other hand is the measure of the distribution of molecular mass of a given particulate sample.

Zeta potential is a measure of the magnitude of the electrostatic or charge repulsion/attraction between particles and is one of the fundamental parameters known to affect stability. Its measurement brings detailed insight into the causes of dispersion, aggregation or flocculation, and can be applied to improve the formulation of dispersions, emulsions and suspensions. The ZP indicates the degree of repulsion between close and similarly charged particles in the dispersion. High ZP indicates highly charged particles. Generally, high ZP (negative or positive) prevents aggregation of the particles due to electric repulsion and electrically stabilizes the nanoparticle dispersion. On the other hand, in case of low ZP, attraction exceeds repulsion and the dispersion coagulates or flocculates. Zeta potential can be measured by photon correlation spectroscopy using available equipment systems, for example, Zetasizer Nano (Malvern Instruments).

Sphericity of a nanoparticle is a measure of how closely a particle reassembles a sphere. It can be measured by Waddell's equation, denoted by Ψ is determined as:

$$\frac{\text{surface area of a sphere having a same volume of a given particle}}{\text{surface area of the particle}}$$

The size distribution as well as shape or sphericity of the spray-dried mRNA-lipid formulation is measurable by scanning electron microcopy (SEM), transmission electron microscope or a by change in electrical resistance imposed by a particle in a fluid by a Coulter counter.

Lastly, the content and/or integrity of the mRNA is assessed by HPLC, or northern blot analysis. In some embodiments, mass spectrometry and other related spectrophotochemical analysis are carried on for the stability, integrity and quality assessment of the mRNA-nanoparticle formulation.

Spray-dried mRNA lipid nanoparticles of the present invention contain less than 10% of moisture (w/w). In some embodiments, the spray-dried mRNA lipid nanoparticles of the invention may retain less than about 9% of moisture. In some embodiments, the spray-dried mRNA lipid nanoparticles of the invention may retain less than about 8% of moisture. In some embodiments, the spray-dried mRNA lipid nanoparticles of the invention may retain less than about 7% of moisture. In some embodiments, the spray-dried mRNA lipid nanoparticles of the invention may retain less than about 6% of moisture. In some embodiments, the spray-dried mRNA lipid nanoparticles of the invention may retain less than about 5% of moisture. In some embodiments, the spray-dried mRNA lipid nanoparticles of the invention may retain less than about 4% of moisture. In some embodiments, the spray-dried mRNA lipid nanoparticles of the invention may retain less than about 3% of moisture. In some embodiments, the spray-dried mRNA lipid nanoparticles of the invention may retain less than about 2% of moisture. In some embodiments, the spray-dried mRNA lipid nanoparticles of the invention may retain less than about 1% of moisture. In some embodiments the moisture content of the spray-dried mRNA-LNP formulation is less than 5%.

Provided herein are spray-dried mRNA LNP formulations, wherein the mRNA lipid nanoparticles are heterogeneous in size, with fine fraction (fnfr) less than 10 μm. In some embodiments, the fnfr of the mRNA-LNP dry-powder particles of the invention ranges between 1-10 μm. An optimum Z-average for an mRNA-LNP spray-dried sample could be ≤10 μm. In some embodiments, the Z-average of the mRNA-LNP spray-dried sample is ≤8 μm. In some embodiments, the Z-average of the mRNA-LNP spray-dried sample is ≤5 μm. In some embodiments, the Z-average of the mRNA-LNP spray-dried sample should be within a range of 0.01-10 μm. In some embodiments, the Z-average of the mRNA-LNP spray-dried sample should be within a range of 0.1-10 μm. In some embodiments, the Z-average of the mRNA-LNP spray-dried sample should be within a range of 0.1-5 μm. In some embodiments, the Z-average of the mRNA-LNP spray-dried sample should be within a range of 0.1-3 μm. In some embodiments, the Z-average of the mRNA-LNP spray-dried sample should be within a range of 0.1-5 μm.

In some embodiments, the mRNA-lipid nanoparticles comprise a Z-average of less than 200 nm before spray-drying. In some embodiments, the mRNA-lipid nanoparticles comprise a Z-average of less than 180 nm before spray-drying. In some embodiments, the mRNA-lipid nanoparticles comprise a Z-average of less than 150 nm before spray-drying. In some embodiments, the mRNA-lipid nanoparticles comprise a Z-average of less than 120 nm before spray-drying. In some embodiments, the mRNA-lipid nanoparticles comprise a Z-average of less than 100 nm before spray-drying. In some embodiments, the mRNA-lipid nanoparticles comprise a Z-average of less than 50 nm before spray-drying.

In some embodiments, mRNA-lipid nanoparticles comprise a Z-average of less than 5000 nm after spray-drying. In some embodiments, mRNA-lipid nanoparticles comprise a Z-average of less than 4000 nm after spray-drying. In some embodiments, mRNA-lipid nanoparticles comprise a Z-average of less than 3000 nm after spray-drying. In some embodiments, mRNA-lipid nanoparticles comprise a Z-average of less than 2000 nm after spray-drying. In some embodiments, mRNA-lipid nanoparticles comprise a Z-average of less than 1000 nm after spray-drying. In some embodiments, mRNA-lipid nanoparticles comprise a Z-average of less than 500 nm after spray-drying. In some embodiments, mRNA-lipid nanoparticles comprise a Z-average of less than 500 nm after spray-drying. In some embodiments, mRNA-lipid nanoparticles comprise a Z-average of less than 300 nm after spray-drying. In some embodiments, mRNA-lipid nanoparticles comprise a Z-average of less than 200 nm after spray-drying. In some embodiments, mRNA-lipid nanoparticles comprise a Z-average of less than 100 nm after spray-drying. In some embodiments, mRNA-lipid nanoparticles comprise a Z-average of less than 50 nm after spray-drying. In some embodiments, mRNA-lipid nanoparticles comprise a Z-average of less than 10 nm after spray-drying.

Provided herein are dry-powder formulations of mRNA-LNP, wherein the average sphericity of the mRNA-LNP particle ranges from 0.7 to 1. In some embodiments, the average sphericity of mRNA lipid nanoparticles is greater than 0.7, or greater than 0.8, or greater than 0.9.

In some embodiments, the Zeta potential value for the nanoparticles for present application is between +30 mV and −30 mV. In some embodiments, the Zeta potential value for the nanoparticles is between +20 mV and −30 mV. In some embodiments, the Zeta potential value for the nanoparticles is between +10 mV and −30 mV. In some embodiments, the Zeta potential value for the nanoparticles is between 0 mV and −30 mV. In some embodiments, the Zeta potential value for the nanoparticles is between −10 mV and −30 mV. In some embodiments, the Zeta potential value for the nanoparticles is between −20 mV and −30 mV. In some embodiments, the Zeta potential value for the nanoparticles is between +20 mV and −30 mV. In some embodiments, the Zeta potential value for the nanoparticles is between −20 mV and −30 mV. In some embodiments, the Zeta potential value for the nanoparticles is about −30 mV, and a polydispersity index of less than, about 0.3.

In some embodiments, provided dry-powder formulations of mRNA-LNP contain mRNA up to 30%, 20%, 15%, 10%, 9%, 8%, 7%, 6%, 5%, 4%, 3%, or 2% of the total weight of dry powder. In some embodiments, the mRNA constitutes 1-6%, 1-5%, 1-4%, 1-3%, 2-10%, 2-9%, 2-8%, 2-7%, 2-6%, 2-5%, 2-10%, 2-15%, 2-20%, 2-30% of the total weight of dry powder.

Stability

Provided are spray-dried mRNA-LNP formulations that are stable when stored under various conditions. As used herein, the term "stable" refers to mRNA retaining integrity of greater than 70%, 75%, 80%, 85%, 90%, 95%, 96%, 97%, 98%, or 99% after storage. In some embodiments, mRNA-LNP dry powder formulations provided herein are stable when stored under frozen condition (−20° C.), at 4° C. or at room temperature for greater than one year. In some embodiments, mRNA-LNP dry powder formulations provided herein are stable when stored under frozen condition (−20° C.), at 4° C. or at room temperature for greater than 11 months. In some embodiments, mRNA-LNP dry powder formulations provided herein are stable when stored under frozen condition (−20° C.), at 4° C. or at room temperature for greater than 10 months. In some embodiments, mRNA-LNP dry powder formulations provided herein are stable when stored under frozen condition (−20° C.), at 4° C. or at room temperature for greater than 9 months. In some embodiments, mRNA-LNP dry powder formulations provided herein are stable when stored under frozen condition (−20° C.), at 4° C. or at room temperature for greater than 8 months. In some embodiments, mRNA-LNP dry powder formulations provided herein are stable when stored under frozen condition (−20° C.), at 4° C. or at room temperature for greater than 7 months. In some embodiments, mRNA-LNP dry powder formulations provided herein are stable when stored under frozen condition (−20° C.), at 4° C. or at room temperature for greater than 6 months. In some embodiments, mRNA-LNP dry powder formulations provided herein are stable when stored under frozen condition (−20° C.), at 4° C. or at room temperature for greater than 5 months. In some embodiments, mRNA-LNP dry powder formulations provided herein are stable when stored under frozen condition (−20° C.), at 4° C. or at room temperature for greater than 4 months. In some embodiments, mRNA-LNP dry powder formulations provided herein are stable when stored under frozen condition (−20° C.), at 4° C. or at room temperature for greater than 3 months. In some embodiments, mRNA-LNP dry powder formulations provided herein are stable when stored under frozen condition (−20° C.), at 4° C. or at room temperature for greater than 2 months. In some embodiments, mRNA-LNP dry powder formulations provided herein are stable when stored under frozen condition (−20° C.), at 4° C. or at room temperature for greater than 1 month.

In some embodiments, mRNA-LNP dry powder formulations provided herein are stable when stored under frozen condition (−20° C.), at 4° C. or at room temperature for greater than 8 weeks. In some embodiments, mRNA-LNP dry powder formulations provided herein are stable when stored under frozen condition (−20° C.), at 4° C. or at room temperature for greater than 7 weeks. In some embodiments, mRNA-LNP dry powder formulations provided herein are stable when stored under frozen condition (−20° C.), at 4° C. or at room temperature for greater than 6 weeks. In some embodiments, mRNA-LNP dry powder formulations provided herein are stable when stored under frozen condition (−20° C.), at 4° C. or at room temperature for greater than 5 weeks. In some embodiments, mRNA-LNP dry powder formulations provided herein are stable when stored under frozen condition (−20° C.), at 4° C. or at room temperature for greater than 4 weeks.

Messenger RNA

The present invention may be used to formulate any mRNA. As used herein, mRNA is the type of RNA that carries information from DNA to the ribosome for translation of the encoded protein. mRNAs may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application.

The present invention may be used to formulate mRNAs of a variety of lengths. In some embodiments, the present invention may be used to deliver in vitro synthesized mRNA of or greater than about 1 kb, 1.5 kb, 2 kb, 2.5 kb, 3 kb, 3.5 kb, 4 kb, 4.5 kb, 5 kb 6 kb, 7 kb, 8 kb, 9 kb, 10 kb, 11 kb, 12 kb, 13 kb, 14 kb, 15 kb, or 20 kb in length. In some embodiments, the present invention may be used to deliver in vitro synthesized mRNA ranging from about 1-20 kb, about 1-15 kb, about 1-10 kb, about 5-20 kb, about 5-15 kb, about 5-12 kb, about 5-10 kb, about 8-20 kb, or about 8-15 kb in length.

The present invention may be used to formulate mRNA that is unmodified or mRNA containing one or more modifications that typically enhance stability. In some embodiments, modifications are selected from modified nucleotides, modified sugar phosphate backbones, and 5' and/or 3' untranslated region (UTR).

In some embodiments, modifications of mRNA may include modifications of the nucleotides of the RNA. A modified mRNA according to the invention can include, for example, backbone modifications, sugar modifications or base modifications. In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydrouracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosure of which is included here in its full scope by reference.

In some embodiments, mRNAs may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g. cytidine 5'-O-(1-thiophosphate)), boranophosphates, positively charged guanidinium groups etc., which means by replacing the phosphodiester linkage by other anionic, cationic or neutral groups.

In some embodiments, mRNAs may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

In some embodiments, mRNAs may contain modifications of the bases of the nucleotides (base modifications). A modified nucleotide which contains a base modification is also called a base-modified nucleotide. Examples of such base-modified nucleotides include, but are not limited to, 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, 06-methylguanosine 5'-triphosphate, pseudouridine 5'-triphosphate, puromycin 5'-triphosphate or xanthosine 5'-triphosphate.

Typically, mRNA synthesis includes the addition of a "cap" on the 5' end, and a "tail" on the 3' end. The presence of the cap is important in providing resistance to nucleases found in most eukaryotic cells. The presence of a "tail" serves to protect the mRNA from exonuclease degradation.

Thus, in some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'-5' inverted triphosphate linkage; and the 7-nitrogen of guanine is then methylated by a methyltransferase. 2'-O-methylation may also occur at the first base and/or second base following the 7-methyl guanosine triphosphate residues. Examples of cap structures include, but are not limited to, m7GpppNp-RNA, m7GpppNmp-RNA and m7GpppNmpNmp-RNA (where m indicates 2'-O-methyl residues).

In some embodiments, mRNAs include a 3' tail structure. Typically, a tail structure includes a poly(A) and/or poly(C) tail. A poly-A or poly-C tail on the 3' terminus of mRNA typically includes at least 50 adenosine or cytosine nucleotides, at least 150 adenosine or cytosine nucleotides, at least 200 adenosine or cytosine nucleotides, at least 250 adenosine or cytosine nucleotides, at least 300 adenosine or cytosine nucleotides, at least 350 adenosine or cytosine nucleotides, at least 400 adenosine or cytosine nucleotides, at least 450 adenosine or cytosine nucleotides, at least 500 adenosine or cytosine nucleotides, at least 550 adenosine or cytosine nucleotides, at least 600 adenosine or cytosine nucleotides, at least 650 adenosine or cytosine nucleotides, at least 700 adenosine or cytosine nucleotides, at least 750 adenosine or cytosine nucleotides, at least 800 adenosine or cytosine nucleotides, at least 850 adenosine or cytosine nucleotides, at least 900 adenosine or cytosine nucleotides, at least 950 adenosine or cytosine nucleotides, or at least 1 kb adenosine or cytosine nucleotides, respectively. In some embodiments, a poly-A or poly-C tail may be about 10 to 800 adenosine or cytosine nucleotides (e.g., about 10 to 200 adenosine or cytosine nucleotides, about 10 to 300 adenosine or cytosine nucleotides, about 10 to 400 adenosine or cytosine nucleotides, about 10 to 500 adenosine or cytosine nucleotides, about 10 to 550 adenosine or cytosine nucleotides, about 10 to 600 adenosine or cytosine nucleotides, about 50 to 600 adenosine or cytosine nucleotides, about 100 to 600 adenosine or cytosine nucleotides, about 150 to 600 adenosine or cytosine nucleotides, about 200 to 600 adenosine or cytosine nucleotides, about 250 to 600 adenosine or cytosine nucleotides, about 300 to 600 adenosine or cytosine nucleotides, about 350 to 600 adenosine or cytosine nucleotides, about 400 to 600 adenosine or cytosine nucleotides, about 450 to 600 adenosine or cytosine nucleotides, about 500 to 600 adenosine or cytosine nucleotides, about 10 to 150 adenosine or cytosine nucleotides, about 10 to 100 adenosine or cytosine nucleotides, about 20 to 70 adenosine or cytosine nucleotides, or about 20 to 60 adenosine or cytosine nucleotides) respectively. In some embodiments, a tail structure includes is a combination of poly(A) and poly(C) tails with various lengths described herein. In some embodiments, a tail structure includes at least 50%, 55%, 65%, 70%, 75%, 80%, 85%, 90%, 92%, 94%, 95%, 96%, 97%, 98%, or 99% adenosine nucleotides. In some embodiments, a tail structure includes at least 50%, 55%, 65%, 70%, 75%, 80%, 85%, 90%, 92%, 94%, 95%, 96%, 97%, 98%, or 99% cytosine nucleotides.

In some embodiments, mRNAs include a 5' and/or 3' untranslated region. In some embodiments, a 5' untranslated region includes one or more elements that affect an mRNA's stability or translation, for example, an iron responsive element.

In some embodiments, a 3' untranslated region includes one or more of a polyadenylation signal, a binding site for proteins that affect an mRNA's stability of location in a cell, or one or more binding sites for miRNAs.

Exemplary 5' and/or 3' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

An mRNA construct design can be designated as X—Coding Sequence—Y. Exemplary X and Y nucleotide sequences are as follows:

```
                                    (SEQ ID NO: 1)
X (5' UTR Sequence) =
GGACAGAUCGCCUGGAGACGCCAUCCACGCUGUUUUGACCU

CCAUAGAAGACACCGGGACCGAUCCAGCCUCCGCGGCCGGG
```

-continued

```
AACGGUGCAUUGGAACGCGGAUUCCCCGUGCCAAGAGUGAC

UCACCGUCCUUGACACG

                                    (SEQ ID NO: 2)
Y (3' UTR Sequence) =
CGGGUGGCAUCCCUGUGACCCCUCCCCAGUGCCUCUCCUGG

CCCUGGAAGUUGCCACUCCAGUGCCCACCAGCCUUGUCCUA

AUAAAAUUAAGUUGCAUCAAGCU
OR

                                    (SEQ ID NO: 3)
GGGUGGCAUCCCUGUGACCCCUCCCCAGUGCCUCUCCUGGC

CCUGGAAGUUGCCACUCCAGUGCCCACCAGCCUUGUCCUAA

UAAAAUUAAGUUGCAUCAAAGCU
```

While mRNA provided from in vitro transcription reactions may be desirable in some embodiments, other sources of mRNA are contemplated as within the scope of the invention including mRNA produced from bacteria, fungi, plants, and/or animals.

In some embodiments, a suitable mRNA sequence is an mRNA sequence encoding a human cystic fibrosis transmembrane receptor, the Cystic Fibrosis Transmembrane Conductance Regulator CFTR (hCFTR) protein. In some embodiments, a suitable mRNA sequence is codon optimized for efficient expression human cells. A detailed description embodying the preparation and optimization of CFTR mRNA for therapeutic delivery is described in U.S. patent application Ser. No. 15/981,757, filed May 16, 2018, the disclosure of which is hereby incorporated in its entirety.

A. Pharmaceutical Formulations and Therapeutic Uses

Pharmaceutical compositions of the dry powder formulations of the present invention may be used in various therapeutic applications. To facilitate delivery in vivo, the dry powder formulations as described herein may be combined with one or more additional pharmaceutical carriers, targeting ligands or stabilizing reagents. In some embodiments, one or more additional pharmaceutical carriers may be added to the formulation prior to spray-drying. In some embodiments, one or more additional pharmaceutical carriers may be added to the formulation using post-insertion techniques into dry powder formulation (i.e., following spray drying). Techniques for formulation and administration of drugs may be found in "Remington's Pharmaceutical Sciences," Mack Publishing Co., Easton, Pa., latest edition.

The dry powder formulations described herein can be administered in vivo in powder form, or alternatively, following reconstitution. Suitable routes of administration for the formulations described herein include, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal. In particular embodiments, the intramuscular administration is to a muscle selected from the group consisting of skeletal muscle, smooth muscle and cardiac muscle. In some embodiments the administration results in delivery of the nucleic acids to a muscle cell. In some embodiments the administration results in delivery of the nucleic acids to a hepatocyte (i.e., liver cell).

The pharmaceutical formulations of the invention may be administered in a local rather than systemic manner, for example, via injection of the pharmaceutical formulation directly into a targeted tissue, preferably in a sustained release formulation. Local delivery can be affected in various ways, depending on the tissue to be targeted. Exemplary tissues in which delivered mRNA may be delivered and/or expressed include, but are not limited to the lungs, liver, kidney, heart, spleen, serum, brain, skeletal muscle, lymph nodes, skin, and/or cerebrospinal fluid. In embodiments, the tissue to be targeted in the liver. For example, aerosols containing compositions of the present invention can be inhaled (for nasal, tracheal, or bronchial delivery). In some embodiments, compositions of the present invention can be delivered using a metered dose inhaler. In some embodiments, compositions of the present invention can be reconstituted and nebulized for delivery. In some embodiments, compositions of the present invention can be injected into the site of injury, disease manifestation, or pain. In some embodiments, compositions of the present invention can be provided in lozenges for oral, tracheal, or esophageal applications. In some embodiments, compositions of the present invention can be supplied in liquid, tablet or capsule form for administration to the stomach or intestines. In some embodiments, compositions of the present invention can be supplied in suppository form for rectal or vaginal application. In some embodiments, compositions of the present invention can be delivered to the eye by use of creams, drops, or even injection.

In some embodiments, a dry powder formulation of the present invention is reconstituted into a liquid solution and nebulized for delivery. Nebulization can be achieved by any nebulizer known in the art. A nebulizer transforms a liquid to a mist so that it can be inhaled more easily into the lungs. Nebulizers are effective for infants, children and adults. Nebulizers are able to nebulize large doses of inhaled medications. Typically, a nebulizer for use with the invention comprises a mouthpiece that is detachable.

In some embodiments, dry powder formulations as described herein may be used to deliver a therapeutically effective amount of mRNA for the treatment of various diseases or disorders. For example, the dry powder formulation prepared by spray-drying according to the present invention can be administered for treatment of a lung-related disorder, such as cystic fibrosis, via oral, nasal, tracheal, or pulmonary or routes. In some embodiments, the dry powder formulation is administered by inhalation. In some embodiments, the formulation is administered by a metered-dose inhaler. In some embodiments, the dry powder formulation is administered by intranasal spray. In some embodiments, the dry powder formulation is rehydrated and administered as intravenous infusions, injections, oral drops, nasal drops and any other applications as easily conceivable by one of ordinary skill in the art.

The present invention may be used to treat various other lung-related diseases, disorders and conditions. In some embodiments, the present invention of stable dry powder formulation is useful in treating one or more of asthma; COPD; emphysema; primary ciliary dyskinesia (CILD1) with or without situs inversus, or Kartagener syndrome; pulmonary fibrosis; Birt-Hogg-Dube syndrome; hereditary hemorrhagic telangiectasia; alpha-1 antitrypsin deficiency; Cytochrome b positive granulomatous diseases (CGD, X-lined); Cytochrome b positive granulomatous diseases, autosomal recessive; surfactant deficiency diseases, Pulmonary Surfactant Metabolism Dysfunction 1, Pulmonary Surfactant Metabolism Dysfunction 2, Pulmonary Surfactant Metabolism Dysfunction 3; Respiratory distress syndrome of prematurity; tuberculous tuberculosis, lung viral diseases, including influenza, and Respiratory Syncytial Virus (RSV).

Accordingly, in certain embodiments, the present invention provides a method for producing a dry powder composition comprising full-length mRNA that encodes a peptide or polypeptide for use in the delivery to or treatment of the lung of a subject or a lung cell. In certain embodiments, the present invention provides a method for producing a dry powder composition having full-length mRNA that encodes for cystic fibrosis transmembrane conductance regulator (CFTR) protein. In certain embodiments, the present invention provides a method for producing a dry powder composition having full-length mRNA that encodes for ATP-binding cassette sub-family A member 3 protein. In certain embodiments, the present invention provides a method for producing a dry powder composition having full-length mRNA that encodes for dynein axonemal intermediate chain 1 protein. In certain embodiments, the present invention provides a method for producing a dry powder composition having full-length mRNA that encodes for dynein axonemal heavy chain 5 (DNAH5) protein. In certain embodiments, the present invention provides a method for producing a dry powder composition having full-length mRNA that encodes for alpha-1-antitrypsin protein. In certain embodiments, the present invention provides a method for producing a dry powder composition having full-length mRNA that encodes for forkhead box P3 (FOXP3) protein. In certain embodiments, the present invention provides a method for producing a dry powder composition having full-length mRNA that encodes one or more surfactant protein, e.g., one or more of surfactant A protein, surfactant B protein, surfactant C protein, and surfactant D protein.

In certain embodiments, the present invention provides a method for producing a dry powder composition having full-length mRNA that encodes a peptide or polypeptide for use in the delivery to or treatment of the liver of a subject or a liver cell. Such peptides and polypeptides can include those associated with a urea cycle disorder, associated with a lysosomal storage disorder, with a glycogen storage disorder, associated with an amino acid metabolism disorder, associated with a lipid metabolism or fibrotic disorder, associated with methylmalonic acidemia, or associated with any other metabolic disorder for which delivery to or treatment of the liver or a liver cell with enriched full-length mRNA provides dry powder benefit.

In certain embodiments, the present invention provides a method for producing a dry powder composition having full-length mRNA that encodes for a protein associated with a urea cycle disorder. In certain embodiments, the present invention provides a method for producing a dry powder composition having full-length mRNA that encodes for ornithine transcarbamylase (OTC) protein. In certain embodiments, the present invention provides a method for producing a dry powder composition having full-length mRNA that encodes for arginosuccinate synthetase 1 protein. In certain embodiments, the present invention provides a method for producing a dry powder composition having full-length mRNA that encodes for carbamoyl phosphate synthetase I protein. In certain embodiments, the present invention provides a method for producing a dry powder composition having full-length mRNA that encodes for arginosuccinate lyase protein. In certain embodiments, the present invention provides a method for producing a dry powder composition having full-length mRNA that encodes for arginase protein.

In certain embodiments, the present invention provides a method for producing a dry powder composition having full-length mRNA that encodes for a protein associated with a lysosomal storage disorder. In certain embodiments, the present invention provides a method for producing a dry powder composition having full-length mRNA that encodes for alpha galactosidase protein. In certain embodiments, the present invention provides a method for producing a dry powder composition having full-length mRNA that encodes for glucocerebrosidase protein. In certain embodiments, the present invention provides a method for producing a dry powder composition having full-length mRNA that encodes for iduronate-2-sulfatase protein. In certain embodiments, the present invention provides a method for producing a dry powder composition having full-length mRNA that encodes for iduronidase protein. In certain embodiments, the present invention provides a method for producing a therapeutic composition having full-length mRNA that encodes for N-acetyl-alpha-D-glucosaminidase protein. In certain embodiments, the present invention provides a method for producing a dry powder composition having full-length mRNA that encodes for heparan N-sulfatase protein. In certain embodiments, the present invention provides a method for producing a dry powder composition having full-length mRNA that encodes for galactosamine-6 sulfatase protein. In certain embodiments, the present invention provides a method for producing a dry powder composition having full-length mRNA that encodes for beta-galactosidase protein. In certain embodiments, the present invention provides a method for producing a dry powder composition having full-length mRNA that encodes for lysosomal lipase protein. In certain embodiments, the present invention provides a method for producing a dry powder composition having full-length mRNA that encodes for arylsulfatase B (N-acetylgalactosamine-4-sulfatase) protein. In certain embodiments, the present invention provides a method for producing a dry powder composition having full-length mRNA that encodes for transcription factor EB (TFEB).

In certain embodiments, the present invention provides a method for producing a dry powder composition having full-length mRNA that encodes for a protein associated with a glycogen storage disorder. In certain embodiments, the present invention provides a method for producing a dry powder composition having full-length mRNA that encodes for acid alpha-glucosidase protein. In certain embodiments, the present invention provides a method for producing a dry powder composition having full-length mRNA that encodes for glucose-6-phosphatase (G6PC) protein. In certain embodiments, the present invention provides a method for producing a dry powder composition having full-length mRNA that encodes for liver glycogen phosphorylase protein. In certain embodiments, the present invention provides a method for producing a dry powder composition having full-length mRNA that encodes for muscle phosphoglycerate mutase protein. In certain embodiments, the present invention provides a method for producing a dry powder composition having full-length mRNA that encodes for glycogen debranching enzyme.

In certain embodiments, the present invention provides a method for producing a dry powder composition having full-length mRNA that encodes for a protein associated with amino acid metabolism. In certain embodiments, the present invention provides a method for producing a dry powder composition having full-length mRNA that encodes for phenylalanine hydroxylase enzyme. In certain embodiments, the present invention provides a method for producing a dry powder composition having full-length mRNA that encodes for glutaryl-CoA dehydrogenase enzyme. In certain embodiments, the present invention provides a method for producing a dry powder composition having full-length mRNA that encodes for propionyl-CoA caboxylase enzyme. In certain embodiments the present invention provides a method for producing a dry powder composition having full-length mRNA that encodes for oxalase alanine-glyoxylate aminotransferase enzyme.

In certain embodiments, the present invention provides a method for producing a dry powder composition having full-length mRNA that encodes for a protein associated with a lipid metabolism or fibrotic disorder. In certain embodiments, the present invention provides a method for producing a dry powder composition having full-length mRNA that encodes for a mTOR inhibitor. In certain embodiments, the present invention provides a method for producing a dry powder composition having full-length mRNA that encodes for ATPase phospholipid transporting 8B1 (ATP8B1) protein. In certain embodiments, the present invention provides a method for producing a dry powder composition having full-length mRNA that encodes for one or more NF-kappa B inhibitors, such as one or more of I-kappa B alpha, interferon-related development regulator 1 (IFRD1), and Sirtuin 1 (SIRT1). In certain embodiments, the present invention provides a method for producing a dry powder composition having full-length mRNA that encodes for PPAR-gamma protein or an active variant.

In certain embodiments, the present invention provides a method for producing a dry powder composition having full-length mRNA that encodes for a protein associated with methylmalonic acidemia. For example, in certain embodiments, the present invention provides a method for producing a dry powder composition having full-length mRNA that encodes for methylmalonyl CoA mutase protein. In certain embodiments, the present invention provides a method for producing a dry powder composition having full-length mRNA that encodes for methylmalonyl CoA epimerase protein.

In certain embodiments, the present invention provides a method for producing a dry powder composition having full-length mRNA for which delivery to or treatment of the liver can provide dry powder benefit. In certain embodiments the present invention provides a method for producing a dry powder composition having full-length mRNA that encodes for ATP7B protein, also known as Wilson disease protein. In certain embodiments, the present invention provides a method for producing a dry powder composition having full-length mRNA that encodes for porphobilinogen deaminase enzyme. In certain embodiments the present invention provides a method for producing a dry powder composition having full-length mRNA that encodes for one or clotting enzymes, such as Factor VIII, Factor IX, Factor VII, and Factor X. In certain embodiments, the present invention provides a method for producing a dry powder composition having full-length mRNA that encodes for human hemochromatosis (HFE) protein.

In certain embodiments, the present invention provides a method for producing a dry powder composition having full-length mRNA that encodes a peptide or polypeptide for use in the delivery to or treatment of the cardiovasculature of a subject or a cardiovascular cell. In certain embodiments, the present invention provides a method for producing a dry powder composition having full-length mRNA that encodes for vascular endothelial growth factor A protein. In certain embodiments, the present invention provides a method for producing a dry powder composition having full-length mRNA that encodes for relaxin protein. In certain embodiments, the present invention provides a method for producing a dry powder composition having full-length mRNA that encodes for bone morphogenetic protein-9 protein. In certain embodiments, the present invention provides a method for producing a dry powder composition having full-length mRNA that encodes for bone morphogenetic protein-2 receptor protein.

In certain embodiments, the present invention provides a method for producing a dry powder composition having full-length mRNA that encodes a peptide or polypeptide for use in the delivery to or treatment of the muscle of a subject or a muscle cell. In certain embodiments, the present invention provides a method for producing a dry powder composition having full-length mRNA that encodes for dystrophin protein. In certain embodiments, the present invention provides a method for producing a dry powder composition having full-length mRNA that encodes for frataxin protein. In certain embodiments, the present invention provides a method for producing a dry powder composition having full-length mRNA that encodes a peptide or polypeptide for use in the delivery to or treatment of the cardiac muscle of a subject or a cardiac muscle cell. In certain embodiments, the present invention provides a method for producing a dry powder composition having full-length mRNA that encodes for a protein that modulates one or both of a potassium channel and a sodium channel in muscle tissue or in a muscle cell. In certain embodiments, the present invention provides a method for producing a dry powder composition having full-length mRNA that encodes for a protein that modulates a Kv7.1 channel in muscle tissue or in a muscle cell. In certain embodiments, the present invention provides a method for producing a dry powder composition having full-length mRNA that encodes for a protein that modulates a Nav1.5 channel in muscle tissue or in a muscle cell.

In certain embodiments, the present invention provides a method for producing a dry powder composition having full-length mRNA that encodes a peptide or polypeptide for use in the delivery to or treatment of the nervous system of a subject or a nervous system cell. For example, in certain embodiments, the present invention provides a method for producing a dry powder composition having full-length mRNA that encodes for survival motor neuron 1 protein. For example, in certain embodiments, the present invention provides a method for producing a dry powder composition having full-length mRNA that encodes for survival motor neuron 2 protein. In certain embodiments, the present invention provides a method for producing a dry powder composition having full-length mRNA that encodes for frataxin protein. In certain embodiments, the present invention provides a method for producing a dry powder composition having full-length mRNA that encodes for ATP binding cassette subfamily D member 1 (ABCD1) protein. In certain embodiments, the present invention provides a method for producing a dry powder composition having full-length mRNA that encodes for CLN3 protein.

In certain embodiments, the present invention provides a method for producing a dry powder composition having full-length mRNA that encodes a peptide or polypeptide for use in the delivery to or treatment of the blood or bone marrow of a subject or a blood or bone marrow cell. In certain embodiments, the present invention provides a method for producing a dry powder composition having full-length mRNA that encodes for beta globin protein. In certain embodiments, the present invention provides a method for producing a dry powder composition having full-length mRNA that encodes for Bruton's tyrosine kinase protein. In certain embodiments, the present invention provides a method for producing a dry powder composition having full-length mRNA that encodes for one or clotting enzymes, such as Factor VIII, Factor IX, Factor VII, and Factor X.

In certain embodiments, the present invention provides a method for producing a dry powder composition having full-length mRNA that encodes a peptide or polypeptide for use in the delivery to or treatment of the kidney of a subject or a kidney cell. In certain embodiments, the present invention provides a method for producing a dry powder composition having full-length mRNA that encodes for collagen type IV alpha 5 chain (COL4A5) protein.

In certain embodiments, the present invention provides a method for producing a dry powder composition having full-length mRNA that encodes a peptide or polypeptide for use in the delivery to or treatment of the eye of a subject or an eye cell. In certain embodiments, the present invention provides a method for producing a dry powder composition having full-length mRNA that encodes for ATP-binding cassette sub-family A member 4 (ABCA4) protein. In certain embodiments, the present invention provides a method for producing a dry powder composition having full-length mRNA that encodes for retinoschisin protein. In certain embodiments, the present invention provides a method for producing a dry powder composition having full-length mRNA that encodes for retinal pigment epithelium-specific 65 kDa (RPE65) protein. In certain embodiments, the present invention provides a method for producing a dry powder composition having full-length mRNA that encodes for centrosomal protein of 290 kDa (CEP290).

In certain embodiments, the present invention provides a method for producing a dry powder composition having full-length mRNA that encodes a peptide or polypeptide for use in the delivery of or treatment with a vaccine for a subject or a cell of a subject. For example, in certain embodiments, the present invention provides a method for producing a dry powder composition having full-length mRNA that encodes for an antigen from an infectious agent, such as a virus. In certain embodiments, the present invention provides a method for producing a dry powder composition having full-length mRNA that encodes for an antigen from influenza virus. In certain embodiments, the present invention provides a method for producing a dry powder composition having full-length mRNA that encodes for an antigen from respiratory syncytial virus. In certain embodiments, the present invention provides a method for producing a dry powder composition having full-length mRNA that encodes for an antigen from rabies virus. In certain embodiments, the present invention provides a method for producing a dry powder composition having full-length mRNA that encodes for an antigen from cytomegalovirus. In certain embodiments, the present invention provides a method for producing a dry powder composition having full-length mRNA that encodes for an antigen from rotavirus. In certain embodiments, the present invention provides a method for producing a dry powder composition having full-length mRNA that encodes for an antigen from a hepatitis virus, such as hepatitis A virus, hepatitis B virus, or hepatitis C virus. In certain embodiments, the present invention provides a method for producing a dry powder composition having full-length mRNA that encodes for an antigen from human papillomavirus. In certain embodiments, the present invention provides a method for producing a dry powder composition having full-length mRNA that encodes for an antigen from a herpes simplex virus, such as herpes simplex virus 1 or herpes simplex virus 2. In certain embodiments, the present invention provides a method for producing a dry powder composition having full-length mRNA that encodes for an antigen from a human immunodeficiency virus, such as human immunodeficiency virus type 1 or human immunodeficiency virus type 2. In certain embodiments, the present invention provides a method for producing a dry powder composition having full-length mRNA that encodes for an antigen from a human metapneumovirus. In certain embodiments, the present invention provides a method for producing a dry powder composition having full-length mRNA that encodes for an antigen from a human parainfluenza virus, such as human parainfluenza virus type 1, human parainfluenza virus type 2, or human parainfluenza virus type 3. In certain embodiments, the present invention provides a method for producing a dry powder composition having full-length mRNA that encodes for an antigen from malaria virus. In certain embodiments, the present invention provides a method for producing a dry powder composition having full-length mRNA that encodes for an antigen from zika virus. In certain embodiments, the present invention provides a method for producing a dry powder composition having full-length mRNA that encodes for an antigen from chikungunya virus.

In certain embodiments, the present invention provides a method for producing a dry powder composition having full-length mRNA that encodes for an antigen associated with a cancer of a subject or identified from a cancer cell of a subject. In certain embodiments, the present invention provides a method for producing a dry powder composition having full-length mRNA that encodes for an antigen determined from a subject's own cancer cell, i.e., to provide a personalized cancer vaccine. In certain embodiments, the present invention provides a method for producing a dry powder composition having full-length mRNA that encodes for an antigen expressed from a mutant KRAS gene.

In certain embodiments, the present invention provides a method for producing a dry powder composition having full-length mRNA that encodes for an antibody. In certain embodiments, the antibody can be a bi-specific antibody. In certain embodiments, the antibody can be part of a fusion protein. In certain embodiments, the present invention provides a method for producing a dry powder composition having full-length mRNA that encodes for an antibody to OX40. In certain embodiments, the present invention provides a method for producing a dry powder composition having full-length mRNA that encodes for an antibody to VEGF. In certain embodiments, the present invention provides a method for producing a dry powder composition having full-length mRNA that encodes for an antibody to tissue necrosis factor alpha. In certain embodiments, the present invention provides a method for producing a dry powder composition having full-length mRNA that encodes for an antibody to CD3. In certain embodiments, the present invention provides a method for producing a dry powder composition having full-length mRNA that encodes for an antibody to CD19.

In certain embodiments, the present invention provides a method for producing a dry powder composition having full-length mRNA that encodes for an immunomodulator. In certain embodiments, the present invention provides a method for producing a dry powder composition having full-length mRNA that encodes for Interleukin 12. In certain embodiments, the present invention provides a method for producing a dry powder composition having full-length mRNA that encodes for Interleukin 23. In certain embodiments, the present invention provides a method for producing a dry powder composition having full-length mRNA that encodes for Interleukin 36 gamma. In certain embodiments, the present invention provides a method for producing a dry powder composition having full-length mRNA that encodes for a constitutively active variant of one or more stimulator of interferon genes (STING) proteins.

In certain embodiments, the present invention provides a method for producing a dry powder composition having full-length mRNA that encodes for an endonuclease. In certain embodiments, the present invention provides a method for producing a dry powder composition having full-length mRNA that encodes for an RNA-guided DNA endonuclease protein, such as Cas 9 protein. In certain embodiments the present invention provides a method for producing a dry powder composition having full-length mRNA that encodes for a meganuclease protein. In certain embodiments, the present invention provides a method for producing a dry powder composition having full-length mRNA that encodes for a transcription activator-like effector nuclease protein. In certain embodiments, the present invention provides a method for producing a dry powder composition having full-length mRNA that encodes for a zinc finger nuclease protein.

The present invention may be used to treat various other diseases, disorders and conditions in which sustained release of the mRNA formulation is required. These examples include diseases where the mRNA delivery in the digestive tract is useful. Such diseases include but are not limited to, Apolipoprotein E deficiency disease; Inflammatory Bowel Disease, or Crohn's disease; Adhesion G Protein-coupled Receptor VI deficiency disease; Type 2 Von Willebrand Disease; Nephrolithiasis, calcium oxalate CAON related; Maturity Onset Diabetes of the Young, Type 8.

The present invention may be used to treat various other diseases, disorders or conditions where targeted delivery of the mRNA formulation to a tissue or organ may be beneficial. These may be orchestrated by association of a polymer suitable for the purpose, with or without association of specific targeting moieties.

EXAMPLES

While certain compounds, compositions and methods of the present invention have been described with specificity in accordance with certain embodiments, the following examples serve only to illustrate the present invention and are not intended to limit the same.

Example 1. mRNA-LNP Dry Powder Formulations Recovered from Spray-Drying

In this example, LNP-encapsulated mRNA formulations were prepared with and without polymer and spray-dried. The results show that the LNP-encapsulated mRNA formulations prepared with polymer provides an unexpected high recovery from the spray-dry process, as compared to the same mRNA-LNP formulations prepared without polymer.

In particular, two of LNP-encapsulated mRNA formulations (mRNA encoding Firefly Luciferase (FFL) and formulations referred to as FFL-F1 an FFL-F2, respectively) each were prepared without polymer or with polymer, with the individual compositions of each described in Table 1. To prepare these formulations for spray-drying, the FFL mRNA was first mixed with lipid nanoparticles (LNPs) using a gear pump in order to encapsulate the mRNA within the LNPs. Then, for the "With Polymer" samples, the polymer solution then was mixed with mRNA-LNPs using a gear pump. The solutions were then subjected to spray-drying as depicted in the graphical representation of the instrumentation in FIG. 1. The following conditions were used for the spray-drying: an inlet temperature of 90° C., an aspirator percentage of 85%, a pump percentage of 25% and an outlet temperature of 46-50° C.

TABLE 1 mRNA formulation compositions and characteristics for Example 1

| Ingredient | Mass (g) FFL-F1 Without Polymer | FFL-F1 With Polymer | FFL-F2 Without Polymer | FFL-F2 With Polymer |
|---|---|---|---|---|
| mRNA | 0.025 | 0.025 | 0.025 | 0.025 |
| Lipid Nanoparticle | | | | |
| DMG-PEG lipid | 0.0428 | 0.0428 | 0.0963 | 0.0963 |
| cKK-E12 cationic lipid | 0.1549 | 0.1549 | 0.3098 | 0.3098 |
| DPPC lipid | 0 | 0 | 0.3149 | 0.3149 |
| Total lipids mass | 0.1977 | 0.1977 | 0.721 | 0.721 |
| Polymers | | | | |
| Eudragit EPO polymer | 0 | 0.187 | 0 | 0.187 |
| Poloxamer 407 polymer | 0 | 0.0625 | 0 | 0.0625 |
| Total polymer mass | 0 | 0.2325 | 0 | 0.2495 |
| Other Components | | | | |
| Citric Acid | 0.089 | 0.089 | 0.089 | 0.089 |
| Sodium Citrate | 0.04756 | 0.04756 | 0.04756 | 0.04756 |
| Mannitol | 1.25 | 1.25 | 1.25 | 1.25 |
| Characteristics | | | | |
| mRNA Content (% w/w) | 1.34 | 1.34 | 1.05 | 1.05 |
| Total Polymer/Total Lipid (mass ratio) | n/a | 1.18 | n/a | 0.35 |
| Total Polymer/PEG Lipid (mass ratio) | n/a | 5.43 | n/a | 2.59 |
| mRNA encapsulation (%) before spray-drying | 82.99 ± 0.55 | 82.99 ± 0.55 | 81.66 ± 0.15 | 81.66 ± 0.15 |
| mRNA encapsulation (%) after spray-drying | not measured | 81.29 ± 0.43 | not measured | 84.77 ± 0.30 |
| % Mass Recovery from spray-drying | 1 ± 2% | 43 ± 3% | 2 ± 2% | 45 ± 4% |
| Z-average size (nm) before spray-drying | 106.17 ± 1.86 | 106.17 ± 1.86 | 95.05 ± 1.66 | 95.05 ± 1.66 |
| Z-average LNP size (nm) after spray-drying | not measured | 1186 ± 313 | not measured | 207.97 ± 1.25 |

Results

Figure 2:
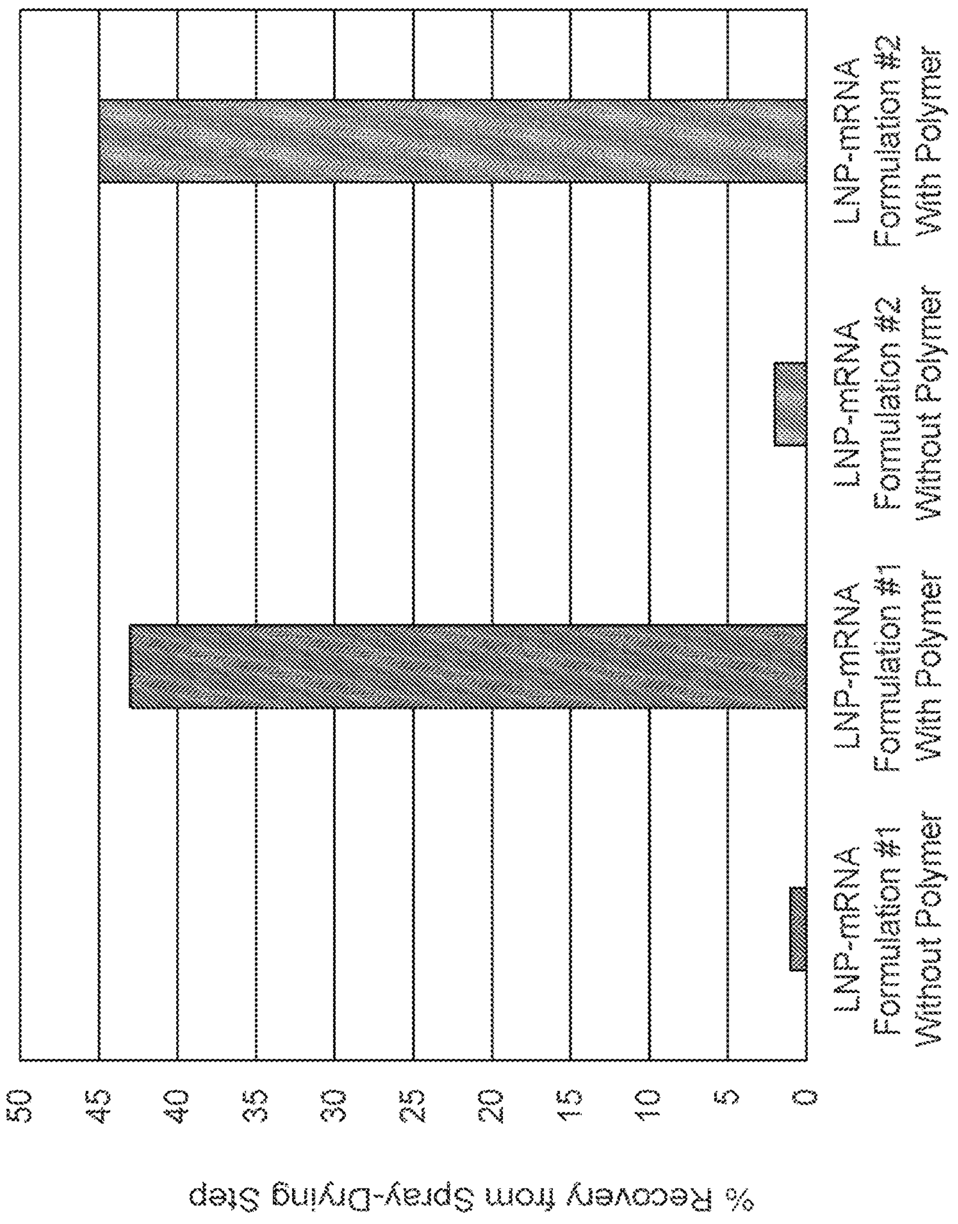
FIG. 2 shows the percent recovery of LNP-encapsulated mRNA material following spray-drying, without and with polymer in the formulation.

The spray-drying step on each LNP-mRNA formulation without polymer was unsuccessful. In each case, the material aggregated in the spray-dryer and clogged various compartments of the spray-dryer, such there was little to no recovery of material, as described in Table 1 (bottom) and as depicted in FIG. 2. However, the same two LNP-mRNA formulations prepared with polymer each was successfully spray-dried and yielded greater than 40% recovery of material from the spray-drying step, as described in Table 1 (bottom) and as depicted in FIG. 2.

The effect of spray-drying on encapsulation efficiency and nanoparticle size (Z-average) were measured before and after the spray-drying step, with values provided in Table 1 (bottom). For the LNP-mRNA formulations prepared with polymer, encapsulation efficiency did not change appreciable in material before and after spray-drying and nanoparticle size was found to increase from before to after spray-drying. For the LNP-mRNA formulations prepared without polymer, these measures could not be determined due to the failure of the spray-drying step to produce any substantial material.

Example 2. Integrity and Stability of mRNA Dry Powder Formulations

In this example, two mRNA formulations encoding argininosuccinate synthetase or ASS1 mRNA were prepared and assessed for long-term stability. In particular, one mRNA formulation was prepared that included no LNP but did include polymer (ASS1-F1). A second mRNA formulation was prepared that included LNP-encapsulated LNP plus polymer (ASS-F2). Each formulation is described further in Table 2.

For the ASS1-F1 formulation, the mRNA was directly mixed with the polymer using a gear pump. For the ASS1-F2 formulation, the mRNA was first mixed with lipid nanoparticles (LNPs) using a gear pump in order to encapsulate the mRNA within the LNPs and then the polymer solution was mixed with the mRNA-LNPs using a gear pump. The final formulations were concentrated, and mannitol was added to each formulation. The solutions were then subjected to spray-drying as depicted in the graphical representation of the instrumentation in FIG. 1. The following conditions were used for the spray-drying: an inlet temperature of 90° C., an aspirator percentage of 85%, a pump percentage of 25% and an outlet temperature of 46-50° C.

TABLE 2 mRNA formulation compositions and characteristics for Example 2

| Components | Mass (g) ASS1-F1 | ASS1-F2 |
|---|---|---|
| mRNA | 0.05 | 0.05 |
| Lipids | | |
| DMG-PEG lipid | 0 | 0.0856 |
| cKK-E12 cationic lipid | 0 | 0.3098 |
| Total lipid mass | 0 | 0.3954 |
| Polymers | | |
| Eudragit EPO polymer | 0.374 | 0.374 |
| Poloxamer 407 polymer | 0.050 | 0.125 |
| Total polymer mass | 0.424 | 0.499 |
| Other Components | | |
| Citric Acid | 0.0712 | Disregarded |
| Sodium Citrate | 0.09805 | Disregarded |
| Mannitol | 2.5 | 2.5 |
| Characteristics | | |
| mRNA Content (% w/w) | 1.62 | 1.45 |
| Total Polymer/Total Lipid (mass ratio) | n/a | 1.26 |
| Total Polymer/PEG Lipid (mass ratio) | n/a | 5.83 |
| mRNA encapsulation (%) before spray-drying | n/a | 75.28 ± 1.43 |
| mRNA encapsulation (%) after spray-drying | n/a | 81.85 ± 0.44 |
| Z-average size (nm) before spray-drying | n/a | 99.4 ± 1.3 |
| Z-average LNP size (nm) after spray-drying | n/a | 426 ± 12 |

Encapsulation efficiency and nanoparticle size. The effect of spray-drying on encapsulation efficiency was measured before and after the drying. In this example, encapsulation efficiency of the LNP-encapsulated mRNA in a formulation with polymer was 75.28±1.43 before the process and 81.85±0.44 after, indicating that the spray-drying process did not negatively impact encapsulation efficiency. The average sizes of the nanoparticles before and after spray drying were 99.4±1.3 and 426±12, respectively.

Integrity and stability of mRNA dry powder. The LNP-encapsulated mRNA in a formulation with polymer provided an unexpected high integrity and stability of the mRNA following spray-drying, even when stored at refrigeration temperature (4° C.) or frozen at −20° C. for various time periods. mRNA integrity and stability described below was assessed by spectrophotometric analysis, e.g., capillary electrophoresis (CE), as well as by gel electrophoresis, e.g., by northern blot analysis.

Figure 3:
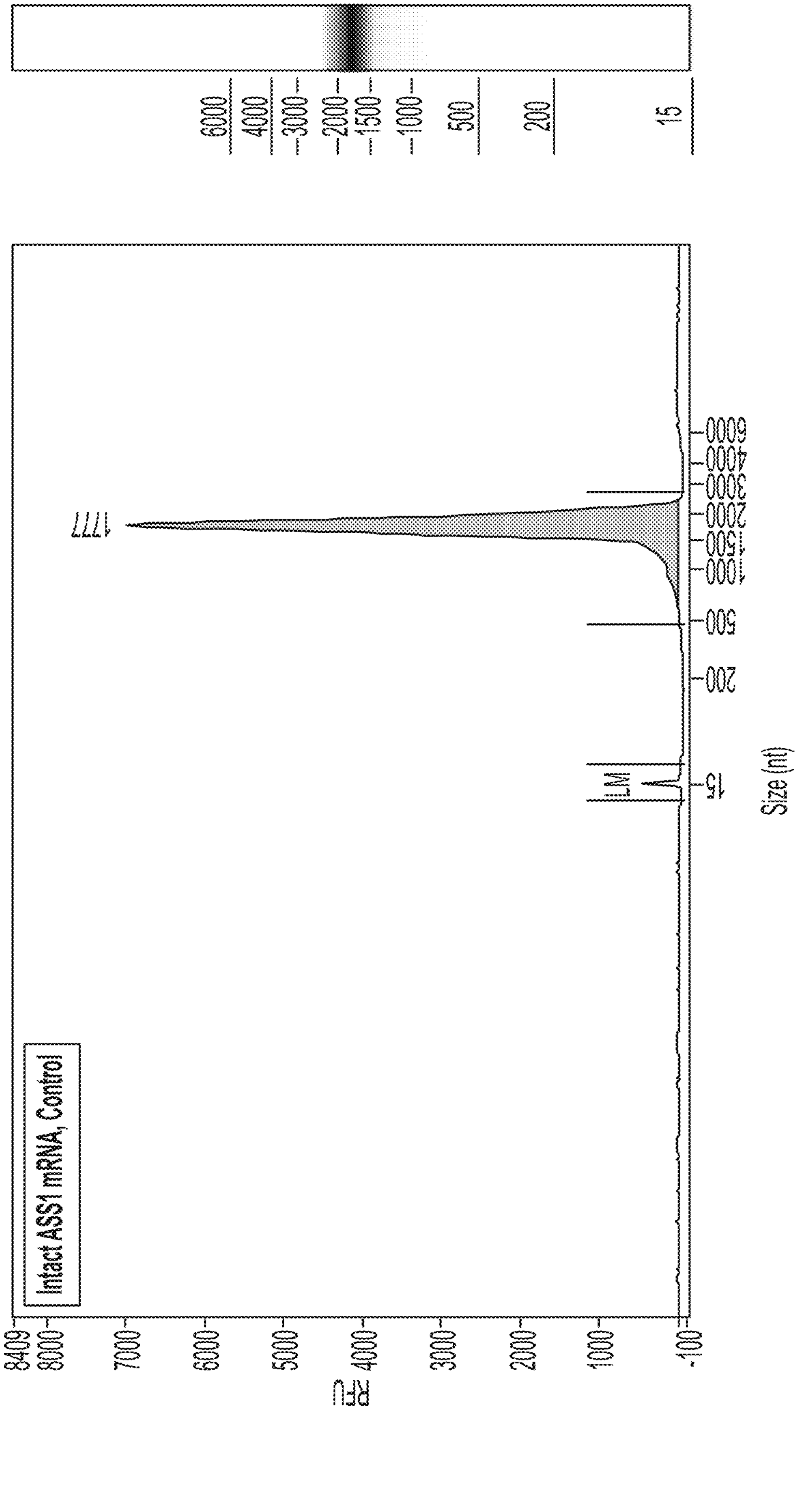
FIG. 3 depicts spectrophotometric analysis of an mRNA reference for integrity assessment.
Figure 4:
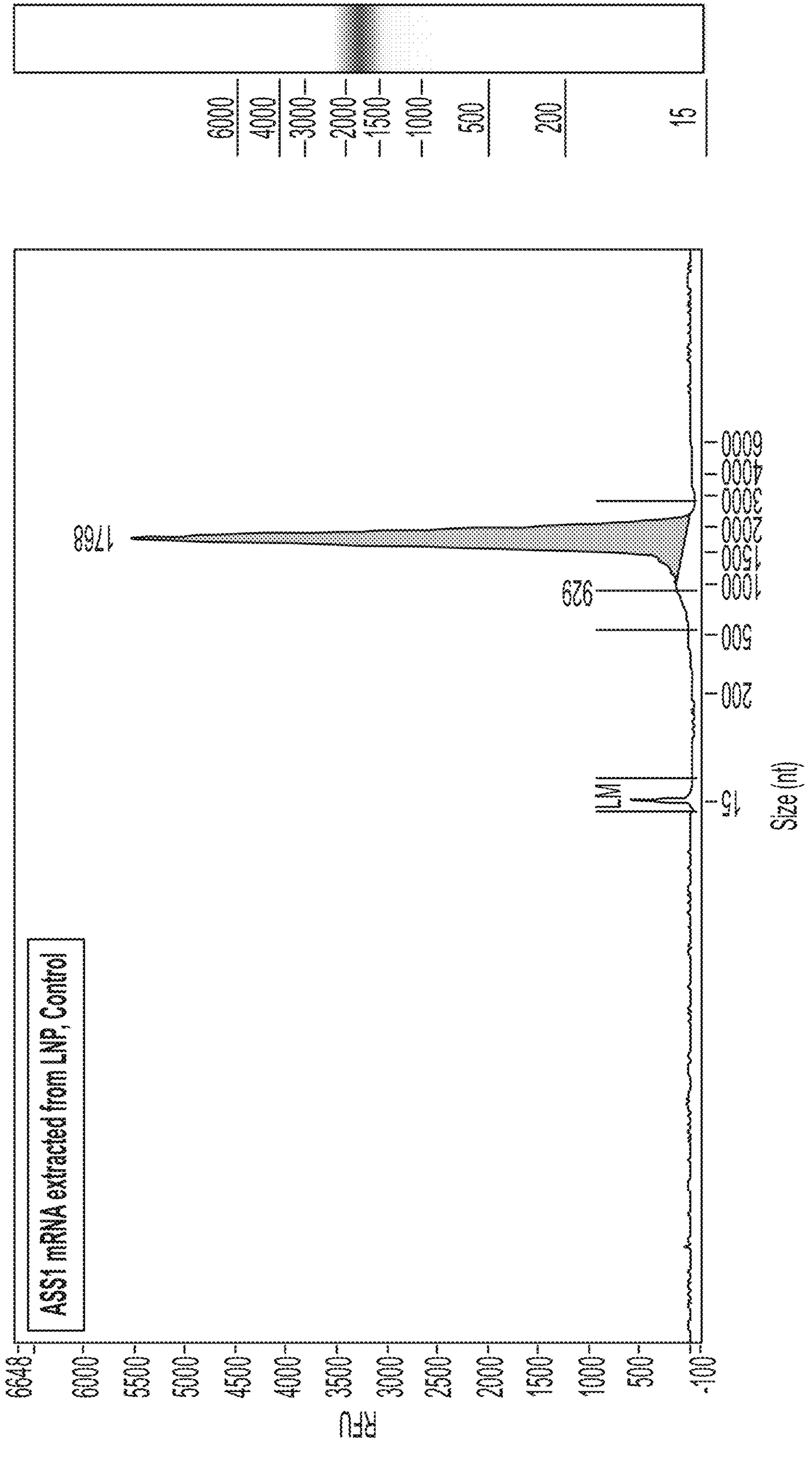
FIG. 4 depicts exemplary data illustrating integrity of mRNA upon extraction from a lipid nanoparticle.

FIG. 3 and FIG. 4 serve as exemplary controls for the analysis of mRNA integrity. In particular, FIG. 3 shows intact mRNA as assessed by CE (left-hand panel) and by gel electrophoresis (right-hand panel). In the left-hand panel of the figure, the intact mRNA appears as a single spectrophotometric peak (shaded) and, in the right-hand panel of the figure, the intact mRNA appears as a single band corresponding to the expected molecular size of the mRNA, which single peak and single band each indicate intact mRNA and absence of degradation products. Similarly, FIG. 4 shows mRNA prior to spray drying and extracted from the LNP (i.e., extracted for the purpose of the conducting the CE and gel electrophoresis analyses on the mRNA), to confirm that extraction of the mRNA from the LNP does not produce significant mRNA degradation products. Comparison of the CE peak and gel band in FIG. 4 to those in FIG. 3 shows that the process used to extract mRNA from the LNPs does not produce significant mRNA degradation products.

Aliquots of the spray-dried ASS1-F1 formulation or the spray-dried ASS1-F2 formulation were stored at either at 4° C. or at −20° C., and at various time points samples were removed, reconstituted and assessed for mRNA integrity by CE and gel electrophoresis. In particular, the mRNA integrity of dry powder ASS1 mRNA-LNP formulated with polymer (ASS1-F2) was assessed at weeks 2 and 4 after spray-drying and storage at either at 4° C. or at −20° C.; and mRNA integrity of dry powder ASS1 mRNA (without LNP) formulated with polymer (ASS1-F1) was assessed at weeks 3 and 5 after spray-drying and storage at either at 4° C. or at −20° C.

Figure 5:
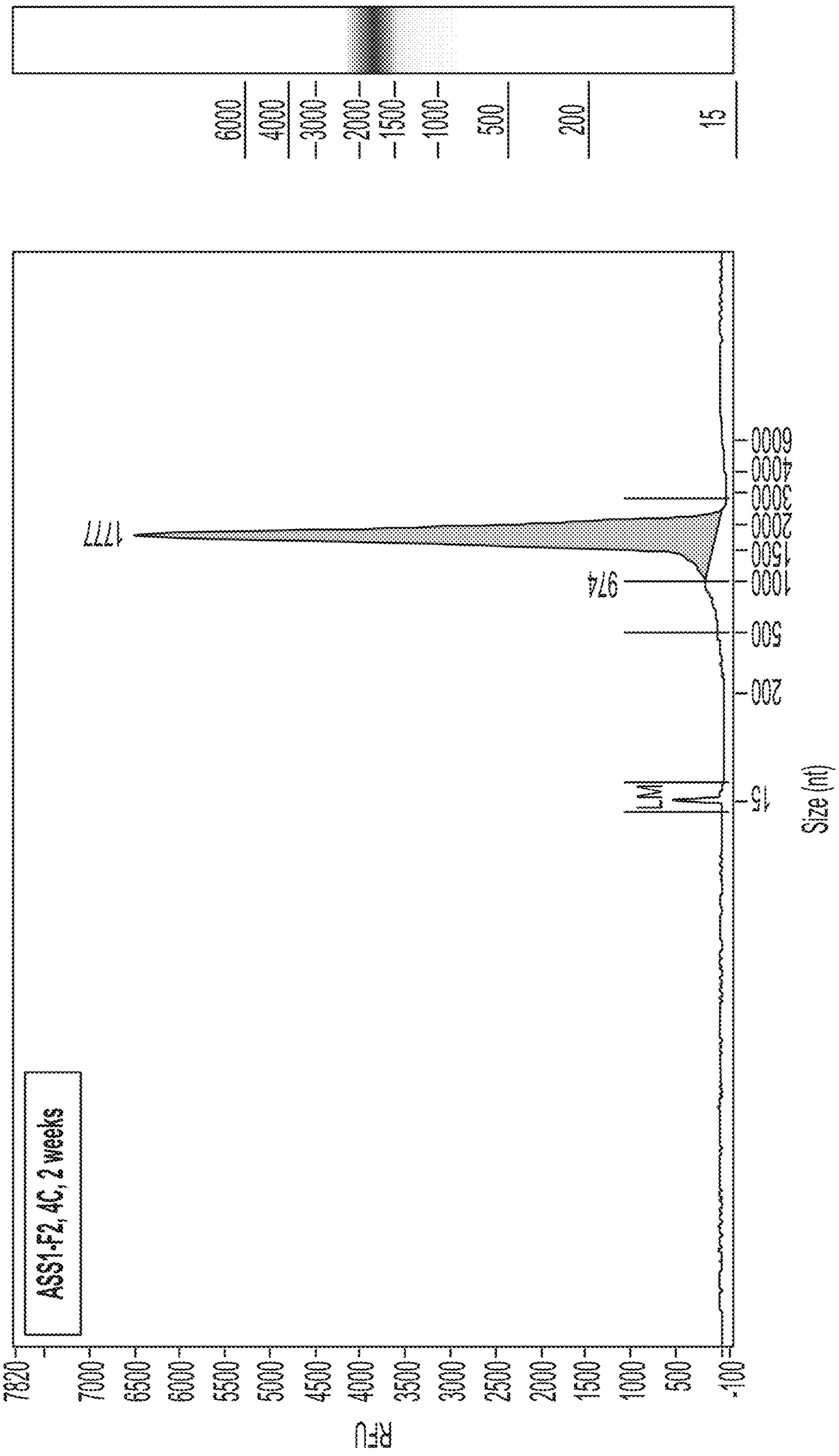
FIG. 5 depicts exemplary data illustrating integrity of mRNA encapsulated in a LNP in a formulation with polymer at two weeks following spray-drying and storage at 4° C.
Figure 6:
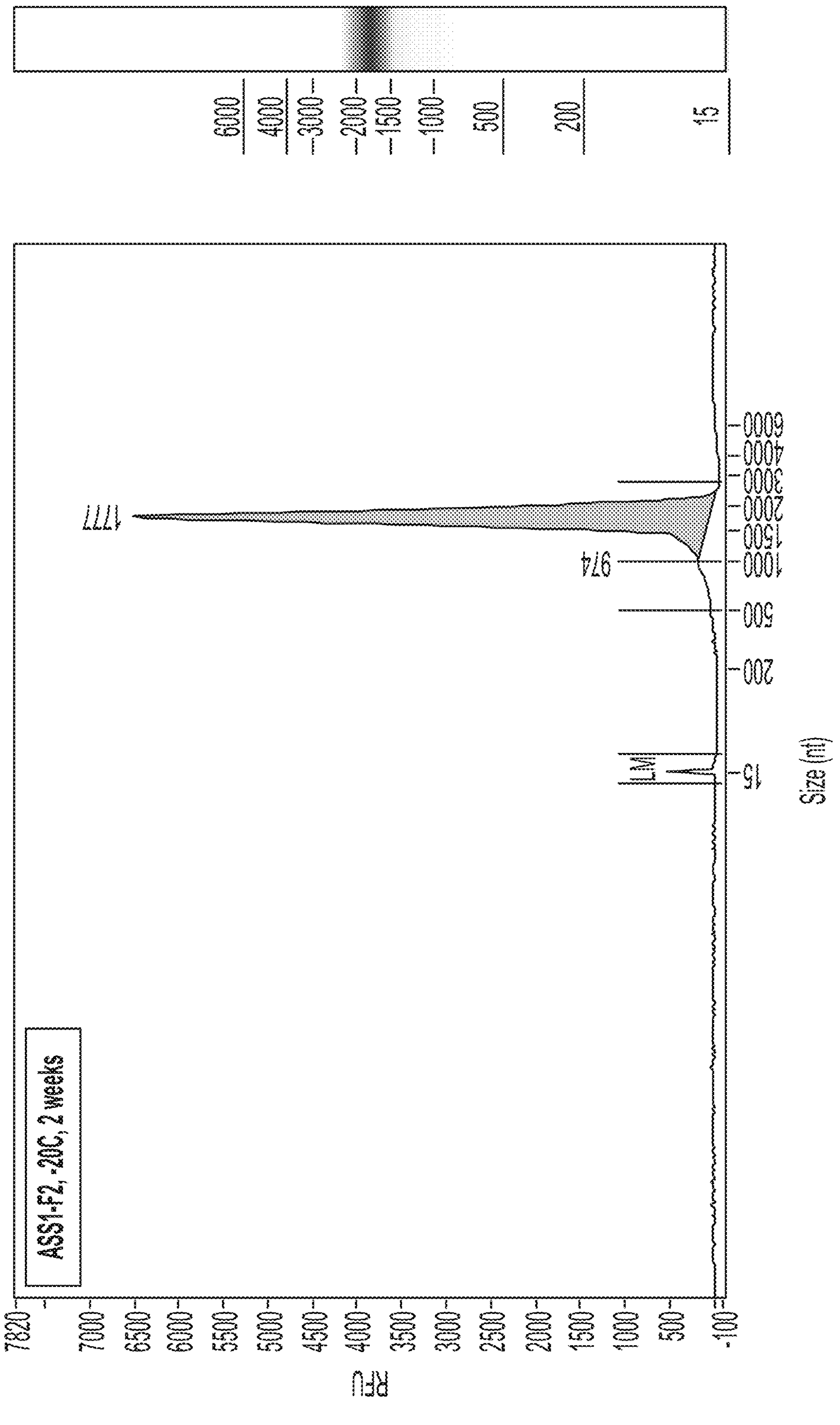
FIG. 6 depicts exemplary data illustrating integrity of mRNA encapsulated in a LNP in a formulation with polymer at two weeks following spray-drying and storage at −20° C.
Figure 7:
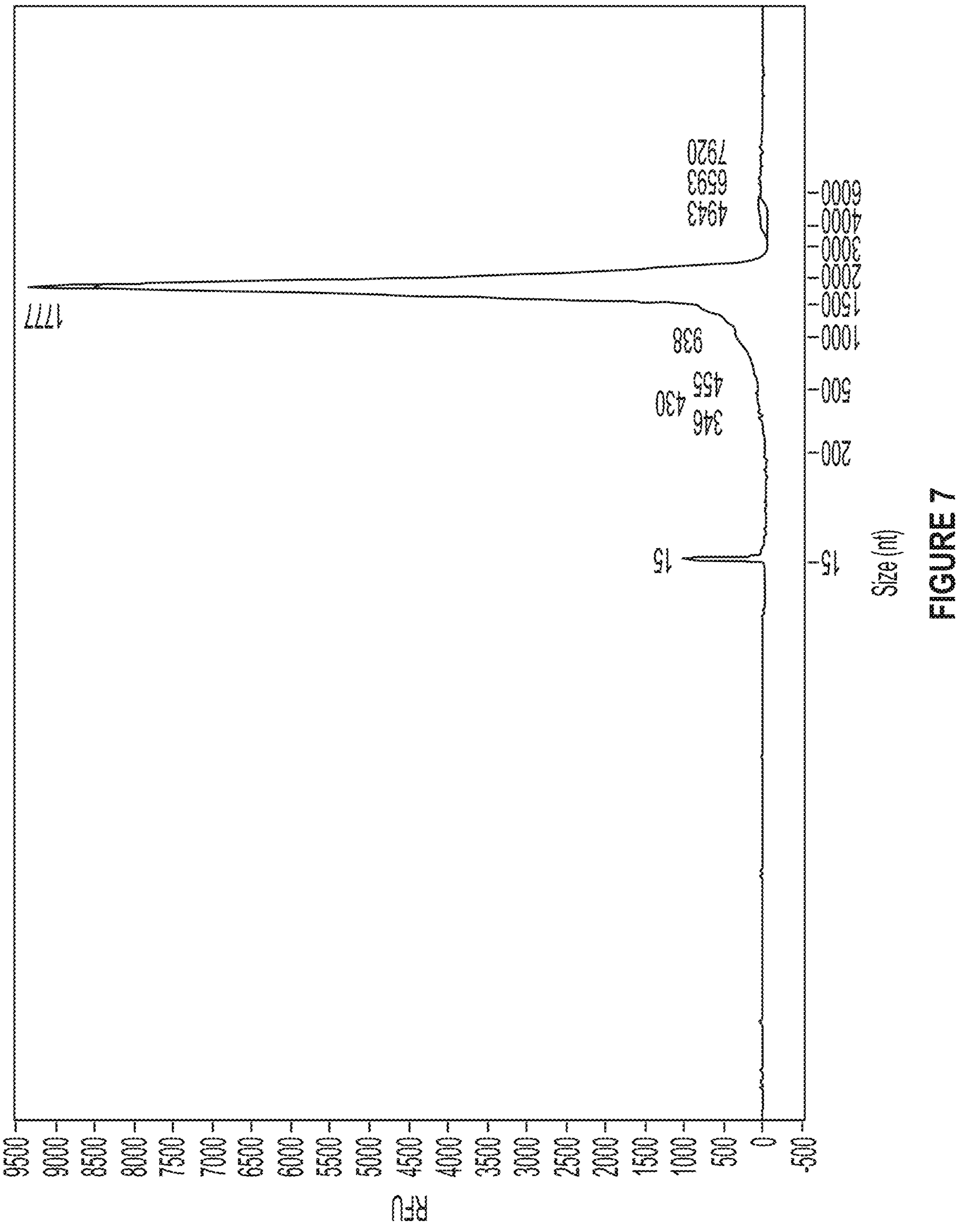
FIG. 7 depicts exemplary data that shows no effect of storage temperature on integrity of mRNA encapsulated in a LNP in a formulation with polymer and stored for two weeks after spray-drying.

FIG. 5 and FIG. 6 show mRNA integrity of dry powder ASS1 mRNA-LNP formulated with polymer (ASS1-F2) and stored for two weeks at 4° C. or at −20° C., respectively. Each of FIG. 5 and FIG. 6 show a single CE peak (left-hand panel) and a single gel band (right-hand panel) indicating that the ASS1 mRNA remains intact, without degradation, at both temperature conditions. FIG. 7 further shows superimposition of the two peaks of ASS1 mRNA (from FIG. 5 and FIG. 6), indicating that the mRNA remained intact irrespective of the storage temperature. These data indicate that spray-dried formulations of mRNA lipid nanoparticles with a polymer remain stable for at least two weeks over a range of storage temperatures, for example, at or up to about −20° C. or at or up to about 4° C.

Figure 8:
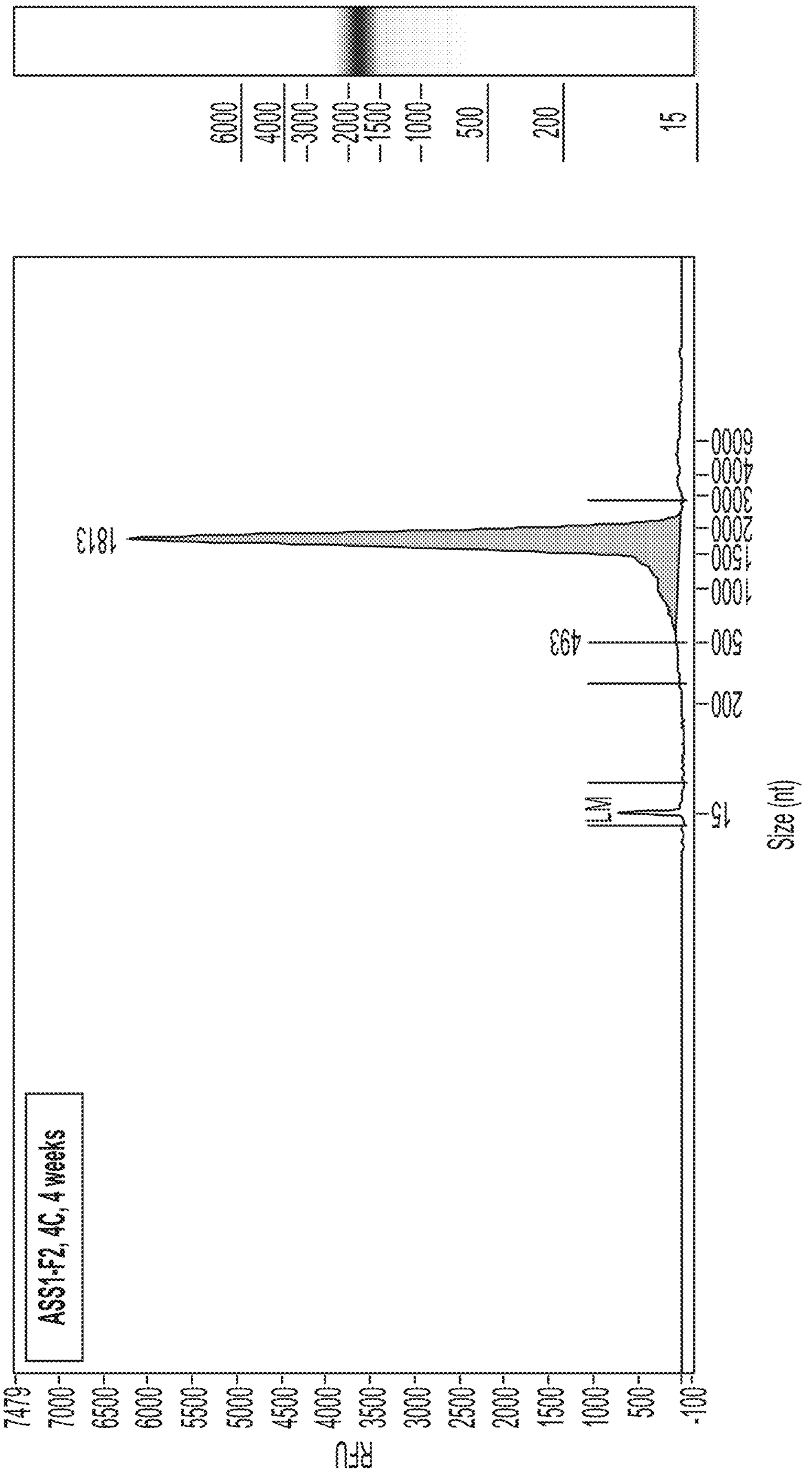
FIG. 8 depicts exemplary data illustrating integrity of mRNA encapsulated in a LNP in a formulation with polymer at four weeks following spray-drying and storage at 4° C.
Figure 9:
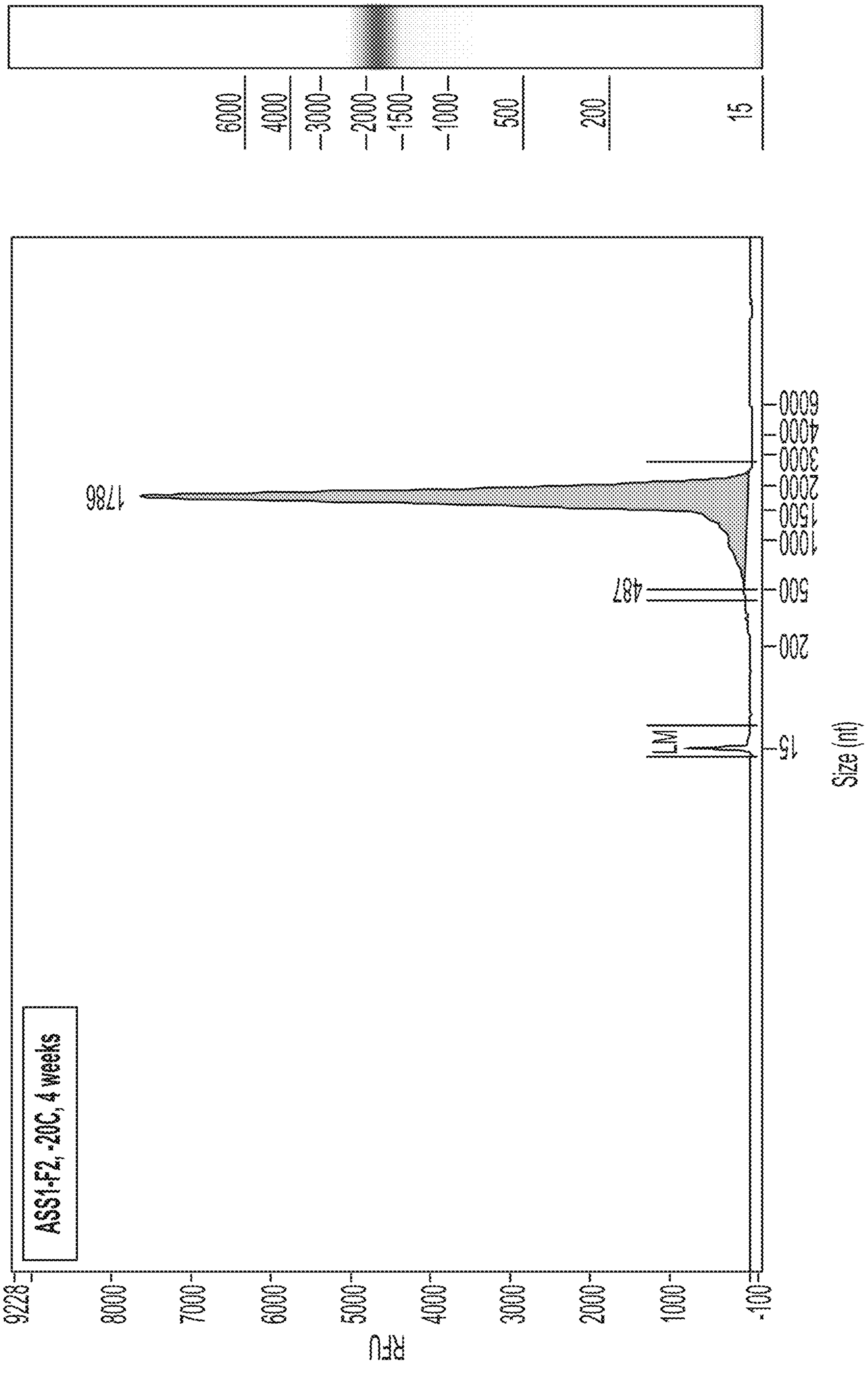
FIG. 9 depicts exemplary data illustrating integrity of mRNA encapsulated in a LNP in a formulation with polymer at four weeks following spray-drying and storage at −20° C.

FIG. 8 and FIG. 9 show mRNA integrity of dry powder ASS1 mRNA-LNP formulated with polymer (ASS1-F2) and stored for four weeks at 4° C. or at −20° C., respectively. Both FIG. 8 and FIG. 9 show a single CE peak (left-hand panel) and a single gel band (right-hand panel) indicating that the ASS1 mRNA remains intact, without degradation, at both temperature conditions. These data indicate that spray-dried formulations of mRNA lipid nanoparticles with a polymer remain stable for at least four weeks over a wide range of storage temperatures, for example, at or up to about −20° C. or at or up to about 4° C.

Figure 10:
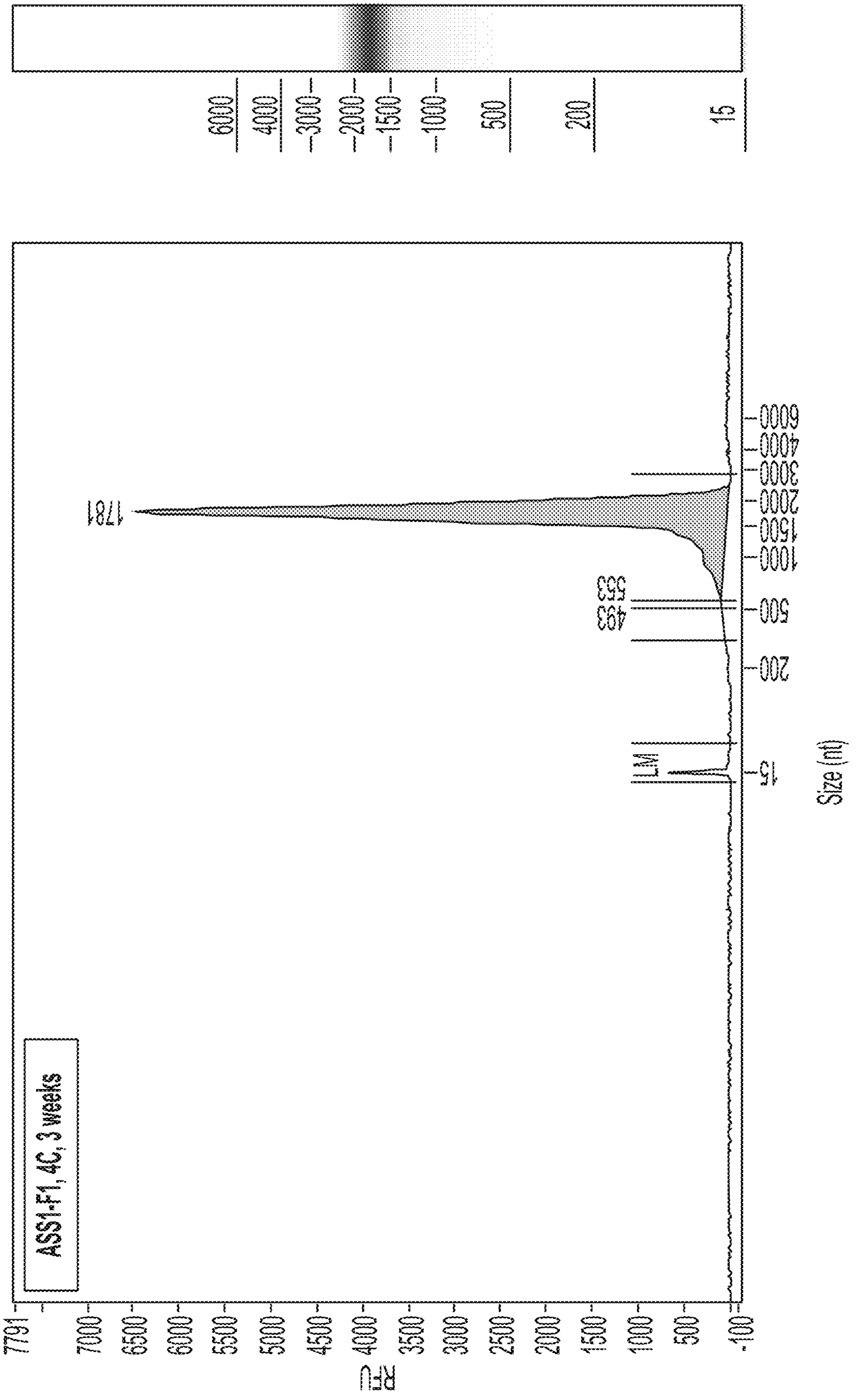
FIG. 10 depicts exemplary data illustrating integrity of mRNA in a formulation with polymer (without LNP) at three weeks after spray-drying, stored at 4° C.
Figure 11:
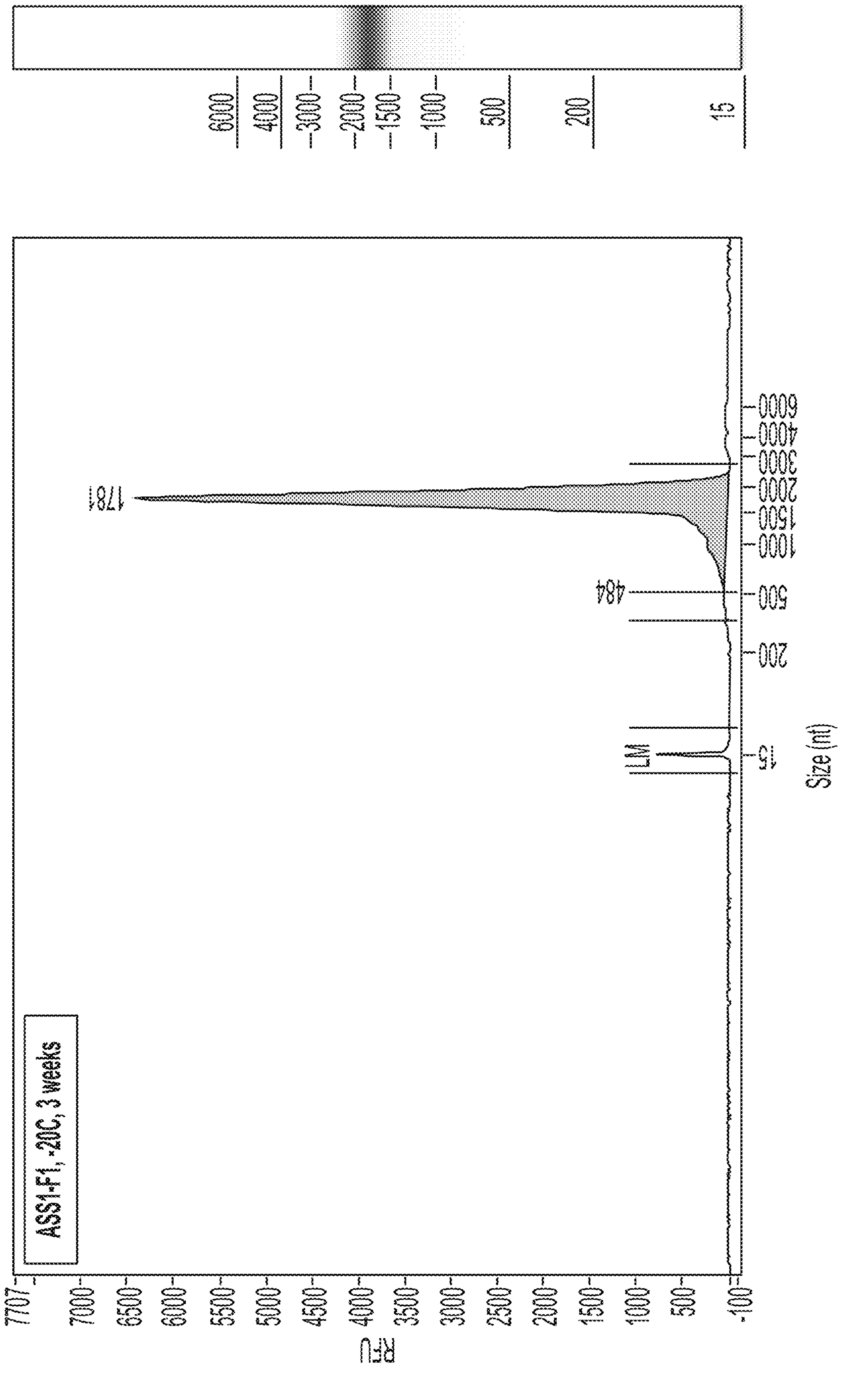
FIG. 11 depicts exemplary data illustrating integrity of mRNA in a formulation with polymer (without LNP) at three weeks after spray-drying, stored at −20° C.
Figure 12:
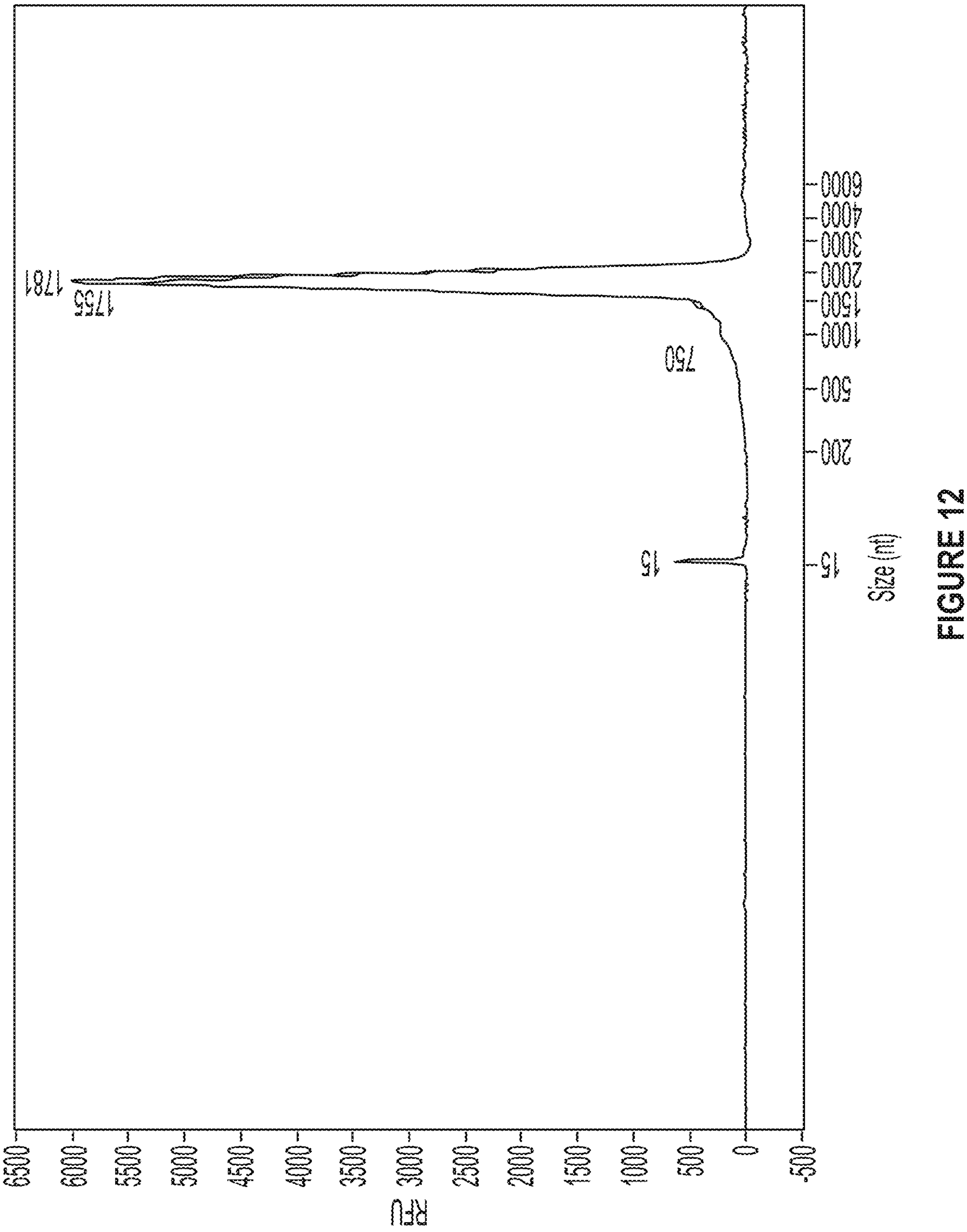
FIG. 12 depicts exemplary data that shows no effect of storage temperature on integrity of mRNA formulated with polymer (without LNP) and stored for three weeks after spray-drying.

FIG. 10 and FIG. 11 show mRNA integrity of dry powder ASS1 mRNA (without LNP) formulated with polymer (ASS1-F1) and stored for three weeks at 4° C. or at −20° C., respectively. As shown in FIG. 10 and FIG. 11, the ASS1-F1 mRNA remained intact, without degradation, at both temperature conditions. FIG. 12 depicts superimposition of the CE peaks of ASS1 mRNA (from FIG. 10 and FIG. 11), in which the complete alignment of the CE peaks indicates absence of degradation of the mRNA. This shows that spray-dried formulations of mRNA with a polymer (without LNP encapsulation) remain stable for at least three weeks over a wide range of storage temperatures, for example, at or up to about −20° C. or at or up to about 4° C.

Figure 13:
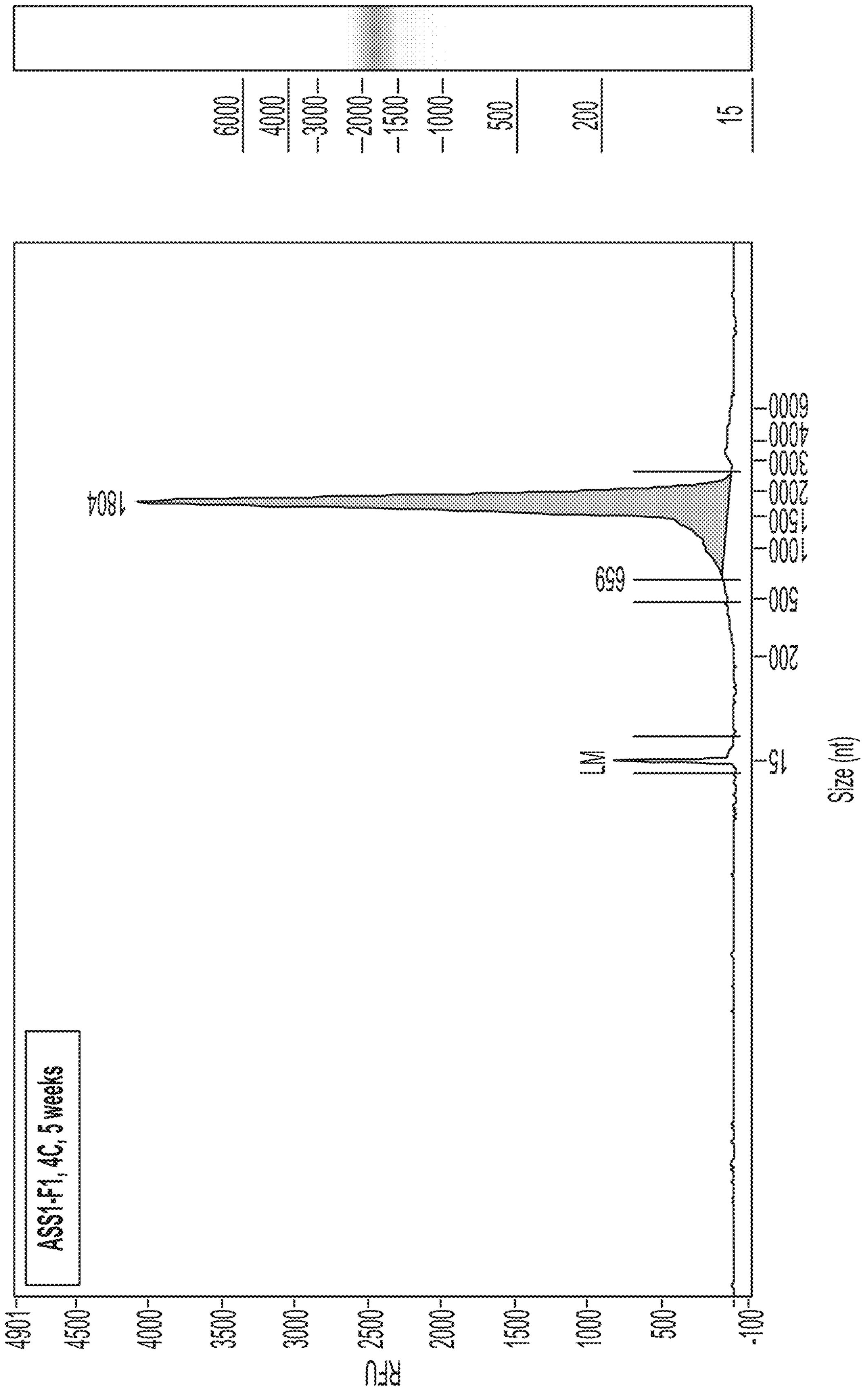
FIG. 13 depicts exemplary data illustrating integrity of mRNA in a formulation with polymer (without LNP) at five weeks after spray-drying, stored at 4° C.
Figure 14:
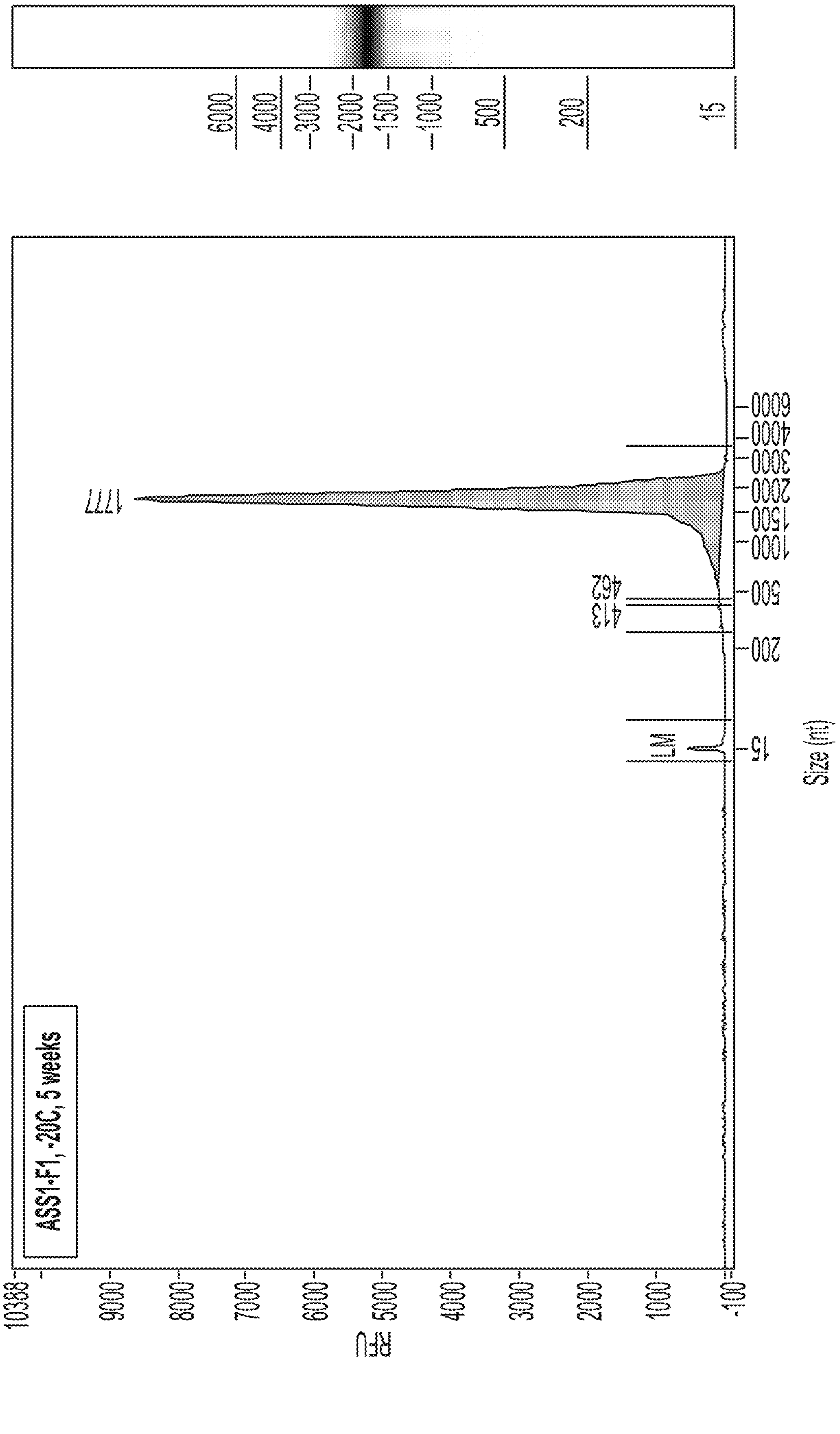
FIG. 14 depicts exemplary data illustrating integrity of mRNA in a formulation with polymer (without LNP) at five weeks after spray-drying, stored at −20° C.

FIG. 13 and FIG. 14 show mRNA integrity of dry powder ASS1 mRNA (without LNP) formulated with polymer (ASS1-F1) and stored for five weeks at 4° C. or at −20° C., respectively. As shown in FIG. 13 and FIG. 14, the ASS1-F1 mRNA remained intact without degradation at both temperature conditions. This shows that spray-dried formulations of mRNA with a polymer (without LNP encapsulation) remain stable for at least five weeks over a wide range of storage temperatures, for example, at or up to about −20° C. or at or up to about 4° C.

Surprisingly, for both dry powder ASS1 mRNA-LNP formulated with polymer (ASS1-F2) and for dry powder ASS1 mRNA (without LNP) formulated with polymer (ASS1-F1), the integrity of mRNA was maintained for extended time periods at elevated storage temperatures, e.g., refrigerated storage (about 4° C.).

Example 3. One-Step Method of mRNA Encapsulation in Lipid-Polymer Nanoparticle In this example, lipids, mRNA and polymer were prepared in a single step to produce lipid-polymer-encapsulated mRNA nanoparticles (formulations ASS1-F3 With Polymer and ASS1-F4 With Polymer). This is in contrast to Example 1 and Example 2 where LNP-encapsulating mRNA nanoparticles were first prepared and then polymer was added into the formulation. In addition, reference formulations were prepared by the same process but without including polymer in the nanoparticle or formulation (formulations ASS1-F3 Without Polymer and ASS1-F4 Without Polymer).

In particular, lipids and polymer (or just lipids for the control formulations) were dissolved in ethanol and together mixed with mRNA solution using a gear pump. Four different formulations were prepared. The first and second formulations (ASS1-F3 Without Polymer and ASS1-F3 With Polymer) were prepared with cKK-E12 as the cationic lipid, either without or with polymer. The third and fourth formulations (ASS1-F4 Without Polymer and ASS1-F4 With Polymer) were prepared with ICE (imidazole cholesterol ester) as the cationic lipid, either without or with polymer. ASS1-F3 With Polymer and ASS1-F4 With Polymer included Eudragit as the polymer. All four formulations included mRNA encoding ASS1 as the nanoparticle-encapsulated mRNA. Each formulation was concentrated, and mannitol was added. All formulations are described further in Table 3. Each formulation was subjected to spray drying using the conditions described in Example 1.

TABLE 3 mRNA formulation compositions and characteristics for Example 3

| | Mass (g) | | | |
|---|---|---|---|---|
| Ingredient | ASS1-F3 Without Polymer | ASS1-F3 With Polymer | ASS1-F4 Without Polymer | ASS1-F4 With Polymer |
| mRNA | 0.05 | 0.05 | 0.05 | 0.05 |
| Lipids | | | | |
| DMG-PEG lipid | 0.0856 | 0.0856 | 0.0856 | 0.0856 |
| ckk-E12 lipid | 0.3098 | 0.3098 | 0 | 0 |
| ICE lipid | 0 | 0 | 0.1587 | 0.1587 |
| Total lipid mass | 0.3954 | 0.3954 | 0.2443 | 0.2443 |
| Polymers | | | | |
| Eudragit EPO polymer | 0 | 0.374 | 0 | 0.374 |
| Total polymer mass | 0 | 0.374 | 0 | 0.374 |
| Other Components | | | | |
| Mannitol | 2.5 | 2.5 | 2.5 | 2.5 |
| Characteristics | | | | |
| mRNA Content (% w/w) | 1.51 | 1.51 | 1.58 | 1.58 |
| Total Polymer/Total Lipid (mass ratio) | n/a | 0.95 | n/a | 1.53 |
| Total Polymer/PEG Lipid (mass ratio) | n/a | 4.37 | n/a | 4.37 |
| mRNA encapsulation (%) before spray-drying | not measured | 79.24 ± 0.14 | not measured | 76.25 ± 0.60 |
| Z-average LNP size (nm) before spray-drying | not measured | 141.8 ± 1.6 | not measured | 106.6 ± 2.0 |
| % Mass Recovery from spray-drying | 1 ± 2% | 39 ± 5% | 1 ± 2% | 38 ± 3% |
| mRNA encapsulation (%) after spray-drying | not measured | 79.49 ± 0.37 | not measured | 80.49 ± 0.61 |
| Z-average LNP size (nm) after spray-drying | not measured | 471.7 ± 59 | not measured | 308.0 ± 7.2 |

Results

The spray-drying step for the formulations without polymer (ASS 1-F3 Without Polymer and ASS-F4 Without Polymer) was unsuccessful. In each case, the material aggregated in the spray-dryer and clogged various compartments of the spray-dryer, such there was little to no recovery of material, as described in Table 3 (bottom) showing a recovery of 1±2% for each formulation without polymer. However, those same two formulations prepared with polymer in the nanoparticle (ASS1-F3 With Polymer and ASS-F4 With Polymer) each were successfully spray-dried and yielded greater than 35% and nearly 40% recovery of material from the spray-drying step, as described in Table 3.

The effects of spray-drying on encapsulation efficiency and nanoparticle size (Z-average) for formulations prepared with polymer in the nanoparticle were measured before and after the spray-drying step, with values provided in Table 3 (bottom). For each lipid-polymer-mRNA nanoparticle, encapsulation efficiency did not change appreciable before and after spray-drying and nanoparticle size was found to increase from before to after spray-drying. For the formulations prepared without polymer, these measures could not be determined due to the failure of the spray-drying step to produce any substantial material.

These results show, among other things, that polymer added into a lipid nanoparticle that encapsulates mRNA allows for successful spray-drying of the mRNA-encapsulated lipid nanoparticle. This is in contrast to the same lipid nanoparticle that does not include mRNA, which was not successfully spray-dried.

Example 4. One-Step Method of mRNA Encapsulation in Lipid-Polymer Nanoparticle In this example, the polymer, PLGA, was mixed with lipids and mRNA in a single step to produce lipid-PLGA-encapsulated mRNA nanoparticles.

In particular, lipids and PLGA (or just lipids for the control formulations) were dissolved in an ethanol and acetonitrile (1:2) mixture and mixed with ASS1 mRNA solution using a gear pump. The final formulation was concentrated in 5% mannitol, and then spray dried. The following conditions were used for the spray-drying: an inlet temperature of 90° C., an aspirator percentage of 85%, a pump percentage of 25% and an outlet temperature of 46-50° C. The formulations are described further in Table 4.

TABLE 4 mRNA formulation compositions and characteristics for Example 4

| Ingredient | Mass (g) |
|---|---|
| mRNA | 0.05 |
| Lipids | |
| DMG-PEG lipid | 0.1283 |
| ICE lipid | 0.3175 |
| DOPE lipid | 0.27 |
| Polymers | |
| PLGA | 0.215 |
| Other Components | |
| Mannitol | 2.5 |
| Characteristics | |
| mRNA Content (% w/w) | 1.44 |

Results

The spray-drying step for the formulation prepared with PLGA polymer in the nanoparticle was successfully spray-dried and yielded recovery of material from the spray-drying step.

Example 5. In Vivo Delivery of Spray-Dried mRNA Formulations

In this example, the spray dried formulation, FFL-F1 With Polymer (as described in Example 1) was administered to mice both as a dry powder and dissolved in liquid, and expression of the mRNA in the administered formulations was detected in both approaches.

Figure 15B:
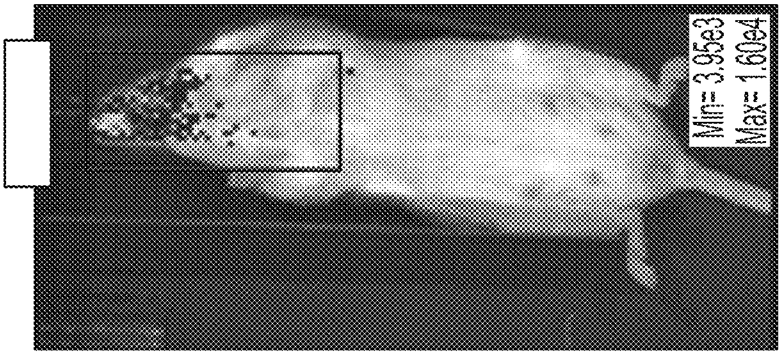
FIG. 15A and FIG. 15B shows exemplary mRNA expression in vivo measured by bioluminescence after administering mRNA spray-dry preparations in mice. Luciferase mRNA was administered using 1 mg. For FIG. 15A, mRNA was administered as a dry-powder. For FIG. 15B, mRNA was administered as liquid following dissolution of the dry powder in water.
Figure 15A:
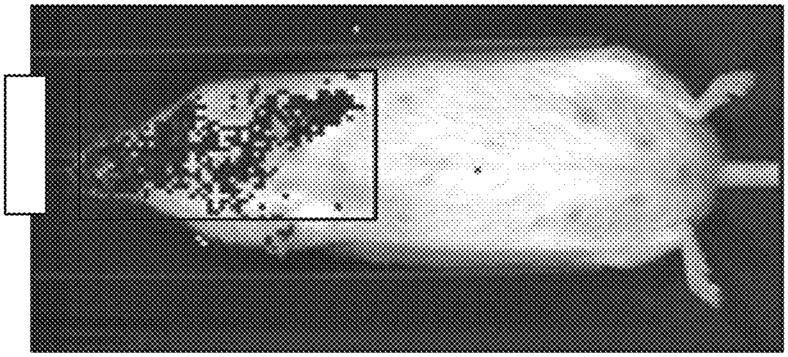

In particular, in one approach the dry powder formulation of FFL-F1 With Polymer was administered to mice at a dose of 1 mg, using a Dry Powder Insufflator, Model DP-4M. At 24 hours following dry powder administration, the FFL substrate, luciferin, was administered with a microsprayer and luciferase expression in vivo was detected by bioluminescence assay. The results are depicted in FIG. 15A.

In a second approach, FFL-F1 With Polymer was dissolved in water at a concentration of 20 mg/ml, and 50 microliters per mouse was administered by microsprayer, for a dose of 1 mg. At 24 hours following administration, the FFL substrate, luciferin, was administered with a microsprayer and luciferase expression in vivo was detected by bioluminescence assay. The results are depicted in FIG. 15B.

These results demonstrate that mRNA encapsulated within an LNP in a formulation with polymer remains active following spray-drying. These results also show that spray-dried LNP-encapsulated mRNA can be administered directly as dry powder to provide expression of protein in vivo.

Example 6. CFTR mRNA Lipid-Polymer Nanoparticle Dry Powder Formulation

In this example, mRNA encoding cystic fibrosis conductance regulator protein (CFTR), or CFTR mRNA, was encapsulated within a lipid-polymer nanoparticle and successfully spray-dried into a stable dry powder.

In particular, to prepare the lipid-polymer nanoparticles encapsulating CFTR-mRNA within them, a PEG-modified lipid, a cationic lipid, and a polymer as described in Table 5 below were dissolved in 150 mL ethanol and mixed with CFTR-mRNA (0.05 g in 600 mL, pH 4.5, 1 mM citrate buffer, 150 mM sodium chloride) using gear pumps. Then, 37.5 g of mannitol was dissolved at 5% weight/volume into that resultant 750 mL solution (20% ethanol) of CFTR-mRNA encapsulated within lipid-polymer nanoparticles. The resulting mixture then was spray dried on Buchi spray dryer using the following spray-drying conditions: an inlet temperature of 90° C., an aspirator percentage of 90%, a pump percentage of 25% and an outlet temperature of 46-50° C.

TABLE 5

CFTR-mRNA lipid-polymer nanoparticle dry-powder formulation

| Ingredient | Mass (g) |
|---|---|
| CFTR mRNA | 0.05 |
| Lipids | |
| DMG-PEG lipid | 0.0856 |
| cKK-E12 lipid | 0.3098 |
| Polymer | |
| Eudragit EPO | 0.215 |
| Other Components | |
| Mannitol | 37.5 |

To quantitatively determine integrity of the CFTR-mRNA in the lipid-polymer nanoparticles following spray-drying, the CFTR-mRNA was precipitated out from the nanoparticles by mixing and dissolving the nanoparticles in ethanol with RNA precipitation buffer comprising guanidine thiocyanate, N-lauroylsarcosine, and sodium citrate, pH 6.5. The precipitated mRNA was further separated and purified using a RNeasy silica membrane (Qiagen) and then redissolved in RNAse free water. The purified mRNA was assessed by capillary electrophoresis using a Fragment Analyzer (Agilent) following manufacturer's published instructions. Briefly, appropriate volumes of intercalating dye and RNA separation gel were mixed and loaded onto the instrument. Capillary conditioning buffer was diluted to required concentration and loaded on the conditioning fluid line. Inlet buffer, rinse buffer, and storage buffers were added to well plates and added to the designated locations. The extracted mRNA and control mRNA were diluted to 150 ng/μL by using formamide loading buffer followed by denaturation by heating at 70° C. for 5 minutes and cooling immediately. The samples were diluted further using diluent marker according to manufacturer's instructions and run on the fragment analyzer by the relevant separation method.

As described in the Examples above, LNP-mRNA formulations without additional polymer in the formulation could not be spray-dried successfully. In particular, the LNP-mRNA material aggregated in the spray-dryer and clogged various compartments of the spray-dryer, such there was little to no recovery of LNP-mRNA material. As the Examples above show, this failure to successfully spray-dry LNP-mRNA material can be overcome with the addition of polymer into the LNP formulation, either by including the polymer with the lipids so that the polymer is present during the step of creating the nanoparticle and encapsulating the mRNA, or alternatively by adding polymer to the formulation following the step of creating the lipid nanoparticle and encapsulating the mRNA.

Figures 1, 16A:
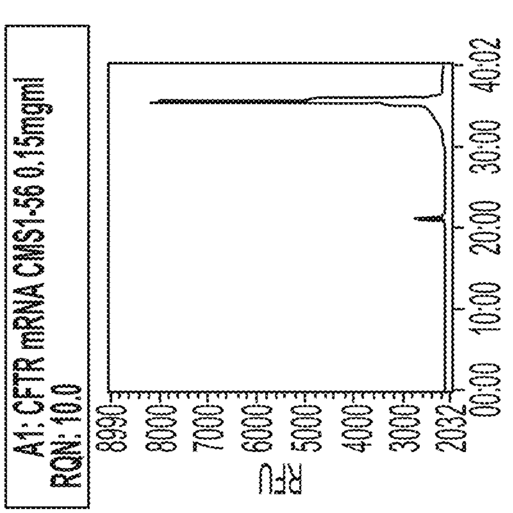
Figures 2, 16A:
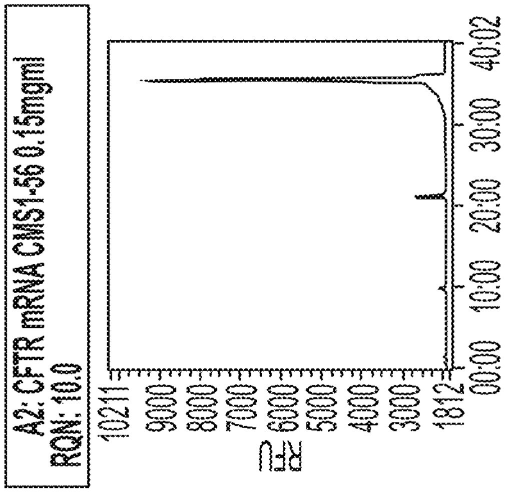
Figures 3, 16A:
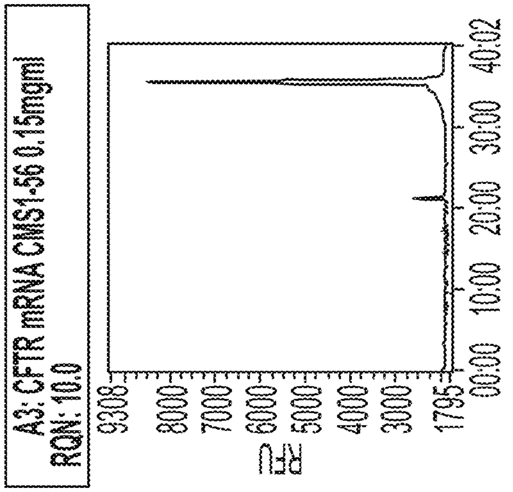
Figures 4, 16A:
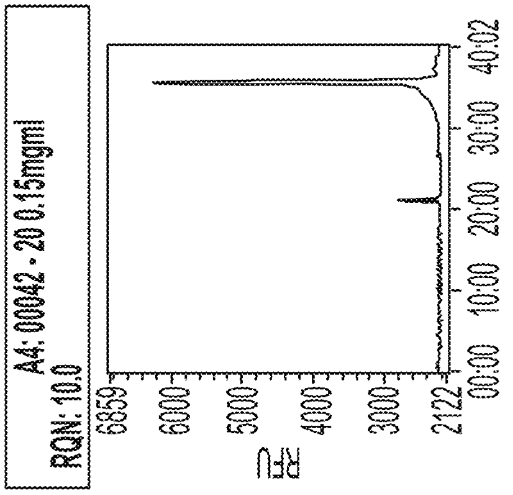
Figures 5, 16A:
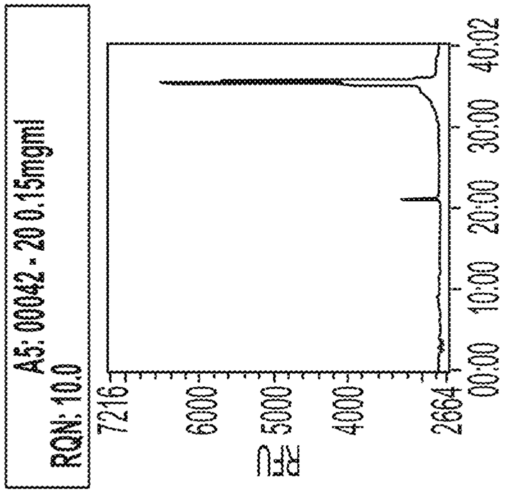
Figures 6, 16A:
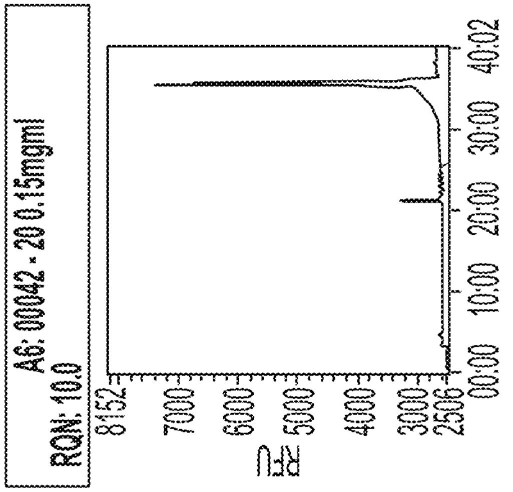

Here, CFTR-mRNA encapsulated within a lipid nanoparticle was successfully spray-dried by addition of a polymer, in particular Eudragit polymer. In particular, the Eudragit polymer was included with the lipid mixture prior to the step of creating the nanoparticle and encapsulating the mRNA, such that a CFTR-mRNA encapsulated with a lipid-polymer nanoparticle was produced. The successfully spray-dried CFTR-mRNA lipid-polymer nanoparticle also was assessed for integrity using capillary electrophoresis (CE) analysis. FIG. 16A1-A6 shows exemplary CE chromatographs of CFTR-mRNA peak integrity before and after spray-drying, indicating that the integrity of the CFTR-mRNA following spray-drying in a lipid-polymer remains intact. FIG. 16A1-A3 depicts control CFTR mRNA which was neither spray dried nor encapsulated, while FIG. 16A4-A6 depicts the CFTR mRNA extracted from the spray-dried formulation.

We claim:

1. A method for manufacturing a dry powder formulation comprising a plurality of spray-dried particles, the method comprising:

spray-drying a mixture comprising one or more messenger RNAs (mRNAs), one or more lipids, and one or more polymers to form the plurality of spray-dried particles, wherein:

the one or more polymers comprise a polymethacrylate based polymer;

a moisture content of the plurality of spray-dried particles is less than 10%;

the plurality of spray-dried particles comprises mRNA-loaded nanoparticles; and the mRNA-loaded nanoparticles have an mRNA encapsulation efficiency of 75% or greater after spray-drying the mixture.

2. The method of claim 1, wherein the one or more lipids are first mixed with the one or more mRNAs to form mRNA-loaded lipid nanoparticles before adding the one or more polymers.

3. The method of claim 1, wherein the one or more lipids are mixed with the one or more mRNAs and the one or more polymers in a single step to form mRNA-loaded lipid-polymer nanoparticles.

4. The method of claim 1, further comprising adding to the mixture one or more excipients prior to spray-drying the mixture.

5. The method of claim 1, wherein the plurality of spray-dried particles:

comprises a fraction of fine particles with a volume median diameter less than 5 μm;

has a Z-average size range of 10-3000 nm;

has a N/P ratio range from 1 to 20; and/or maintains an mRNA integrity of 90% or greater.

6. The method of claim 1, wherein the one or more mRNAs encode a protein or a peptide.

7. The method of claim 1, wherein the one or more mRNAs encode a peptide.

8. The method of claim 1, wherein the one or more mRNAs encodes a therapeutic protein.

9. The method of claim 8, wherein the therapeutic protein is cystic fibrosis conductance regulator (CFTR).

10. The method of claim 8, wherein the therapeutic protein is ornithine transcarbamylase (OTC).

11. The method of claim 1, wherein the polymethacrylate based polymer has a positively charged tertiary amine group with a methacrylic back bone.

12. The method of claim 1, wherein the one or more polymers comprise Eudragit EPO.

13. The method of claim 1, wherein the mRNA-loaded nanoparticles are mRNA-loaded lipid nanoparticles or mRNA-loaded lipid-polymer nanoparticles having a lipid: mRNA (N/P) ratio of 2 or 4.

14. The method of claim 1, wherein at least 20% of the plurality of spray-dried particles is fine particles having a volume median diameter of less than 5 μm.

15. The method of claim 1, wherein the one or more lipids comprise a cationic lipid.

16. The method of claim 1, wherein the one or more lipids comprise a polyethylene glycol (PEG)-modified lipid.

17. The method of claim 4, wherein the one or more excipients are selected from the group consisting of esters, urethanes, phosphoesters, phosphazenes, amino acids, collagen, chitosan, polysaccharides, albumin, surfactants, buffers, salts, and combination thereof.

18. The method of claim 4, wherein the one or more excipients comprise a poloxamer.

19. The method of claim 11, wherein the polymethacrylate based polymer having a positively charged tertiary amine group with a methacrylic back bone is represented by the following formula:

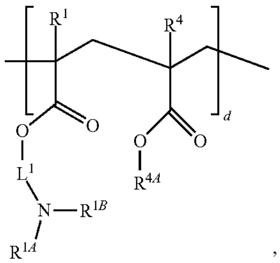

, wherein each of $R^1$ and $R^4$ is independently $C_1$-$C_6$ alkyl; each $L^1$ is independently $C_2$-$C_6$ alkylene; each of $R^{1A}$ and $R^{1B}$ is independently $C_1$-$C_6$ alkyl; each $R^{4A}$ is independently $C_1$-$C_6$ alkyl; and d is an integer of 1-500.

20. The method of claim 19, wherein the polymethacrylate based polymer having a positively charged tertiary amine group with a methacrylic back bone is represented by the following formula:

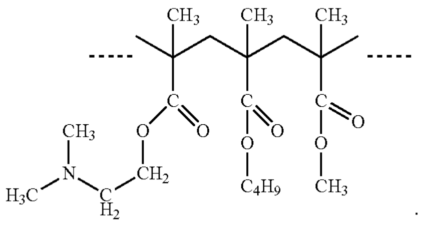

.

21. The method of claim 15, wherein the cationic lipid comprises one or more of DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA (1,2-dilinoleyloxy-N,N-dimethyl-3-aminopropane), DLin-KC2-DMA (2-(2,2-di((9Z,12Z)-octadeca-9,12-dien-1-yl)-1,3-dioxolan-4-yl)-N,N-dimethylethan-1-amine), HGT4003, cKK-E12, OF-02, and ICE (imidazole cholesterol ester), wherein HGT4003, cKK-E12, and OF-02 have the chemical structure:

24. The method of claim 19, wherein the one or more lipids comprise a cationic lipid comprising one or more of cKK-E12, OF-02, and ICE.

25. The method of claim 20, wherein the one or more lipids comprise a cationic lipid comprising one or more of cKK-E12, OF-02, and ICE.

(HGT4003)

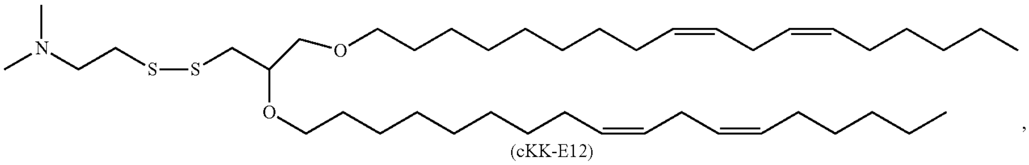

, (cKK-E12)

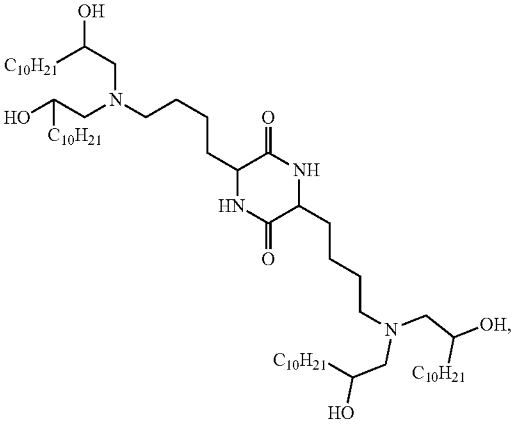

and (OF-02)

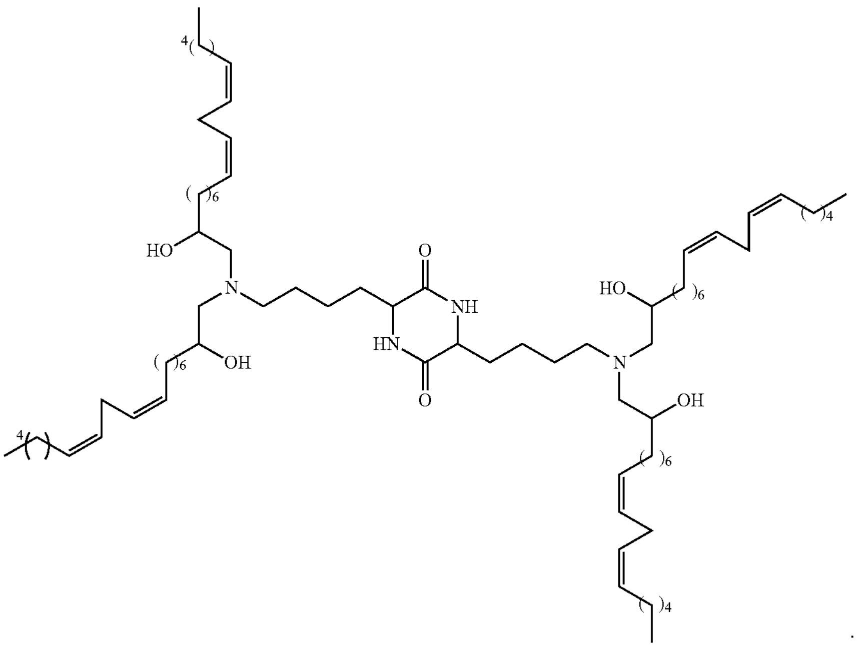

.

22. The method of claim 21, wherein the cationic lipid comprises one or more of cKK-E12, OF-02, and ICE.

23. The method of claim 11, wherein the one or more lipids comprise a cationic lipid comprising one or more of cKK-E12, OF-02, and ICE.

26. The method of claim 1, wherein the mRNA encapsulation efficiency is 80% or greater after spray-drying the mixture.

27. The method of claim 1, wherein the mixture is spray-dried with a spray-drying device that has an inlet temperature between 40° C. and 95° C. and/or an outlet temperature between 20° C. and 60° C.

28. The method of claim 1, wherein the mixture is spray-dried with a spray-drying device having an aspiration percentage of 95% or less.

* * * * *

SEQUENCE LISTING

<160> NUMBER OF SEQ ID NOS: 3

<210> SEQ ID NO 1
<211> LENGTH: 140
<212> TYPE: RNA
<213> ORGANISM: Artificial Sequence
<220> FEATURE:
<223> OTHER INFORMATION: Synthetic polynucleotide

<400> SEQUENCE: 1
ggacagaucg ccuggagacg ccauccacgc uguuuugacc uccauagaag acaccgggac 60
cgauccagcc uccgcggccg ggaacggugc auuggaacgc ggauuccccg ugccaagagu 120
gacucaccgu ccuugacacg 140

<210> SEQ ID NO 2
<211> LENGTH: 105
<212> TYPE: RNA
<213> ORGANISM: Artificial Sequence
<220> FEATURE:
<223> OTHER INFORMATION: Synthetic polynucleotide

<400> SEQUENCE: 2
cggguggcau cccugugacc ccuccccagu gccucuccug gcccuggaag uugccacucc 60
agugcccacc agccuugucc uaauaaaauu aaguugcauc aagcu 105

<210> SEQ ID NO 3
<211> LENGTH: 105

-continued

```
<212> TYPE: RNA
<213> ORGANISM: Artificial Sequence
<220> FEATURE:
<223> OTHER INFORMATION: Synthetic polynucleotide

<400> SEQUENCE: 3

ggguggcauc ccugugaccc cuccccagug ccucuccugg cccuggaagu ugccacucca     60

gugcccacca gccuuguccu aauaaaauua aguugcauca aagcu                    105
```